(12) United States Patent
O'Keefe et al.

(10) Patent No.: US 7,470,521 B2
(45) Date of Patent: Dec. 30, 2008

(54) RAGE PROTEIN DERIVATIVES

(75) Inventors: Theresa O'Keefe, Waltham, MA (US); Peter Luciano, Maynard, MA (US); Shixin Qin, Lexington, MA (US)

(73) Assignee: Critical Therapeutics, Inc., Lexington, MA (US)

( * ) Notice: Subject to any disclaimer, the term of this patent is extended or adjusted under 35 U.S.C. 154(b) by 170 days.

(21) Appl. No.: 11/186,422

(22) Filed: Jul. 20, 2005

(65) Prior Publication Data

US 2006/0057679 A1 Mar. 16, 2006

Related U.S. Application Data

(60) Provisional application No. 60/589,678, filed on Jul. 20, 2004.

(51) Int. Cl.
| | |
|---|---|
| C12P 21/06 | (2006.01) |
| A61K 39/00 | (2006.01) |
| C07H 21/04 | (2006.01) |
| C12P 21/04 | (2006.01) |
| C12N 5/00 | (2006.01) |
| C12N 5/16 | (2006.01) |
| C12N 15/64 | (2006.01) |
| C12N 1/20 | (2006.01) |

(52) U.S. Cl. .................. 435/69.1; 424/192.1; 536/23.4; 435/69.7; 435/325; 435/344.1; 435/91.4; 435/252.3

(58) Field of Classification Search ........................ None
See application file for complete search history.

(56) References Cited

U.S. PATENT DOCUMENTS

| | | | |
|---|---|---|---|
| 5,753,230 | A | 5/1998 | Brooks et al. |
| 5,852,174 | A | 12/1998 | Vlassara et al. |
| 5,864,018 | A | 1/1999 | Morser et al. |
| 6,228,642 | B1 | 5/2001 | Baker et al. |
| 6,465,422 | B1 | 10/2002 | Schmidt et al. |
| 6,468,555 | B1 | 10/2002 | Nakamura |
| 6,555,340 | B1 | 4/2003 | Schmidt et al. |
| 6,555,651 | B2 | 4/2003 | Stern et al. |
| 6,613,801 | B2 | 9/2003 | Mjalli et al. |
| 7,189,830 | B2 * | 3/2007 | Gillies et al. ................. 530/402 |
| 2001/0039256 | A1 | 11/2001 | Stern et al. |
| 2001/0053357 | A1 | 12/2001 | Stern et al. |
| 2002/0006957 | A1 | 1/2002 | Mjalli et al. |
| 2002/0106726 | A1 | 8/2002 | Schmidt et al. |
| 2002/0116725 | A1 | 8/2002 | Stern et al. |
| 2002/0122799 | A1 | 9/2002 | Stern et al. |
| 2002/0193432 | A1 | 12/2002 | Mjalli et al. |
| 2003/0032663 | A1 | 2/2003 | Mjalli et al. |
| 2003/0144201 | A1 * | 7/2003 | Tracey et al. ................. 514/12 |
| 2004/0082542 | A1 | 4/2004 | Mjalli et al. |
| 2005/0033017 | A1 | 2/2005 | Yamamoto et al. |
| 2006/0078562 | A1 | 4/2006 | Mjalli et al. |
| 2006/0140933 | A1 * | 6/2006 | Pittman et al. ........... 424/133.1 |

FOREIGN PATENT DOCUMENTS

| | | |
|---|---|---|
| WO | WO 97/08321 | 3/1997 |
| WO | WO 97/39121 | 10/1997 |
| WO | WO 00/78815 A1 | 12/2000 |
| WO | WO 01/12598 A2 | 2/2001 |
| WO | WO 01/92210 A1 | 12/2001 |
| WO | WO 02/30889 A2 | 4/2002 |
| WO | WO 02/069965 A1 | 9/2002 |
| WO | WO 02/070007 A1 | 9/2002 |
| WO | WO 02/070667 A2 | 9/2002 |
| WO | WO 02/074805 A1 | 9/2002 |
| WO | WO 02/092004 A2 | 11/2002 |
| WO | WO 03/075921 A2 | 9/2003 |
| WO | WO 2004/016229 A2 | 2/2004 |
| WO | WO 2005/026209 A2 | 3/2005 |
| WO | WO 2005/051995 A2 | 6/2005 |

OTHER PUBLICATIONS

Huttunen, H.J. et al., "Receptor for Advanced Glycation End Products-Binding COOH-terminal Motif of Amphoterin Inhibits Invasive Migration and Metastasis," *Cancer Research*, 62(16):4805-4811 (2002).
R & D Systems, Product Specifications and Use: "Recombinant Human RAGE/Fc Chimera" Catalog No. 1145-RG, (2004).
Rouhiainen, A., et al., "Regulation of Monocyte Migration by Amphoterin (HMGB1)," *Blood*, 104(4):1174-1182 (2004).
Schmidt, A., et al., "The Multiligand Receptor RAGE as a Progression Factor Amplifying Immune and Inflammatory Responses," *J. Clin. Invest.*, 108 (7):949-955 (2001).
Chavakis, T., et al., "The Pattern Recognition Receptor (RAGE) is a Counterreceptor for Leukocyte Integrins: A Novel Pathway for Inflammatory Cell Recruitment," *J. Exp. Med.*, 198 (10):1507-1515 (2003).
Neeper, M., et al., "Cloning and Expression of a Cell Surface Receptor for Advanced Glycosylation End Products of Proteins," *J. Biol. Chem.*, 267(21):14998-15004 (1992).
Ojwang, J.O., et al., "Modified Antisense Oligonucleotides Directed Against Tumor Necrosis Factor Receptor Type I Inhibit Tumor Necrosis Factor α-mediated Functions," *Biochemistry*, 36:6033-6045 (1997).
Pamfer, S., et al., "Neutralization of Tumor Necrosis Factor α (TNF α) Action on Cell Proliferation in Rat Blastocysts by Antisense Oligodeoxyribonucleotides Directed Against TNF α p60 Receptor," *Biol. Reprod.*, 52:1316-1326 (1995).

(Continued)

*Primary Examiner*—Lorraine Spector
*Assistant Examiner*—Elly-Gerald Stoica
(74) *Attorney, Agent, or Firm*—Hamilton, Brook, Smith & Reynolds, P.C.

(57) ABSTRACT

The present invention is drawn to fusion proteins comprising a Receptor for Advanced Glycation Endproducts (RAGE) and an immunoglobulin element. The invention also encompasses methods of treating a condition characterized by activation of an inflammatory cytokine cascade comprising administering such fusion proteins. The invention is also drawn to nucleic acids encoding the fusion proteins, as well as vectors and cells comprising such nucleic acids.

24 Claims, 24 Drawing Sheets

OTHER PUBLICATIONS

Yahata, N., et al., "Antisense Phosphorothioate Oligonucleotide Inhibits Interleukin 1β Production in the Human Macrophage-like Cell Line, U937," *Antisense Nucleic Acid Drug Dev.*, 6:55-61 (1996).

Leavitt, M.C., et al., "Inhibition of Interleukin-1β (IL-1β) Production in Human Cells by Ribozymes Against IL-1β and IL-1β Converting Enzyme (ICE)," *Antisense Nucleic Acid Drug Dev.*, 10:409-414 (2000).

Taylor, M.F., et al., "Effect of TNF-α Antisense Oligomers on Cytokine Production by Primary Murine Alveolar Macrophages," *Antisense Nucleic Acid Drug Dev.*, 8(3):199-205 (1998).

Hendrix, C., et al., "Selection of Hammerhead Ribozymes for Optimum Cleavage of Interleukin 6 mRNA," *Biochem. J.*, 314(Pt 2):655-661 (1996).

Kam, L.Y. and S.R. Targan, "TNF-α Antagonists for the Treatment of Crohn's Disease," *Expert Opin. Pharmacother.*, 1:615-622 (2000).

Nagahira, K., et al., "Humanization of a Mouse Neutralizing Monoclonal Antibody Against Tumor Necrosis Factor-α (TNF-α)," *J. Immunol. Methods*, 222:83-92 (1999).

Lavine, S.D., et al., "Circulating Antibody Against Tumor Necrosis Factor-alpha Protects Rat Brain from Reperfusion Injury," *J. Cereb. Blood Flow Metab.*, 18(1):52-58 (1998).

Holmes, S., et al., "Characterization of the In Vitro and In Vivo Activity of Monoclonal Antibodies to Human IL-18," *Hybridoma*, 19(5):363-367 (2000).

Yang, H., et al. "HMG-1 Rediscovered as a Cytokine," *Shock*, 15(4):247-253 (2001).

Wang, H., et al., "HMG-1 as a Late Mediator of Endotoxin Lethality in Mice," *Science*, 285:248-251 (1999).

Scaffidi, P., et al., "Release of Chromatin Protein HMGB1 by Necrotic Cells Triggers Inflammation," *Nature*, 418:191-195 (2002).

Wang, H., et al., "Proinflammatory Cytokines (Tumor Necrosis Factor and Interleukin 1) Stimulate Release of High Mobility Group Protein-1 by Pituicytes," *Surgery*, 126(2):389-392 (1999).

Andersson, U., et al., "High Mobility Group 1 Protein (HMG-1) Stimulates Proinflammatory Cytokine Synthesis in Human Monocytes," *J. Exp. Med.*, 192(4):565-570 (2000).

Liliensiek, B., et al., "Receptor for Advanced Glycation End Products (RAGE) Regulates Sepsis but not the Adaptive Immune Response," *J. Clin. Invest.*, 113(11):1641-1650 (2004).

GenBank Accession No. M91211, "Human Receptor for Advanced Glycosylation End Products (RAGE) mRNA, partial cds" (1993) [online] [retrieved on Mar. 21, 2006]. Retrieved from the Internet: <URL:http://www.ncbi.nlm.nih.gov/entrez/viewer.fcgi?db=nucleotide&val=190845>.

GenBank Accession No. NP_001127, "*Homo sapiens* Adaptor-related Protein Complex 1, beta 1 Subunit (AP1B1), Transcript Variant 1, mRNA" (2005) [online] [retrieved on Mar. 21, 2006]. Retrieved from the Internet: <URL:http://www.ncbi.nlm.nih.gov/entrez/viewer.fcgi?db=nuccore&val=22027650>.

GenBank Accession No. J00228, "*Homo sapiens* Immunoglobulin gamma-1 Heavy Chain Constant Region (IGHG1) Gene, Partial cds" (1998) [online] [retrieved on Mar. 21, 2006]. Retrieved from the Internet: <URL:http://www.ncbi.nlm.nih.gov/entrez/viewer.fcgi?db=nuccore&val=184739>.

GenBank Accession No. M91212, "Cow Receptor for Advanced Glycosylation End Products (RAGE) mRNA, Complete cds" (1993) [online] [retrieved on Mar. 21, 2006]. Retrieved from the Internet: <URL:http://www.ncbi.nlm.nih.gov/entrez/viewer.fcgi?db=nuccore&val=163650>.

GenBank Accession No. AAA64970, "HMG-1," (1995) [online] [retrieved on Mar. 21, 2006]. Retrieved from the Internet: <URL:http://www.ncbi.nlm.nih.gov/entrez/viewer.fcgi?db=protein&val=184251>.

GenBank Accession No. AAB08987, "Non-Histone Chromatin Protein HMG1 [*Homo sapiens*]," (1996) [online] [retrieved on Mar. 21, 2006]. Retrieved from the Internet: <URL:http://www.ncbi.nlm.nih.gov/entrez/viewer.fcgi?db=protein&val=1435197>.

GenBank Accession No. P07155, "High Mobility Group Protein 1 (HMG-1) (Amphoterin) (Heparin-Binding Protein p30)," (2004) [online] [retrieved on Mar. 21, 2006]. Retrieved from the Internet: <URL:http://www.ncbi.nlm.nih.gov/entrez/viewer.fcgi?db=protein&val=1708258>.

GenBank Accession No. AAA20508,"HMG-1," (1994) [online] [retrieved on Mar. 21, 2006]. Retrieved from the Internet: <URL:http://www.ncbi.nlm.nih.gov/entrez/viewer.fcgi?db=protein&val=437102>.

GenBank Accession No. S29857, "Nonhistone Chromosomal Protein HMG-1—Human," (1999) [online] [retrieved on Mar. 21, 2006]. Retrieved from the Internet: <URL:http://www.ncbi.nlm.nih.gov/entrez/viewer.fcgi?db=protein&val=478813>.

GenBank Accession No. P09429, "High Mobility Group Protein 1 (HMG-1) (High Mobility Group Protein B1," (1989) [online] [retrieved on Mar. 21, 2006]. Retrieved from the Internet: <URL:http://www.ncbi.nlm.nih.gov/entrez/viewer.fcgi?db=protein&val=123369>.

GenBank Accession No. NP_002119, "High-Mobility Group Box 1 [*Homo sapiens*]," (2006) [online] [retrieved on Mar. 21,2006]. Retrieved from the Internet: <URL:http://www.ncbi.nlm.nih.gov/entrez/viewer.fcgi?db=protein&val=4504425>.

GenBank Accession No. CAA31110, "Unnamed Protein Product [*Homo sapiens*]," (2005) [online] [retrieved on Mar. 21, 2006]. Retrieved from the Internet: <URL:http://www.ncbi.nlm.nih.gov/entrez/viewer.fcgi?db=protein&val=32327>.

GenBank Accession No. S02826, "Nonhistone Chromosomal Protein HMG-1—human," (1999) [online] [retrieved on Mar. 23, 2006]. Retrieved from the Internet: <URL:http://www.ncbi.nlm.nih.gov/entrez/viewer.fcgi?db=protein&val=88270>.

GenBank Accession No. U00431, "Mus musculus HMG-1 mRNA, Complete cds" (1994) [online] [retrieved on Mar. 21, 2006]. Retrieved from the Internet: <URL:http://www.ncbi.nlm.nih.gov/entrez/viewer.fcgi?db=nuccore&val=437101>.

GenBank Accession No. X67668, "M. Musculus mRNA for High Mobility Group 2 Protein," (2005) [online] [retrieved on Mar. 21, 2006]. Retrieved from the Internet: <URL:http://www.ncbi.nlm.nih.gov/entrez/viewer.fcgi?db=nuccore&val=51338>.

GenBank Accession No. NP_005333, "High-Mobility Group Box 3 [*Homo sapiens*]," (2005) [online] [retrieved on Mar. 21, 2006]. Retrieved from the Internet: <URL:http://www.ncbi.nlm.nih.gov/entrez/viewer.fcgi?db=protein&val=71143137>.

GenBank Accession No. NM_016957, "Mus musculus High Mobility Group Nucleosomal Binding Domain 2," (2006) [online] [retrieved on Mar. 21, 2006]. Retrieved from the Internet: <URL:http://www.ncbi.nlm.nih.gov/entrez/viewer.fcgi?db=nuccore&val=86198321>.

GenBank Accession No. J04197, "*Rattus norvegicus* 6-phosphofructo-2-kinase/fructose-2, 6-bisphosphatase mRNA, Complete cds," (1995) [online] [retrieved on Mar. 21, 2006]. Retrieved from the Internet: <URL:http://www.ncbi.nlm.nih.gov/entrez/viewer.fcgi?db=nuccore&val=202557>.

GenBank Accession No. U51677, "Human Non-histone Chromatin Protein HMG1 (HMG1) Gene," (1996) [online] [retrieved on Mar. 21, 2006]. Retrieved from the Internet: <URL:http://www.ncbi.nlm.nih.gov/entrez/viewer.fcgi?db=nuccore&val=1435196>.

GenBank Accession No. CAA55631, "Cadherin [*Rattus norvegicus* ]," (2005) [online] [retrieved on Mar. 21, 2006]. Retrieved from the Internet: <URL:http://www.ncbi.nlm.nih.gov/entrez/viewer.fcgi?db=protein&val=505563>.

GenBank Accession No. NP_037095, "High Mobility Group Box 1 [*Rattus norvegicus* ]," (2005) [online] [retrieved on Mar. 21, 2006]. Retrieved from the Internet: <URL:http://www.ncbi.nlm.nih.gov/entrez/viewer.fcgi?db=protein&val=6981026>.

GenBank Accession No. CAA31284, "Unnamed Protein Product [Bos taurus]," (2005) [online] [retrieved on Mar. 21, 2006]. Retrieved from the Internet: <URL:http://www.ncbi.nlm.nih.gov/entrez/viewer.fcgi?db=protein&val=417>.

GenBank Accession No. M83665, "Human High Mobility Group 2 Protein (HMG-2) gene, Complete cds," (1994) [online] [retrieved on Mar. 21, 2006]. Retrieved from the Internet: <URL:http://www.ncbi.nlm.nih.gov/entrez/viewer.fcgi?db=nuccore&val=184235>.

GenBank Accession No. NM_005342, "*Homo sapiens* High-mobility Group Box 3 (HMGB3), mRNA," (2005) [online] [retrieved on Mar. 21, 2006]. Retrieved from the Internet: <URL:http://www.ncbi.nlm.nih.gov/entrez/viewer.fcgi?db=nuccore&val=71143136>.

GenBank Accession No. P05114, "Nonhistone Chromosomal Protein HMG-14 (High-Mobility Group Nucleosome-Binding Domain 1)," (1987) [online] [retrieved on Mar. 24, 2006]. Retrieved from the Internet: <URL:http://www.ncbi.nlm.nih.gov/entrez/viewer.fcgi?db=protein&val=123101>.

GenBank Accession No. X13546, "Human HMG-17 Gene for Nonhistone Chromosomal Protein HMG-17," (1997) [online] [retrieved on Mar. 21, 2006]. Retrieved from the Internet: <URL:http://www.ncbi.nlm.nih.gov/entrez/viewer.fcgi?db=nuccore&val=32328>.

GenBank Accession No. L17131, "*Homo sapiens* High Mobility Group Protein (HMG-I(Y)) Gene Exons 1-8, Complete cds" (1999) [online] [retrieved on Mar. 21, 2006]. Retrieved from the Internet: <URL:http://www.ncbi.nlm.nih.gov/entrez/viewer.fcgi?db=nuccore&val=306868>.

GenBank Accession No. M23618, "Human HMG-Y Protein Isoform mRNA (HMGI gene), Clone 11D," (1996) [online] [retrieved on Mar. 21, 2006]. Retrieved from the Internet: <URL:http://www.ncbi.nlm.nih.gov/entrez/viewer.fcgi?db=nuccore&val=184258>.

GenBank Accession No. X02666, "Trout mRNA for High Mobility Group Protein HMG-T," (2005) [online] [retrieved on Mar. 21, 2006]. Retrieved from the Internet: <URL:http://www.ncbi.nlm.nih.gov/entrez/viewer.fcgi?db=nuccore&val=64327>.

GenBank Accession No. L32859, "Rainbow Trout HMG-I Gene Exons 2-5, Complete cds," (1995) [online] [retrieved on Mar. 21, 2006]. Retrieved from the Internet: <URL:http://www.ncbi.nlm.nih.gov/entrez/viewer.fcgi?db=nuccore&val=609550>.

GenBank Accession No. D30765, "Xenopus laevis mRNA for HMG-X Protein, Complete cds," (1999) [online] [retrieved on Mar. 21, 2006]. Retrieved from the Internet: <URL:http://www.ncbi.nlm.nih.gov/entrez/viewer.fcgi?db=nuccore&val=639690>.

GenBank Accession No. X71138, "D. Melanogaster HMG-D mRNA," (1993) [online] [retrieved on Mar. 21, 2006]. Retrieved from the Internet: <URL:http://www.ncbi.nlm.nih.gov/entrez/viewer.fcgi?db=nuccore&val=296942>.

GenBank Accession No. X71139, "D. melanogaster HMG-Z mRNA," (2005) [online] [retrieved on Mar. 21, 2006]. Retrieved from the Internet: <URL:http://www.ncbi.nlm.nih.gov/entrez/viewer.fcgi?db=nuccore&val=296944>.

GenBank Accession No. Z48008, "S. cerevisiae Chromosome IV Cosmid 8119," (2005) [online] [retrieved on Mar. 21, 2006]. Retrieved from the Internet: <URL:http://www.ncbi.nlm.nih.gov/entrez/viewer.fcgi?db=nuccore&val=642799>.

GenBank Accession No. O00479, "Nonhistone Chromosomal Protein HMG-17-like 3 (Non-Histone Chromosomal Protein) (High-Mobility Group Nucleosome Binding Domain 4)," (2005) [online] [retrieved on Mar. 21, 2006]. Retrieved from the Internet: <URL:http://www.ncbi.nlm.nih.gov/entrez/viewer.fcgi?db=protein&val=20138140>.

GenBank Accession No. Z11540, "T. Aestivum mRNA for High Mobility Group Protein (HMGW)," (2005) [online] [retrieved on Mar. 21, 2006]. Retrieved from the Internet: <URL:http://www.ncbi.nlm.nih.gov/entrez/viewer.fcgi?db=nuccore&val=21802>.

GenBank Accession No. X53390, "Human mRNA for Upstream Binding Factor (hUBF)," (1999) [online] [retrieved on Mar. 21, 2006]. Retrieved from the Internet: <URL:http://www.ncbi.nlm.nih.gov/entrez/viewer.fcgi?db=nuccore&val=509240>.

GenBank Accession No. U13695, "Human Homolog of Yeast mutL(hPMS1) Gene, Complete cds," (1995) [online] [retrieved on Mar. 21, 2006]. Retrieved from the Internet: <URL:http://www.ncbi.nlm.nih.gov/entrez/viewer.fcgi?db=nuccore&val=535512>.

GenBank Accession No. M86737, "Human High Mobility Group Box (SSRP1) mRNA, Complete cds," (1994) [online] [retrieved on Mar. 21, 2006]. Retrieved from the Internet: <URL:http://www.ncbi.nlm.nih.gov/entrez/viewer.fcgi?db=nuccore&val=184241>.

GenBank Accession No. M74017, "T. brucei Rhodesiense HMG1-like Protein mRNA, Complete cds" (1993) [online] [retrieved on Mar. 21, 2006]. Retrieved from the Internet: <URL:http://www.ncbi.nlm.nih.gov/entrez/viewer.fcgi?db=nuccore&val=162108>.

GenBank Accession No. X53772, "*H. sapiens* SRY Gene," (1997) [online] [retrieved on Mar. 21, 2006]. Retrieved from the Internet: <URL:http://www.ncbi.nlm.nih.gov/entrez/viewer.fcgi?db=nuccore&val=36604>.

GenBank Accession No. AB009451, "Alternaria alternata MAT1 Gene," [online] [retrieved on Mar. 21, 2006]. Retrieved from the Internet: <URL:http://www.ncbi.nlm.nih.gov/entrez/viewer.fcgi?db=nuccore&val=4520345>.

GenBank Accession No. X53431, "Yeast Gene for STE11," [online] [retrieved on Mar. 21, 2006]. Retrieved from the Internet: <URL:http://www.ncbi.nlm.nih.gov/entrez/viewer.fcgi?db=nuccore&val=4553>.

GenBank Accession No. AF107043, "*Homo sapiens* Clone pCL11 DNA-binding Protein SOX14 (SOX14) Gene, Complete cds," (1998) [online] [retrieved on Mar. 21, 2006]. Retrieved from the Internet: <URL:http://www.ncbi.nlm.nih.gov/entrez/viewer.fcgi?db=nuccore&val=4008100>.

GenBank Accession No. Y13436, "*Homo sapiens* Sox1 Gene," (2005) [online] [retrieved on Mar. 21, 2006]. Retrieved from the Internet: <URL:http://www.ncbi.nlm.nih.gov/entrez/viewer.fcgi?db=nuccore&val=4128158>.

GenBank Accession No. Z31560, "*H. sapiens* Sox-2 mRNA," (2005) [online] [retrieved on Mar. 21, 2006]. Retrieved from the Internet: <URL:http://www.ncbi.nlm.nih.gov/entrez/viewer.fcgi?db=nuccore&val=854181>.

GenBank Accession No. X71135, "*H. sapiens* Sox3 Gene," (2005) [online] [retrieved on Mar. 21, 2006]. Retrieved from the Internet: http://www.ncbi.nlm.nih.gov/entrez/viewer.fcgi?db=nuccore&val=468790>.

GenBank Accession No. AF309034, "*Homo sapiens* SOX6 mRNA," (2001) [online] [retrieved on Mar. 21, 2006]. Retrieved from the Internet: <URL:http://www.ncbi.nlm.nih.gov/entrez/viewer.fcgi?db=nuccore&val=13435017>.

GenBank Accession No. AF226675, "*Homo sapiens* Transcription Factor SOX8 mRNA, Complete cds," (2000) [online] [retrieved on Mar. 21, 2006]. Retrieved from the Internet: <URL:http://www.ncbi.nlm.nih.gov/entrez/viewer.fcgi?db=nuccore&val=7025446>.

GenBank Accession No. AJ001183, "*Homo sapiens* mRNA for Sox10 Protein," (2005) [online] [retrieved on Mar. 21, 2006]. Retrieved from the Internet: <URL:http://www.ncbi.nlm.nih.gov/entrez/viewer.fcgi?db=nuccore&val=2909359>.

GenBank Accession No. X73039, "*H. sapiens* SOX-12 Gene," (2005) [online] [retrieved on Mar. 21, 2006]. Retrieved from the Internet: <URL:http://www.ncbi.nlm.nih.gov/entrez/viewer.fcgi?db=nuccore&val=312151>.

GenBank Accession No. AF107044, "*Homo sapiens* Clone pCL4 DNA-binding Protein SOX21 (SOX21) Gene, Complete cds," (1998) [online] [retrieved on Mar. 21, 2006]. Retrieved from the Internet: <URL:http://www.ncbi.nlm.nih.gov/entrez/viewer.fcgi?db=nuccore&val=4008102>.

GenBank Accession No. X58636, "Mouse LEF1 mRNA for Lymphoid Enhancer Binding Factor 1," (1999) [online] [retrieved on Mar. 21, 2006]. Retrieved from the Internet: <URL:http://www.ncbi.nlm.nih.gov/entrez/viewer.fcgi?db=nuccore&val=52887>.

GenBank Accession No. X59869, "Human TCF-1 mRNA for T Cell Factor 1 (Splice Form A)," (2005) [online] [retrieved on Mar. 21, 2006]. Retrieved from the Internet: <URL:http://www.ncbi.nlm.nih.gov/entrez/viewer.fcgi?db=nuccore&val=36785>.

GenBank Accession No. M62810, "Human Mitochondrial Transcription Factor 1 mRNA, Complete cds," (1995) [online] [retrieved on Mar. 21, 2006]. Retrieved from the Internet: <URL:http://www.ncbi.nlm.nih.gov/entrez/viewer.fcgi?db=nuccore&val=188563>.

GenBank Accession No. U36501, "Human SP100-B (SP100-B) mRNA, Complete cds," (1996) [online] [retrieved on Mar. 21, 2006]. Retrieved from the Internet: <URL:http://www.ncbi.nlm.nih.gov/entrez/viewer.fcgi?db=nuccore&val=1173655>.

GenBank Accession No. AAH81839, "High Mobility Group Box 1 [*Rattus norvegicus*]," (2004) [online] [retrieved on Mar. 21, 2006]. Retrieved from the Internet: <URL:http://www.ncbi.nlm.nih.gov/entrez/viewer.fcgi?db=protein&val=51859468>.

GenBank Accession No. NP_990233, "High-Mobility Group Box 1 [*Gallus gallus*]," (2005) [online] [retrieved on Mar. 21, 2006].

Retrieved from the Internet: <URL:http://www.ncbi.nlm.nih.gov/entrez/viewer.fcgi?db=protein&val=45382473>.

GenBank Accession No. AAC27653, "High Mobility Group Protein [*Spalax ehrenbergi*]," (1999) [online] [retrieved on Mar. 21, 2006]. Retrieved fron the Internet: <URL:http://www.ncbi.nlm.nih.gov/entrez/viewer.fcgi?db=protein&val=5764680>.

GenBank Accession No. P07746, "High Mobility Group-T Protein (HMG-T) (HMG-T1) (HMG-1)," (1988) [online] [retrieved on Mar. 21, 2006]. Retrieved from the Internet: <URL:http://www.ncbi.nlm.nih.gov/entrez/viewer.fcgi?db=protein&val=123382>.

GenBank Accession No. AAA58771, "HMG-1," (1995) [online] [retrieved on Mar. 21, 2006]. Retrieved from the Internet: <URL:http://www.ncbi.nlm.nih.gov/entrez/viewer.fcgi?db=protein&val=609551>.

GenBank Accession No. AAQ97791, "High-mobility Group Box 1 [*Danio rerio*]," (2004) [online] [retrieved on Mar. 21, 2006]. Retrieved from the Internet: <URL:http://www.ncbi.nlm.nih.gov/entrez/viewer.fcgi?db=protein&val=37681827>.

GenBank Accession No. AAH01063, "High-mobility Group Box 2 [*Homo sapiens*]," (2004) [online] [retrieved on Mar. 21, 2006]. Retrieved from the Internet: <URL:http://www.ncbi.nlm.nih.gov/entrez/viewer.fcgi?db=protein&val=12654471>.

GenBank Accession No. P10103, "High Mobility Group Protein 1 (HMG-1) (High Mobility Group Protein B1)," (1989) [online] [retrieved on Mar. 21, 2006]. Retrieved from the Internet: <URL:http://www.ncbi.nlm.nih.gov/entrez/viewer.fcgi?db=protein&val=123367>.

* cited by examiner

```
   1 ggggcagccg gaacagcagt tggagcctgg gtgctggtcc tcagtctgtg gggggcagta
  61 gtaggtgctc aaaacatcac agcccggatt ggcgagccac tggtgctgaa gtgtaagggg
 121 gcccccaaga aaccacccca gcggctggaa tggaaactga acacaggccg gacagaagct
 181 tggaaggtcc tgtctcccca gggaggaggc ccctgggaca gtgtggctcg tgtccttccc
 241 aacggctccc tcttccttcc ggctgtcggg atccaggatg aggggatttt ccggtgcagg
 301 gcaatgaaca ggaatggaaa ggagaccaag tccaactacc gagtccgtgt ctaccagatt
 361 cctgggaagc cagaaattgt agattctgcc tctgaactca cggctggtgt tcccaataag
 421 gtggggacat gtgtgtcaga gggaagctac cctgcaggga ctcttagctg gcacttggat
 481 gggaagcccc tggtgcctaa tgagaaggga gtatctgtga aggaacagac caggagacac
 541 cctgagacag ggctcttcac actgcagtcg gagctaatgg tgaccccagc ccggggagga
 601 gatccccgtc ccaccttctc ctgtagcttc agcccaggcc ttccccgaca ccgggccttg
 661 cgcacagccc ccatccagcc ccgtgtctgg gagcctgtgc ctctggagga ggtccaattg
 721 gtggtggagc cagaaggtgg agcagtagct cctggtggaa ccgtaaccct gacctgtgaa
 781 gtccctgccc agccctctcc tcaaatccac tggatgaagg atggtgtgcc cttgccccct
 841 cccccagcc ctgtgctgat cctccctgag atagggcctc aggaccaggg aacctacagc
 901 tgtgtggcca cccattccag ccacgggccc caggaaagcc gtgctgtcag catcagcatc
 961 atcgaaccag gcgaggaggg gccaactgca ggctctgtgg gaggatcagg gctgggaact
1021 ctagccctgg ccctggggat cctgggaggc ctggggacag ccgcctgct cattggggtc
1081 atcttgtggc aaaggcggca acgccgagga gaggagagga aggcccaga aaaccaggag
1141 gaagaggagg agcgtgcaga actgaatcag tcggaggaac ctgaggcagg cgagagtagt
1201 actggagggc cttgaggggc ccacagacag atcccatcca tcagctccct tttcttttc
1261 ccttgaactg ttctggcctc agaccaactc tctcctgtat aatctctctc ctgtataacc
1321 ccaccttgcc aagctttctt ctacaaccag agcccccac aatgatgatt aaacacctga
1381 cacatcttgc a
```

FIG. 1A

| | |
|---|---|
| 1 | maagtavgaw vlvlslwgav vgaqnitari geplvlkckg apkkppqrle wklntgrtea |
| 61 | wkvlspqggg pwdsvarvlp ngslflpavg iqdegifrcq amnrngketk snyrvrvyqi |
| 121 | pgkpeivdsa seltagvpnk vgtcvsegsy pagtlswhld gkplvpnekg vsvkeqtrrh |
| 181 | petglftlqs elmvtpargg dprptfscsf spglprhral rtapiqprvw epvpleevql |
| 241 | vvepeggava pggtvtltce vpaqpspqih wmkdgvplpl ppspvlilpe igpqdqgtys |
| 301 | cvathsshgp qesravsisi iepgeegpta gsvggsglgt lalalgilgg lgtaalligv |
| 361 | ilwqrrqrrg eerkapenqe eeeeraelnq seepeagess tggp |

FIG. 1B

```
1     agctttctgg ggcaggccag gcctgacctt ggctttgggg cagggagggg gctaaggtga
61    ggcaggtggc gccagcaggt gcacacccaa tgcccatgag cccagacact ggacgctgaa
121   cctcgcggac agttaagaac caggggcct ctgcgcctgg gcccagctct gtcccacacc
181   gcggtcacat ggcaccacct ctcttgcagc ctccaccaag ggcccatcgg tcttccccct
241   ggcaccctcc tccaagagca cctctggggg cacagcggcc ctgggctgcc tggtcaagga
301   ctacttcccc gaaccggtga cggtgtcgtg gaactcaggc gccctgacca gcggcgtgca
361   caccttcccg gctgtcctac agtcctcagg actctactcc ctcagcagcg tggtgaccgt
421   gccctccagc agcttgggca cccagaccta catctgcaac gtgaatcaca agcccagcaa
481   caccaaggtg gacaagaaag ttggtgagag gccagcacag ggagggaggg tgtctgctgg
541   aagcaggctc agcgctcctg cctggacgca tcccggctat gcagccccag tccagggcag
601   caaggcaggc cccgtctgcc tcttcacccg gagcctctgc ccgccccact catgctcagg
661   gagagggtct tctggctttt tccaggctc tgggcaggca caggctaggt gccctaacc
721   caggccctgc acacaagggg gcaggtgctg ggctcagacc tgccaagagc catatccggg
781   aggaccctgc ccctgaccta agcccacccc aaaggccaaa ctctccactc cctcagctcg
841   gacaccttct ctcctcccag attccagtaa ctcccaatct tctctctgca gagcccaaat
901   cttgtgacaa aactcacaca tgcccaccgt gcccaggtaa gccagcccag gcctcgccct
961   ccagctcaag gcgggacagg tgccctagag tagcctgcat ccagggacag gccccagccg
1021  ggtgctgaca cgtccacctc catctcttcc tcagcacctg aactcctggg gggaccgtca
1081  gtcttcctct tccccccaaa acccaaggac accctcatga tctcccggac ccctgaggtc
1141  acatgcgtgg tggtggacgt gagccacgaa gaccctgagg tcaagttcaa ctggtacgtg
1201  gacggcgtgg aggtgcataa tgccaagaca aagccgcggg aggagcagta acacagcacg
1261  taccgggtgg tcagcgtcct caccgtcctg caccaggact ggctgaatgg caaggagtac
1321  aagtgcaagg tctccaacaa agccctccca gcccccatcg agaaaaccat ctccaaagcc
1381  aaaggtggga cccgtggggt gcgagggcca catggacaga ggccggctcg gcccaccctc
1441  tgccctgaga gtgaccgctg taccaacctc tgtcctacag ggcagccccg agaaccacag
1501  gtgtacaccc tgcccccatc ccgggatgag ctgaccaaga accaggtcag cctgacctgc
1561  ctggtcaaag gcttctatcc cagcgacatc gccgtggagt gggagagcaa tgggcagccg
1621  gagaacaact acaagaccac gcctcccgtg ctggactccg acggctcctt cttcctctac
1681  agcaagctca ccgtggacaa gagcaggtgg cagcagggga acgtcttctc atgctccgtg
1741  atgcatgagg ctctgcacaa ccactacacg cagaagagcc tctccctgtc tccgggtaaa
1801  tgagtgcgac ggccggcaag ccccgctccc cgggctctcg cggtcgcacg aggatgcttg
1861  gcacgtaccc cctgtacata cttcccgggc gcccagcatg gaaataaagc acccagcgct
1921  gccctgggcc cctgcgagac tgtgatggtt ctttccacgg gtcaggccga gtctgaggcc
1981  tgagtggcat gagggaggca gagcgggtc
```

FIG. 2A

STKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGK

FIG. 2B ccggaattcctcaccATGGCAGCCGGAACAGCAGTTGGAGCCTGGGTGCTGGTCCTCAGTC
TGTGGGGGGCAGTAGTAGGTGCTCAAAACATCACAGCCCGGATTGGCGAGCCACT
GGTGCTGAAGTGTAAGGGGGCCCCCAAGAAACCACCCCAGCGGCTGGAATGGAA
ACTGAACACAGGCCGGACAGAAGCTTGGAAGGTCCTGTCTCCCCAGGGAGGAGGC
CCCTGGGACAGTGTGGCTCGTGTCCTTCCCAACGGCTCCCTCTTCCTTCCGGCTGTC
GGGATCCAGGATGAGGGGATTTTCCGGTGCCAGGCAATGAACAGGAATGGAAAG
GAGACCAAGTCCAACTACCGAGTCCGTGTCTACCAGATTCCTGGGAAGCCAGAAA
TTGTAGATTCTGCCTCTGAACTCACGGCTGGTGTTCCCAATAAGGTGGGGACATGT
GTGTCAGAGGGAAGCTACCCTGCAGGGACTCTTAGCTGGCACTTGGATGGGAAGC
CCCTGGTGCCTAATGAGAAGGGAGTATCTGTGAAGGAACAGACCAGGAGACACCC
TGAGACAGGGCTCTTCACACTGCAGTCGGAGCTAATGGTGACCCCAGCCCGGGGA
GGAGATCCCCGTCCCACCTTCTCCTGTAGCTTCAGCCCAGGCCTTCCCCGACACCG
GGCCTTGCGCACAGCCCCCATCCAGCCCCGTGTCTGGGAGCCTGTGCCTCTGGAGG
AGGTCCAATTGGTGGTGGAGCCAGAAGGTGGAGCAGTAGCTCCTGGTGGAACCGT
AACCCTGACCTGTGAAGTCCCTGCCCAGCCCTCTCCTCAAATCCACTGGATGAAGG
ATGGTGTGCCCTTGCCCCTTCCCCCCAGCCCTGTGCTGATCCTCCCTGAGATAGGG
CCTCAGGACCAGGGAACCTACAGCTGTGTGGCCACCCATTCCAGCGACAAAACTC
ACACATGCCCACCGTGCCCAGCACCTGAACTCGCGGGGGCACCGTCAGTCTTCCTC
TTCCCCCCAAAACCCAAGGACACCCTCATGATCTCCCGGACCCCTGAGGTCACATG
CGTGGTGGTGGACGTGAGCCACGAAGACCCTGAGGTCAAGTTCAACTGGTACGTG
GACGGCGTGGAGGTGCATAATGCCAAGACAAAGCCGCGGGAGGAGCAGTACAAC
AGCACGTACCGTGTGGTCAGCGTCCTCACCGTCCTGCACCAGGACTGGCTGAATG
GCAAGGAGTACAAGTGCAAGGTCTCCAACAAAGCCCTCCCAGCCCCCATCGAGAA
AACCATCTCCAAAGCCAAAGGGCAGCCCCGAGAACCACAGGTGTACACCCTGCCC
CCATCCCGGGATGAGCTGACCAAGAACCAGGTCAGCCTGACCTGCCTGGTCAAAG
GCTTCTATCCCAGCGACATCGCCGTGGAGTGGGAGAGCAATGGGCAGCCGGAGAA
CAACTACAAGACCACGCCTCCCGTGCTGGACTCCGACGGCTCCTTCTTCCTCTACA
GCAAGCTCACCGTGGACAAGAGCAGGTGGCAGCAGGGGAACGTCTTCTCATGCTC
CGTGATGCATGAGGCTCTGCACAACCACTACACGCAGAAGAGCCTCTCCCTGTCTC
CGGGTAAAtaatctagagca

FIG. 3A

AVVGAQNITARIGEPLVLKCKGAPKKPPQRLEWKLNTGRTEAWKVLSPQGGGPWDS
VARVLPNGSLFLPAVGIQDEGIFRCQAMNRNGKETKSNYRVRVYQIPGKPEIVDSASE
LTAGVPNKVGTCVSEGSYPAGTLSWHLDGKPLVPNEKGVSVKEQTRRHPETGLFTLQ
SELMVTPARGGDPRPTFSCSFSPGLPRHRALRTAPIQPRVWEPVPLEEVQLVVEPEGGA
VAPGGTVTLTCEVPAQPSPQIHWMKDGVPLPLPPSPVLILPEIGPDQGTYSCVATH-
SSDKTHTCPPCPAPE<u>AGA</u>PSVFLFPPKPKDTLMISRTPEVTCVVVDVSHEDPEV
KFNWYVDGVEVHNAKTKPREEQYNSTYRVVSVLTVLHQDWLNGKEYKCKVSNKAL
PAPIEKTISKAKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHYTQKSLSLS
PGK

FIG. 3B

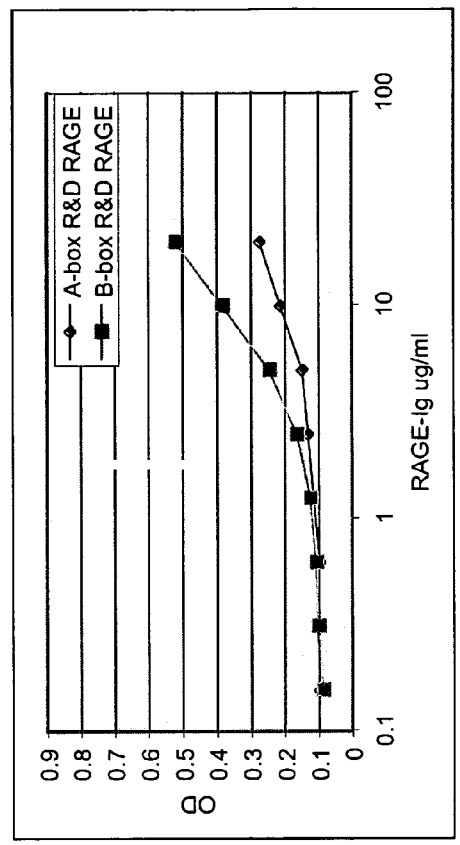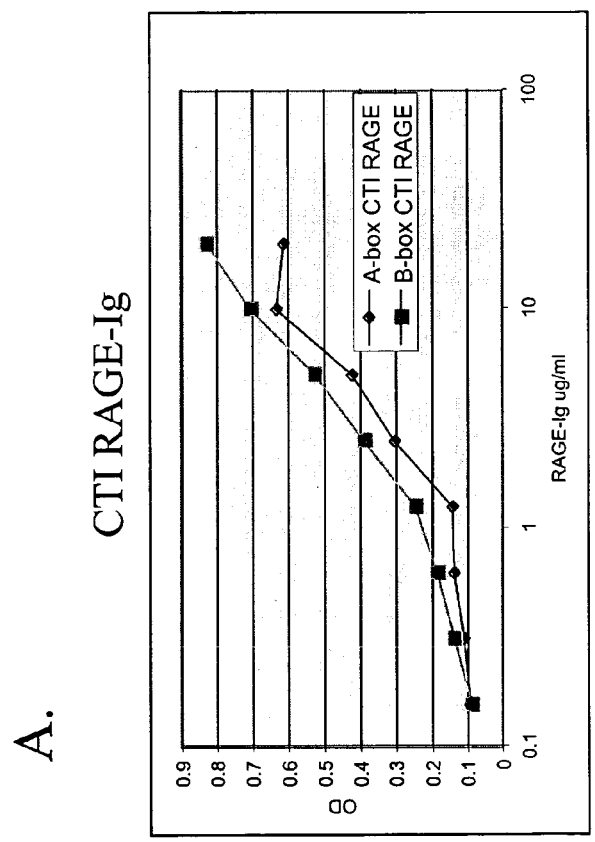
FIG. 7 ccggaattcctcaccATGGCAGCCGGAACAGCAGTTGGAGCCTGGGTGCTGGTCCTCAGTC
TGTGGGGGGCAGTAGTAGGTGCTCAAAACATCACAGCCCGGATTGGCGAGCCACT
GGTGCTGAAGTGTAAGGGGGCCCCCAAGAAACCACCCCAGCGGCTGGAATGGAA
ACTGAACACAGGCCGGACAGAAGCTTGGAAGGTCCTGTCTCCCCAGGGAGGAGGC
CCCTGGGACAGTGTGGCTCGTGTCCTTCCCAACGGCTCCCTCTTCCTTCCGGCTGTC
GGGATCCAGGATGAGGGGATTTTCCGGTGCCAGGCAATGAACAGGAATGGAAAG
GAGACCAAGTCCAGCGACAAAACTCACACATGCCCACCGTGCCCAGCACCTGAAC
TCGCGGGGGCACCGTCAGTCTTCCTCTTCCCCCCAAAACCCAAGGACACCCTCATG
ATCTCCCGGACCCCTGAGGTCACATGCGTGGTGGTGGACGTGAGCCACGAAGACC
CTGAGGTCAAGTTCAACTGGTACGTGGACGGCGTGGAGGTGCATAATGCCAAGAC
AAAGCCGCGGGAGGAGCAGTACAACAGCACGTACCGTGTGGTCAGCGTCCTCACC
GTCCTGCACCAGGACTGGCTGAATGGCAAGGAGTACAAGTGCAAGGTCTCCAACA
AAGCCCTCCCAGCCCCCATCGAGAAAACCATCTCCAAAGCCAAAGGGCAGCCCCG
AGAACCACAGGTGTACACCCTGCCCCCATCCCGGGATGAGCTGACCAAGAACCAG
GTCAGCCTGACCTGCCTGGTCAAAGGCTTCTATCCCAGCGACATCGCCGTGGAGTG
GGAGAGCAATGGGCAGCCGGAGAACAACTACAAGACCACGCCTCCCGTGCTGGA
CTCCGACGGCTCCTTCTTCCTCTACAGCAAGCTCACCGTGGACAAGAGCAGGTGGC
AGCAGGGGAACGTCTTCTCATGCTCCGTGATGCATGAGGCTCTGCACAACCACTAC
ACGCAGAAGAGCCTCTCCCTGTCTCCGGGTAAAtaatctagagca

FIG. 13A

AVVGAQNITARIGEPLVLKCKGAPKKPPQRLEWKLNTGRTEAWKVLSPQGGGPWDS
VARVLPNGSLFLPAVGIQDEGIFRCQAMNRNGKETK-
SSDKTHTCPPCPAPE<u>LAGA</u>PSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPGK

FIG. 13B ccggaattcctcaccATGGCAGCCGGAACAGCAGTTGGAGCCTGGGTGCTGGTCCTCAGTC
TGTGGGGGGCAGTAGTAGGTGCTCAAAACATCACAGCCCGGATTGGCGAGCCACT
GGTGCTGAAGTGTAAGGGGGCCCCCAAGAAACCACCCCAGCGGCTGGAATGGAA
ACTGAACACAGGCCGGACAGAAGCTTGGAAGGTCCTGTCTCCCCAGGGAGGAGGC
CCCTGGGACAGTGTGGCTCGTGTCCTTCCCAACGGCTCCCTCTTCCTTCCGGCTGTC
GGGATCCAGGATGAGGGGATTTTCCGGTGCCAGGCAATGAACAGGAATGGAAAG
GAGACCAAGTCCAACTACCGAGTCCGTGTCTACCAGATTCCTGGGAAGCCAGAAA
TTGTAGATTCTGCCTCTGAACTCACGGCTGGTGTTCCCAATAAGGTGGGGACATGT
GTGTCAGAGGGAAGCTACCCTGCAGGGACTCTTAGCTGGCACTTGGATGGGAAGC
CCCTGGTGCCTAATGAGAAGGGAGTATCTGTGAAGGAACAGACCAGGAGACACCC
TGAGACAGGGCTCTTCACACTGCAGTCGGAGCTAATGGTGACCCCAGCCCGGGGA
GGAGATCCCCGTCCCACCTTCTCCTGTAGCTTCAGCCCAGGCCTTCCCCGACACTC
CAGCGACAAAACTCACACATGCCCACCGTGCCCAGCACCTGAACTCGCGGGGGCA
CCGTCAGTCTTCCTCTTCCCCCCAAAACCCAAGGACACCCTCATGATCTCCCGGAC
CCCTGAGGTCACATGCGTGGTGGTGGACGTGAGCCACGAAGACCCTGAGGTCAAG
TTCAACTGGTACGTGGACGGCGTGGAGGTGCATAATGCCAAGACAAAGCCGCGGG
AGGAGCAGTACAACAGCACGTACCGTGTGGTCAGCGTCCTCACCGTCCTGCACCA
GGACTGGCTGAATGGCAAGGAGTACAAGTGCAAGGTCTCCAACAAAGCCCTCCCA
GCCCCCATCGAGAAAACCATCTCCAAAGCCAAAGGGCAGCCCCGAGAACCACAG
GTGTACACCCTGCCCCCATCCCGGGATGAGCTGACCAAGAACCAGGTCAGCCTGA
CCTGCCTGGTCAAAGGCTTCTATCCCAGCGACATCGCCGTGGAGTGGGAGAGCAA
TGGGCAGCCGGAGAACAACTACAAGACCACGCCTCCCGTGCTGGACTCCGACGGC
TCCTTCTTCCTCTACAGCAAGCTCACCGTGGACAAGAGCAGGTGGCAGCAGGGGA
ACGTCTTCTCATGCTCCGTGATGCATGAGGCTCTGCACAACCACTACACGCAGAAG
AGCCTCTCCCTGTCTCCGGGTAAAtaatctagagca

FIG. 14A

AVVGAQNITARIGEPLVLKCKGAPKKPPQRLEWKLNTGRTEAWKVLSPQGGGPWDS
VARVLPNGSLFLPAVGIQDEGIFRCQAMNRNGKETKSNYRVRVYQIPGKPEIVDSASE
LTAGVPNKVGTCVSEGSYPAGTLSWHLDGKPLVPNEKGVSVKEQTRRHPETGLFTLQ
SELMVTPARGGDPRPTFSCSFSPGLPRH-
SSDKTHTCPPCPAPE<u>AGA</u>PSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPGK

FIG. 14B 1 mgkgdpkkpr gkmssyaffv qtcreehkkk hpdasvnfse fskkcserwk tmsakekgkf
61 edmakadkar yeremktyip pkgetkkkfk dpnapkrpps afflfcseyr pkikgehpgl
121 sigdvakklg emwnntaadd kqpyekkaak lkekyekdia ayrakgkpda akkgvvkaek
181 skkkkeeeed eedeedeeee edeededeee dddde

FIG. 15A 1 mgkgdpkkpr gkmssyaffv qtcreehkkk hpdasvnfse fskkcserwk tmsakekgkf
61 edmakadkar yeremktyip pkgetkkkfk dpnapkrpps afflfcseyr pkikgehpgl
121 sigdvakklg emwnntaadd kqpyekkaak lkekyekdia ayrakgkpda akkgvvkaek
181 skkkkeeedd eedeedeeee eeeededeee dddde

FIG. 15B 1 pdasvnfsef skkcserwkt msakekgkfe dmakadkary eremktyipp kget

FIG. 15C 1 napkrppsaf flfcseyrpk ikgehpglsi gdvakklgem wnntaaddkq pyekkaaklk
61 ekyekdiaa

FIG. 15D

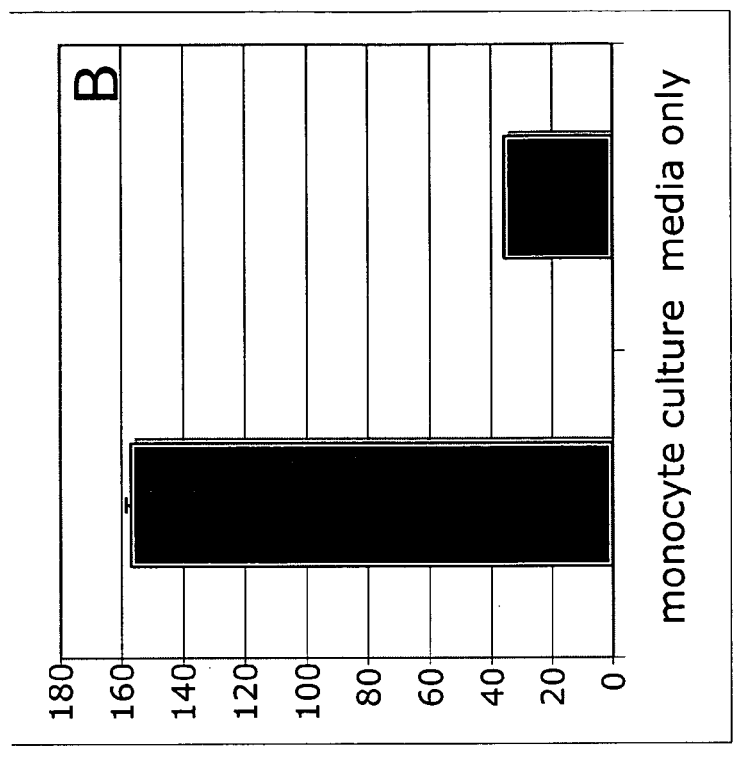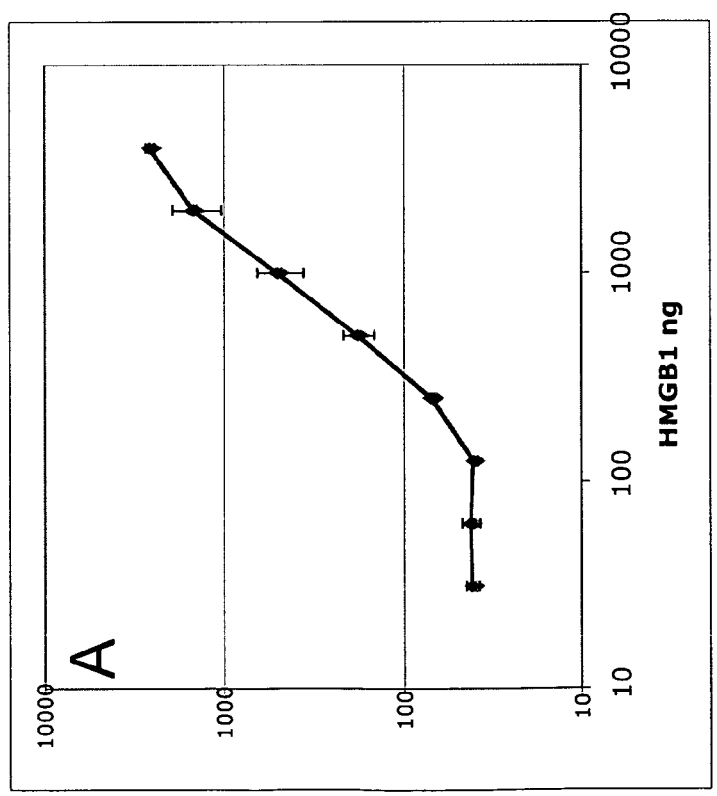
FIG. 16

SEQUENCE LISTING

<160> NUMBER OF SEQ ID NOS: 34

<210> SEQ ID NO 1
<211> LENGTH: 1391
<212> TYPE: DNA
<213> ORGANISM: Homo sapiens

<400> SEQUENCE: 1

```
ggggcagccg gaacagcagt tggagcctgg gtgctggtcc tcagtctgtg gggggcagta      60
gtaggtgctc aaaacatcac agcccggatt ggcgagccac tggtgctgaa gtgtaagggg     120
gcccccaaga aaccaccca gcggctggaa tggaaactga acacaggccg gacagaagct     180
tggaaggtcc tgtctcccca gggaggaggc cctgggaca gtgtggctcg tgtccttccc     240
aacggctccc tcttccttcc ggctgtcggg atccaggatg aggggatttt ccggtgcagg     300
gcaatgaaca ggaatggaaa ggagaccaag tccaactacc gagtccgtgt ctaccagatt     360
cctgggaagc cagaaattgt agattctgcc tctgaactca cggctggtgt tcccaataag     420
gtggggacat gtgtgtcaga gggaagctac cctgcaggga ctcttagctg gcacttggat     480
gggaagcccc tggtgcctaa tgagaaggga gtatctgtga aggaacagac caggagacac     540
cctgagacag ggctcttcac actgcagtcg gagctaatgg tgaccccagc ccggggagga     600
gatccccgtc ccaccttctc ctgtagcttc agcccaggcc ttcccccgaca ccgggccttg     660
cgcacagccc ccatccagcc ccgtgtctgg gagcctgtgc ctctggagga ggtccaattg     720
gtggtggagc cagaaggtgg agcagtagct cctggtggaa ccgtaaccct gacctgtgaa     780
gtccctgccc agccctctcc tcaaatccac tggatgaagg atggtgtgcc cttgcccctt     840
cccccagcc ctgtgctgat cctccctgag atagggcctc aggaccaggg aacctacagc     900
tgtgtggcca cccattccag ccacgggccc aggaaaagcc gtgctgtcag catcagcatc     960
atcgaaccag gcgaggaggg gccaactgca ggctctgtgg gaggatcagg gctgggaact    1020
ctagccctgg ccctggggat cctgggaggc ctgggacag ccgccctgct cattgggtc    1080
atcttgtggc aaaggcggca acgccgagga gaggagagga aggccccaga aaaccaggag    1140
gaagaggagg agcgtgcaga actgaatcag tcggaggaac ctgaggcagg cgagagtagt    1200
actggagggc cttgaggggc ccacagacag atcccatcca tcagctccct tttcttttc    1260
ccttgaactg ttctggcctc agaccaactc tctcctgtat aatctctctc ctgtataacc    1320
ccaccttgcc aagctttctt ctacaaccag agccccccac aatgatgatt aaacacctga    1380
cacatcttgc a                                                         1391
```

<210> SEQ ID NO 2
<211> LENGTH: 404
<212> TYPE: PRT
<213> ORGANISM: Homo sapiens

<400> SEQUENCE: 2

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

-continued

Ser Pro Gln Gly Gly Gly Pro Trp Asp Ser Val Ala Arg Val Leu Pro
 65                  70                  75                  80

Asn Gly Ser Leu Phe Leu Pro Ala Val Gly Ile Gln Asp Glu Gly Ile
                 85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205

Ser Phe Ser Pro Gly Leu Pro Arg His Arg Ala Leu Arg Thr Ala Pro
210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
            260                 265                 270

Lys Asp Gly Val Pro Leu Pro Leu Pro Pro Ser Pro Val Leu Ile Leu
        275                 280                 285

Pro Glu Ile Gly Pro Gln Asp Gln Gly Thr Tyr Ser Cys Val Ala Thr
290                 295                 300

His Ser Ser His Gly Pro Gln Glu Ser Arg Ala Val Ser Ile Ser Ile
305                 310                 315                 320

Ile Glu Pro Gly Glu Gly Pro Thr Ala Gly Ser Val Gly Gly Ser
                325                 330                 335

Gly Leu Gly Thr Leu Ala Leu Ala Leu Gly Ile Leu Gly Gly Leu Gly
            340                 345                 350

Thr Ala Ala Leu Leu Ile Gly Val Ile Leu Trp Gln Arg Arg Gln Arg
        355                 360                 365

Arg Gly Glu Glu Arg Lys Ala Pro Glu Asn Gln Glu Glu Glu Glu Glu
    370                 375                 380

Arg Ala Glu Leu Asn Gln Ser Glu Glu Pro Glu Ala Gly Glu Ser Ser
385                 390                 395                 400

Thr Gly Gly Pro

<210> SEQ ID NO 3
<211> LENGTH: 2009
<212> TYPE: DNA
<213> ORGANISM: Homo sapiens

<400> SEQUENCE: 3
agctttctgg ggcaggccag gcctgacctt ggctttgggg cagggagggg gctaaggtga      60
ggcaggtggc gccagcaggt gcacacccaa tgcccatgag cccagacact ggacgctgaa     120
cctcgcggac agttaagaac ccaggggcct ctgcgcctgg gcccagctct gtcccacacc     180

```
gcggtcacat ggcaccacct ctcttgcagc ctccaccaag ggcccatcgg tcttcccct      240 ggcaccctcc tccaagagca cctctggggg cacagcggcc ctgggctgcc tggtcaagga      300
ctacttcccc gaaccggtga cggtgtcgtg gaactcaggc gccctgacca gcggcgtgca      360
caccttcccg gctgtcctac agtcctcagg actctactcc ctcagcagcg tggtgaccgt      420
gccctccagc agcttgggca cccagaccta catctgcaac gtgaatcaca agcccagcaa      480
caccaaggtg gacaagaaag ttggtgagag gccagcacag ggagggaggg tgtctgctgg      540
aagcaggctc agcgctcctg cctggacgca tcccggctat gcagcccag tccagggcag       600 caaggcaggc cccgtctgcc tcttcacccg gagcctctgc ccgccccact catgctcagg      660
gagagggtct tctggctttt tcccaggctc tgggcaggca caggctaggt gcccctaacc      720
cagggcctgc acacaaaggg gcaggtgctg ggctcagacc tgccaagagc catatccggg      780
aggaccctgc ccctgaccta agcccacccc aaaggccaaa ctctccactc cctcagctcg      840
gacaccttct ctcctcccag attccagtaa ctcccaatct tctctctgca gagcccaaat      900
cttgtgacaa aactcacaca tgcccaccgt gcccaggtaa gccagcccag gcctcgccct      960
ccagctcaag gcgggacagg tgccctagag tagcctgcat ccaggacag gccccagccg      1020 ggtgctgaca cgtccaccctc catctcttcc tcagcacctg aactcctggg gggaccgtca      1080
gtcttcctct tccccccaaa acccaaggac accctcatga tctcccggac ccctgaggtc      1140
acatgcgtgg tggtggacgt gagccacgaa gaccctgagg tcaagttcaa ctggtacgtg      1200 gacggcgtg aggtgcataa tgccaagaca aagccgcggg aggagcagta caacagcacg       1260
taccgggtgg tcagcgtcct caccgtcctg caccaggact ggctgaatgg caaggagtac      1320
aagtgcaagg tctccaacaa agccctccca gcccccatcg agaaaaccat ctccaaagcc      1380
aaaggtggga cccgtggggt gcgagggcca catggacaga ggccggctcg gcccaccctc      1440
tgccctgaga gtgaccgctg taccaacctc tgtcctacag gcagccccg agaaccacag       1500 gtgtacaccc tgcccccatc ccgggatgag ctgaccaaga accaggtcag cctgacctgc      1560
ctggtcaaag gcttctatcc cagcgacatc gccgtggagt gggagagcaa tgggcagccg      1620
gagaacaact acaagaccac gcctcccgtg ctggactccg acggctcctt cttcctctac      1680
agcaagctca ccgtggacaa gagcaggtgg cagcagggga acgtcttctc atgctccgtg      1740
atgcatgagg ctctgcacaa ccactacacg cagaagagcc tctccctgtc tccgggtaaa      1800
tgagtgcgac ggccggcaag ccccgctccc cgggctctcg cggtcgcacg aggatgcttg      1860
gcacgtaccc cctgtacata cttcccgggc gcccagcatg gaaataaagc acccagcgct      1920
gccctgggcc cctgcgagac tgtgatggtt ctttccacgg gtcaggccga gtctgaggcc      1980
tgagtggcat gagggaggca gagcgggtc                                        2009
```

<210> SEQ ID NO 4
<211> LENGTH: 329
<212> TYPE: PRT
<213> ORGANISM: Homo sapiens

<400> SEQUENCE: 4

```
Ser Thr Lys Gly Pro Ser Val Phe Pro Leu Ala Pro Ser Ser Lys Ser
 1               5                   10                  15

Thr Ser Gly Gly Thr Ala Ala Leu Gly Cys Leu Val Lys Asp Tyr Phe
             20                  25                  30

Pro Glu Pro Val Thr Val Ser Trp Asn Ser Gly Ala Leu Thr Ser Gly
         35                  40                  45
```

```
Val His Thr Phe Pro Ala Val Leu Gln Ser Ser Gly Leu Tyr Ser Leu
 50                  55                  60
Ser Ser Val Val Thr Val Pro Ser Ser Ser Leu Gly Thr Gln Thr Tyr
 65                  70                  75                  80
Ile Cys Asn Val Asn His Lys Pro Ser Asn Thr Lys Val Asp Lys Lys
                 85                  90                  95
Val Glu Pro Lys Ser Cys Asp Lys Thr His Thr Cys Pro Pro Cys Pro
            100                 105                 110
Ala Pro Glu Leu Leu Gly Gly Pro Ser Val Phe Leu Phe Pro Pro Lys
        115                 120                 125
Pro Lys Asp Thr Leu Met Ile Ser Arg Thr Pro Glu Val Thr Cys Val
130                 135                 140
Val Val Asp Val Ser His Glu Asp Pro Glu Val Lys Phe Asn Trp Tyr
145                 150                 155                 160
Val Asp Gly Val Glu Val His Asn Ala Lys Thr Lys Pro Arg Glu Glu
                165                 170                 175
Gln Tyr Asn Ser Thr Tyr Arg Val Val Ser Val Leu Thr Val Leu His
            180                 185                 190
Gln Asp Trp Leu Asn Gly Lys Glu Tyr Lys Cys Lys Val Ser Asn Lys
        195                 200                 205
Ala Leu Pro Ala Pro Ile Glu Lys Thr Ile Ser Lys Ala Lys Gly Gln
210                 215                 220
Pro Arg Glu Pro Gln Val Tyr Thr Leu Pro Pro Ser Arg Asp Glu Leu
225                 230                 235                 240
Thr Lys Asn Gln Val Ser Leu Thr Cys Leu Val Lys Gly Phe Tyr Pro
                245                 250                 255
Ser Asp Ile Ala Val Glu Trp Glu Ser Asn Gly Gln Pro Glu Asn Asn
            260                 265                 270
Tyr Lys Thr Thr Pro Pro Val Leu Asp Ser Asp Gly Ser Phe Phe Leu
        275                 280                 285
Tyr Ser Lys Leu Thr Val Asp Lys Ser Arg Trp Gln Gln Gly Asn Val
290                 295                 300
Phe Ser Cys Ser Val Met His Glu Ala Leu His Asn His Tyr Thr Gln
305                 310                 315                 320
Lys Ser Leu Ser Leu Ser Pro Gly Lys
                325

<210> SEQ ID NO 5
<211> LENGTH: 1629
<212> TYPE: DNA
<213> ORGANISM: Artificial Sequence
<220> FEATURE:
<223> OTHER INFORMATION: RAGE-Ig fusion protein

<400> SEQUENCE: 5
ccggaattcc tcaccatggc agccggaaca gcagttggag cctgggtgct ggtcctcagt    60 ctgtggggg cagtagtagg tgctcaaaac atcacagccc ggattggcga gccactggtg   120
ctgaagtgta ggggggcccc caagaaacca ccccagcggc tggaatggaa actgaacaca   180
ggccggacag aagcttggaa ggtcctgtct cccagggag gaggcccctg ggacagtgtg   240
gctcgtgtcc ttcccaacgg ctccctcttc cttccggctg tcgggatcca ggatgagggg   300
attttccggt gccaggcaat gaacaggaat ggaaaggaga ccaagtccaa ctaccgagtc   360
cgtgtctacc agattcctgg gaagccagaa attgtagatt ctgcctctga actcacggct   420
ggtgttccca taaggtggg gacatgtgtg tcagagggaa gctaccctgc aggactctt   480
```

```
agctggcact tggatgggaa gccctgtg cctaatgaga agggagtatc tgtgaaggaa    540
cagaccagga gacaccctga cagggctc ttcacactgc agtcggagct aatggtgacc    600
ccagcccggg gaggagatcc ccgtcccacc ttctcctgta gcttcagccc aggccttccc    660
cgacaccggg ccttgcgcac agcccccatc agccccgtg tctgggagcc tgtgcctctg    720
gaggaggtcc aattggtggt ggagccagaa ggtggagcag tagctcctgg tggaaccgta    780
accctgacct gtgaagtccc tgcccagccc tctcctcaaa tccactggat gaaggatggt    840
gtgcccttgc cccttccccc cagccctgtg ctgatcctcc ctgagatagg gcctcaggac    900
cagggaacct acagctgtgt ggccacccat ccagcgaca aaactcacac atgcccaccg    960
tgcccagcac ctgaactcgc gggggcaccg tcagtcttcc tcttcccccc aaaacccaag   1020
gacaccctca tgatctcccg gacccctgag gtcacatgcg tggtggtgga cgtgagccac   1080
gaagaccctg aggtcaagtt caactggtac gtggacggcg tggaggtgca taatgccaag   1140
acaaagccgc gggaggagca gtacaacagc acgtaccgtg tggtcagcgt cctcaccgtc   1200
ctgcaccagg actggctgaa tggcaaggag tacaagtgca aggtctccaa caaagccctc   1260
ccagccccca tcgagaaaac catctccaaa gccaagggc agccccgaga accacaggtg   1320
tacaccctgc cccatcccg ggatgagctg accaagaacc aggtcagcct gacctgcctg   1380
gtcaaaggct tctatcccag cgacatcgcc gtggagtggg agagcaatgg gcagccggag   1440
aacaactaca agaccacgcc tcccgtgctg gactccgacg gctccttctt cctctacagc   1500
aagctcaccg tggacaagag caggtggcag caggggaacg tcttctcatg ctccgtgatg   1560
catgaggctc tgcacaacca ctacacgcag aagagcctct ccctgtctcc gggtaaataa   1620
tctagagca                                                         1629
```

<210> SEQ ID NO 6
<211> LENGTH: 516
<212> TYPE: PRT
<213> ORGANISM: Artificial Sequence
<220> FEATURE:
<223> OTHER INFORMATION: RAGE-Ig fusion protein

<400> SEQUENCE: 6

```
Ala Val Val Gly Ala Gln Asn Ile Thr Ala Arg Ile Gly Glu Pro Leu
 1               5                  10                  15

Val Leu Lys Cys Lys Gly Ala Pro Lys Lys Pro Pro Gln Arg Leu Glu
            20                  25                  30

Trp Lys Leu Asn Thr Gly Arg Thr Glu Ala Trp Lys Val Leu Ser Pro
        35                  40                  45

Gln Gly Gly Gly Pro Trp Asp Ser Val Ala Arg Val Leu Pro Asn Gly
    50                  55                  60

Ser Leu Phe Leu Pro Ala Val Gly Ile Gln Asp Glu Gly Ile Phe Arg
65                  70                  75                  80

Cys Gln Ala Met Asn Arg Asn Gly Lys Glu Thr Lys Ser Asn Tyr Arg
                85                  90                  95

Val Arg Val Tyr Gln Ile Pro Gly Lys Pro Glu Ile Val Asp Ser Ala
            100                 105                 110

Ser Glu Leu Thr Ala Gly Val Pro Asn Lys Val Gly Thr Cys Val Ser
        115                 120                 125

Glu Gly Ser Tyr Pro Ala Gly Thr Leu Ser Trp His Leu Asp Gly Lys
    130                 135                 140

Pro Leu Val Pro Asn Glu Lys Gly Val Ser Val Lys Glu Gln Thr Arg
145                 150                 155                 160
```

```
Arg His Pro Glu Thr Gly Leu Phe Thr Leu Gln Ser Glu Leu Met Val
            165                 170                 175

Thr Pro Ala Arg Gly Gly Asp Pro Arg Pro Thr Phe Ser Cys Ser Phe
            180                 185                 190

Ser Pro Gly Leu Pro Arg His Arg Ala Leu Arg Thr Ala Pro Ile Gln
        195                 200                 205

Pro Arg Val Trp Glu Pro Val Pro Leu Glu Glu Val Gln Leu Val Val
        210                 215                 220

Glu Pro Glu Gly Gly Ala Val Ala Pro Gly Gly Thr Val Thr Leu Thr
225                 230                 235                 240

Cys Glu Val Pro Ala Gln Pro Ser Pro Gln Ile His Trp Met Lys Asp
                245                 250                 255

Gly Val Pro Leu Pro Leu Pro Pro Ser Pro Val Leu Ile Leu Pro Glu
                260                 265                 270

Ile Gly Pro Gln Asp Gln Gly Thr Tyr Ser Cys Val Ala Thr His Ser
            275                 280                 285

Ser Asp Lys Thr His Thr Cys Pro Pro Cys Pro Ala Pro Glu Leu Ala
        290                 295                 300

Gly Ala Pro Ser Val Phe Leu Phe Pro Pro Lys Pro Lys Asp Thr Leu
305                 310                 315                 320

Met Ile Ser Arg Thr Pro Glu Val Thr Cys Val Val Val Asp Val Ser
                325                 330                 335

His Glu Asp Pro Glu Val Lys Phe Asn Trp Tyr Val Asp Gly Val Glu
                340                 345                 350

Val His Asn Ala Lys Thr Lys Pro Arg Glu Glu Gln Tyr Asn Ser Thr
            355                 360                 365

Tyr Arg Val Val Ser Val Leu Thr Val Leu His Gln Asp Trp Leu Asn
        370                 375                 380

Gly Lys Glu Tyr Lys Cys Lys Val Ser Asn Lys Ala Leu Pro Ala Pro
385                 390                 395                 400

Ile Glu Lys Thr Ile Ser Lys Ala Lys Gly Gln Pro Arg Glu Pro Gln
                405                 410                 415

Val Tyr Thr Leu Pro Pro Ser Arg Asp Glu Leu Thr Lys Asn Gln Val
            420                 425                 430

Ser Leu Thr Cys Leu Val Lys Gly Phe Tyr Pro Ser Asp Ile Ala Val
        435                 440                 445

Glu Trp Glu Ser Asn Gly Gln Pro Glu Asn Asn Tyr Lys Thr Thr Pro
        450                 455                 460

Pro Val Leu Asp Ser Asp Gly Ser Phe Phe Leu Tyr Ser Lys Leu Thr
465                 470                 475                 480

Val Asp Lys Ser Arg Trp Gln Gln Gly Asn Val Phe Ser Cys Ser Val
                485                 490                 495

Met His Glu Ala Leu His Asn His Tyr Thr Gln Lys Ser Leu Ser Leu
            500                 505                 510

Ser Pro Gly Lys
        515

<210> SEQ ID NO 7
<211> LENGTH: 1044
<212> TYPE: DNA
<213> ORGANISM: Artificial Sequence
<220> FEATURE:
<223> OTHER INFORMATION: 1-domain RAGE-Ig fusion protein
```

-continued

```
<400> SEQUENCE: 7
ccggaattcc tcaccatggc agccggaaca gcagttggag cctgggtgct ggtcctcagt      60
ctgtgggggg cagtagtagg tgctcaaaac atcacagccc ggattggcga gccactggtg     120
ctgaagtgta aggggccccc aagaaaacca ccccagcggc tggaatggaa actgaacaca     180
ggccggacag aagcttggaa ggtcctgtct ccccagggag gaggcccctg ggacagtgtg     240
gctcgtgtcc ttcccaacgg ctccctcttc cttccggctg tcgggatcca ggatgagggg     300
attttccggt gccaggcaat gaacaggaat ggaaaggaga ccaagtccag cgacaaaact     360
cacacatgcc caccgtgccc agcacctgaa ctcgcggggg caccgtcagt cttcctcttc     420
cccccaaaac ccaaggacac cctcatgatc tcccggaccc ctgaggtcac atgcgtggtg     480
gtggacgtga gccacgaaga ccctgaggtc aagttcaact ggtacgtgga cggcgtggag     540
gtgcataatg ccaagacaaa gccgcgggag gagcagtaca acagcacgta ccgtgtggtc     600
agcgtcctca ccgtcctgca ccaggactgg ctgaatggca aggagtacaa gtgcaaggtc     660
tccaacaaag ccctcccagc ccccatcgag aaaaccatct ccaaagccaa agggcagccc     720
cgagaaccac aggtgtacac cctgccccca tcccgggatg agctgaccaa gaaccaggtc     780
agcctgacct gcctggtcaa aggcttctat cccagcgaca tcgccgtgga gtgggagagc     840
aatgggcagc cggagaacaa ctacaagacc acgcctcccg tgctggactc cgacggctcc     900
ttcttcctct acagcaagct caccgtggac aagagcaggt ggcagcaggg gaacgtcttc     960
tcatgctccg tgatgcatga ggctctgcac aaccactaca cgcagaagag cctctccctg    1020
tctccgggta ataatctag agca                                             1044

<210> SEQ ID NO 8
<211> LENGTH: 321
<212> TYPE: PRT
<213> ORGANISM: Artificial Sequence
<220> FEATURE:
<223> OTHER INFORMATION: 1-domain RAGE-Ig fusion protein

<400> SEQUENCE: 8

Ala Val Val Gly Ala Gln Asn Ile Thr Ala Arg Ile Gly Glu Pro Leu
  1               5                  10                  15

Val Leu Lys Cys Lys Gly Ala Pro Lys Lys Pro Pro Gln Arg Leu Glu
             20                  25                  30

Trp Lys Leu Asn Thr Gly Arg Thr Glu Ala Trp Lys Val Leu Ser Pro
         35                  40                  45

Gln Gly Gly Gly Pro Trp Asp Ser Val Ala Arg Val Leu Pro Asn Gly
     50                  55                  60

Ser Leu Phe Leu Pro Ala Val Gly Ile Gln Asp Glu Gly Ile Phe Arg
 65                  70                  75                  80

Cys Gln Ala Met Asn Arg Asn Gly Lys Glu Thr Lys Ser Ser Asp Lys
                 85                  90                  95

Thr His Thr Cys Pro Pro Cys Pro Ala Pro Glu Leu Ala Gly Ala Pro
            100                 105                 110

Ser Val Phe Leu Phe Pro Pro Lys Pro Lys Asp Thr Leu Met Ile Ser
        115                 120                 125

Arg Thr Pro Glu Val Thr Cys Val Val Val Asp Val Ser His Glu Asp
    130                 135                 140

Pro Glu Val Lys Phe Asn Trp Tyr Val Asp Gly Val Glu Val His Asn
145                 150                 155                 160
```

```
Ala Lys Thr Lys Pro Arg Glu Glu Gln Tyr Asn Ser Thr Tyr Arg Val
            165                 170                 175

Val Ser Val Leu Thr Val Leu His Gln Asp Trp Leu Asn Gly Lys Glu
            180                 185                 190

Tyr Lys Cys Lys Val Ser Asn Lys Ala Leu Pro Ala Pro Ile Glu Lys
            195                 200                 205

Thr Ile Ser Lys Ala Lys Gly Gln Pro Arg Glu Pro Gln Val Tyr Thr
            210                 215                 220

Leu Pro Pro Ser Arg Asp Glu Leu Thr Lys Asn Gln Val Ser Leu Thr
225                 230                 235                 240

Cys Leu Val Lys Gly Phe Tyr Pro Ser Asp Ile Ala Val Glu Trp Glu
            245                 250                 255

Ser Asn Gly Gln Pro Glu Asn Asn Tyr Lys Thr Thr Pro Pro Val Leu
            260                 265                 270

Asp Ser Asp Gly Ser Phe Phe Leu Tyr Ser Lys Leu Thr Val Asp Lys
            275                 280                 285

Ser Arg Trp Gln Gln Gly Asn Val Phe Ser Cys Ser Val Met His Glu
            290                 295                 300

Ala Leu His Asn His Tyr Thr Gln Lys Ser Leu Ser Leu Ser Pro Gly
305                 310                 315                 320

Lys

<210> SEQ ID NO 9
<211> LENGTH: 1365
<212> TYPE: DNA
<213> ORGANISM: Artificial Sequence
<220> FEATURE:
<223> OTHER INFORMATION: 2-domain RAGE-Ig fusion protein

<400> SEQUENCE: 9
ccggaattcc tcaccatggc agccggaaca gcagttggag cctgggtgct ggtcctcagt      60
ctgtgggggg cagtagtagg tgctcaaaac atcacagccc ggattggcga gccactggtg     120
ctgaagtgta aggggccccc caagaaacca cccagcggc tggaatggaa actgaacaca      180
ggccggacag aagcttggaa ggtcctgtct ccccaggag gaggcccctg gacagtgtg       240 gctcgtgtcc ttcccaacgg ctccctcttc cttccggctg tcgggatcca ggatgagggg     300
attttccggt gccaggcaat gaacaggaat ggaaaggaga ccaagtccaa ctaccgagtc     360
cgtgtctacc agattcctgg gaagccagaa attgtagatt ctgcctctga actcacggct     420
ggtgttccca ataaggtggg gacatgtgtg tcagagggaa gctaccctgc agggactctt     480
agctggcact ggatgggaa gcccctggtg cctaatgaga agggagtatc tgtgaaggaa      540
cagaccagga gacaccctga caggggctc ttcacactgc agtcggagct aatggtgacc      600
ccagcccggg aggagatcc ccgtcccacc ttctcctgta gcttcagccc aggccttccc     660
cgacactcca gcgacaaaac tcacacatgc ccaccgtgcc cagcacctga actcgcgggg     720
gcaccgtcag tcttcctctt ccccccaaaa cccaaggaca ccctcatgat ctcccggacc     780
cctgaggtca catgcgtggt ggtggacgtg agccacgaag accctgaggt caagttcaac     840
tggtacgtgg acggcgtgga ggtgcataat gccaagacaa agccgcggga ggagcagtac     900
aacagcacgt accgtgtggt cagcgtcctc accgtcctgc accaggactg gctgaatggc     960
aaggagtaca agtgcaaggt ctccaacaaa gccctcccag cccccatcga gaaaaccatc    1020
tccaaagcca agggcagccc cgagaaccca caggtgtaca ccctgccccc atcccgggat    1080
gagctgacca agaaccaggt cagcctgacc tgcctggtca aaggcttcta tcccagcgac    1140
```

-continued

```
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaataatcta gagca                   1365
```

<210> SEQ ID NO 10
<211> LENGTH: 428
<212> TYPE: PRT
<213> ORGANISM: Artificial Sequence
<220> FEATURE:
<223> OTHER INFORMATION: 2-domain RAGE-Ig fusion protein

<400> SEQUENCE: 10

```
Ala Val Val Gly Ala Gln Asn Ile Thr Ala Arg Ile Gly Glu Pro Leu
  1               5                  10                  15

Val Leu Lys Cys Lys Gly Ala Pro Lys Lys Pro Pro Gln Arg Leu Glu
             20                  25                  30

Trp Lys Leu Asn Thr Gly Arg Thr Glu Ala Trp Lys Val Leu Ser Pro
         35                  40                  45

Gln Gly Gly Gly Pro Trp Asp Ser Val Ala Arg Val Leu Pro Asn Gly
     50                  55                  60

Ser Leu Phe Leu Pro Ala Val Gly Ile Gln Asp Glu Gly Ile Phe Arg
 65                  70                  75                  80

Cys Gln Ala Met Asn Arg Asn Gly Lys Glu Thr Lys Ser Asn Tyr Arg
                 85                  90                  95

Val Arg Val Tyr Gln Ile Pro Gly Lys Pro Glu Ile Val Asp Ser Ala
            100                 105                 110

Ser Glu Leu Thr Ala Gly Val Pro Asn Lys Val Gly Thr Cys Val Ser
        115                 120                 125

Glu Gly Ser Tyr Pro Ala Gly Thr Leu Ser Trp His Leu Asp Gly Lys
    130                 135                 140

Pro Leu Val Pro Asn Glu Lys Gly Val Ser Val Lys Glu Gln Thr Arg
145                 150                 155                 160

Arg His Pro Glu Thr Gly Leu Phe Thr Leu Gln Ser Glu Leu Met Val
                165                 170                 175

Thr Pro Ala Arg Gly Gly Asp Pro Arg Pro Thr Phe Ser Cys Ser Phe
            180                 185                 190

Ser Pro Gly Leu Pro Arg His Ser Ser Asp Lys Thr His Thr Cys Pro
        195                 200                 205

Pro Cys Pro Ala Pro Glu Leu Ala Gly Ala Pro Ser Val Phe Leu Phe
    210                 215                 220

Pro Pro Lys Pro Lys Asp Thr Leu Met Ile Ser Arg Thr Pro Glu Val
225                 230                 235                 240

Thr Cys Val Val Val Asp Val Ser His Glu Asp Pro Glu Val Lys Phe
                245                 250                 255

Asn Trp Tyr Val Asp Gly Val Glu Val His Asn Ala Lys Thr Lys Pro
            260                 265                 270

Arg Glu Glu Gln Tyr Asn Ser Thr Tyr Arg Val Val Ser Val Leu Thr
        275                 280                 285

Val Leu His Gln Asp Trp Leu Asn Gly Lys Glu Tyr Lys Cys Lys Val
    290                 295                 300

Ser Asn Lys Ala Leu Pro Ala Pro Ile Glu Lys Thr Ile Ser Lys Ala
305                 310                 315                 320
```

```
Lys Gly Gln Pro Arg Glu Pro Gln Val Tyr Thr Leu Pro Pro Ser Arg
                325                 330                 335

Asp Glu Leu Thr Lys Asn Gln Val Ser Leu Thr Cys Leu Val Lys Gly
            340                 345                 350

Phe Tyr Pro Ser Asp Ile Ala Val Glu Trp Glu Ser Asn Gly Gln Pro
        355                 360                 365

Glu Asn Asn Tyr Lys Thr Thr Pro Pro Val Leu Asp Ser Asp Gly Ser
370                 375                 380

Phe Phe Leu Tyr Ser Lys Leu Thr Val Asp Lys Ser Arg Trp Gln Gln
385                 390                 395                 400

Gly Asn Val Phe Ser Cys Ser Val Met His Glu Ala Leu His Asn His
                405                 410                 415

Tyr Thr Gln Lys Ser Leu Ser Leu Ser Pro Gly Lys
            420                 425
```

<210> SEQ ID NO 11
<211> LENGTH: 215
<212> TYPE: PRT
<213> ORGANISM: Homo sapiens

<400> SEQUENCE: 11

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Lys Glu Glu Glu Glu Asp Glu Glu
            180                 185                 190

Asp Glu Glu Asp Glu Glu Glu Glu Asp Glu Glu Asp Glu Glu Asp Glu
        195                 200                 205

Glu Glu Asp Asp Asp Asp Glu
    210                 215
```

<210> SEQ ID NO 12
<211> LENGTH: 215
<212> TYPE: PRT
<213> ORGANISM: Mus musculus

<400> SEQUENCE: 12

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Asp Glu Glu
            180                 185                 190

Asp Glu Glu Asp Glu Glu Glu Glu Glu Glu Asp Glu Asp Glu
        195                 200                 205

Glu Glu Asp Asp Asp Asp Glu
        210                 215

<210> SEQ ID NO 13
<211> LENGTH: 54
<212> TYPE: PRT
<213> ORGANISM: Homo sapiens

<400> SEQUENCE: 13

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 14
<211> LENGTH: 69
<212> TYPE: PRT
<213> ORGANISM: Homo sapiens

<400> SEQUENCE: 14

Asn Ala Pro Lys Arg Pro Pro Ser Ala Phe Phe Leu Phe Cys Ser Glu
1               5                   10                  15

Tyr Arg Pro Lys Ile Lys Gly Glu His Pro Gly Leu Ser Ile Gly Asp
            20                  25                  30

```
Val Ala Lys Lys Leu Gly Glu Met Trp Asn Asn Thr Ala Ala Asp Asp
    35                  40                  45

Lys Gln Pro Tyr Glu Lys Lys Ala Ala Lys Leu Lys Glu Lys Tyr Glu
    50                  55                  60

Lys Asp Ile Ala Ala
65

<210> SEQ ID NO 15
<211> LENGTH: 89
<212> TYPE: DNA
<213> ORGANISM: Artificial Sequence
<220> FEATURE:
<223> OTHER INFORMATION: Oligonucleotide primer

<400> SEQUENCE: 15
cggccggcaa gccccgctc cccgggctct cgcggtcgca cgaggatgct tggcacgtac      60
cccctgtaca tacttcccgg gcgcccagc                                       89

<210> SEQ ID NO 16
<211> LENGTH: 80
<212> TYPE: DNA
<213> ORGANISM: Artificial Sequence
<220> FEATURE:
<223> OTHER INFORMATION: Oligonucleotide primer

<400> SEQUENCE: 16
aagaaccatc acagtctcgc aggggcccag ggcacggctg ggtgctttat ttccatgctg      60
ggcgcccggg aagtatgtac                                                 80

<210> SEQ ID NO 17
<211> LENGTH: 43
<212> TYPE: DNA
<213> ORGANISM: Artificial Sequence
<220> FEATURE:
<223> OTHER INFORMATION: Oligonucleotide primer

<400> SEQUENCE: 17
gctctagagt gcgacggccg gcaagccccc gctccccggg ctc                       43

<210> SEQ ID NO 18
<211> LENGTH: 50
<212> TYPE: DNA
<213> ORGANISM: Artificial Sequence
<220> FEATURE:
<223> OTHER INFORMATION: Oligonucleotide primer

<400> SEQUENCE: 18
atagtttagc ggccgcctga cccgtggaaa gaaccatcac agtctcgcag                50

<210> SEQ ID NO 19
<211> LENGTH: 187
<212> TYPE: DNA
<213> ORGANISM: Artificial Sequence
<220> FEATURE:
<223> OTHER INFORMATION: IgG1 Heavy-Chain Gene Polyadenylation Signal
      Sequence 1

<400> SEQUENCE: 19
gctctagagt gcgacggccg gcaagccccc gctccccggg ctctcgcggt cgcacgagga      60
tgcttggcac gtaccccctg tacatacttc ccgggcgccc agcatggaaa taaagcaccc     120
agcgctgccc tgggccctg cgagactgtg atggttcttt ccacgggtca ggcggccgct     180
aaactat                                                              187
```

<210> SEQ ID NO 20
<211> LENGTH: 77
<212> TYPE: DNA
<213> ORGANISM: Artificial Sequence
<220> FEATURE:
<223> OTHER INFORMATION: Oligonucleotide primer

<400> SEQUENCE: 20
gtggcatgag ggaggcagag cgggtcccac tgtccccaca ctggcccagg ctgtgcaggt    60
gtgcctgggc cccctag                                                  77

<210> SEQ ID NO 21
<211> LENGTH: 89
<212> TYPE: DNA
<213> ORGANISM: Artificial Sequence
<220> FEATURE:
<223> OTHER INFORMATION: Oligonucleotide primer

<400> SEQUENCE: 21
gggagggcca cgctggcaaa tcccccaccc tgccgagggc agcccctggc tgagccccac    60 cctaggggc ccaggcacac ctgcacagc                                      89

<210> SEQ ID NO 22
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 22
ggccgagtct gaggcctgag tggcatgagg gaggcagagc                          40

<210> SEQ ID NO 23
<211> LENGTH: 55
<212> TYPE: DNA
<213> ORGANISM: Artificial Sequence
<220> FEATURE:
<223> OTHER INFORMATION: Oligonucleotide primer

<400> SEQUENCE: 23
gccactcagg cctcagactc ggcctgaccc gtggaaagaa ccatcacagt ctcgc         55

<210> SEQ ID NO 24
<211> LENGTH: 43
<212> TYPE: DNA
<213> ORGANISM: Artificial Sequence
<220> FEATURE:
<223> OTHER INFORMATION: Oligonucleotide primer

<400> SEQUENCE: 24
atagtttagc ggccgctgga gggagggcca cgctggcaaa tcc                      43

<210> SEQ ID NO 25
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 25
ccggaattcc tcaccatggc agccggaaca gcagttggag                          40

```
<210> SEQ ID NO 26
<211> LENGTH: 52
<212> TYPE: DNA
<213> ORGANISM: Artificial Sequence
<220> FEATURE:
<223> OTHER INFORMATION: Oligonucleotide primer

<400> SEQUENCE: 26
gttttgtcgc tggaatgggt ggccacacag ctgtaggttc cctggtcctg ag          52

<210> SEQ ID NO 27
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 27
gctgtgtggc cacccattcc agcgacaaaa ctcacacatg cccaccgtgc ccagcacctg   60

<210> SEQ ID NO 28
<211> LENGTH: 76
<212> TYPE: DNA
<213> ORGANISM: Artificial Sequence
<220> FEATURE:
<223> OTHER INFORMATION: Oligonucleotide primer

<400> SEQUENCE: 28
tgctctagat tatttacccg gagacaggga gaggccttct gcgtgtagtg gttgtgcaga   60
gcctcatgca tcacgg                                                   76

<210> SEQ ID NO 29
<211> LENGTH: 53
<212> TYPE: DNA
<213> ORGANISM: Artificial Sequence
<220> FEATURE:
<223> OTHER INFORMATION: Oligonucleotide primer

<400> SEQUENCE: 29
gttttgtcgc tggacttggt ctcctttcca ttcctgttca ttgcctggca ccg          53

<210> SEQ ID NO 30
<220> FEATURE:
<223> OTHER INFORMATION: Oligonucleotide primer

<400> SEQUENCE: 30

000

<210> SEQ ID NO 31
<211> LENGTH: 61
<212> TYPE: DNA
<213> ORGANISM: Artificial Sequence
<220> FEATURE:
<223> OTHER INFORMATION: Oligonucleotide primer

<400> SEQUENCE: 31
cggtgggcat gtgtgagttt tgtcgctgga gtgtcgggga aggcctgggc tgaagctaca   60
g                                                                   61

<210> SEQ ID NO 32
<211> LENGTH: 44
<212> TYPE: DNA
<213> ORGANISM: Artificial Sequence
<220> FEATURE:
<223> OTHER INFORMATION: Oligonucleotide primer
```

```
<400> SEQUENCE: 32
ctccagcgac aaaactcaca catgcccacc gtgcccagca cctg            44

<210> SEQ ID NO 33
<211> LENGTH: 77
<212> TYPE: DNA
<213> ORGANISM: Artificial Sequence
<220> FEATURE:
<223> OTHER INFORMATION: Oligonucleotide primer

<400> SEQUENCE: 33
tgctctagat tatttacccg gagacaggga gaggctcttc tgcgtgtagt ggttgtgcag    60
agcctcatgc atcacgg                                                  77

<210> SEQ ID NO 34
<211> LENGTH: 347
<212> TYPE: DNA
<213> ORGANISM: Artificial Sequence
<220> FEATURE:
<223> OTHER INFORMATION: IgG1 Heavy-Chain Gene Polyadenylation Signal
      Sequence 2

<400> SEQUENCE: 34
gctctagagt gcgacggccg gcaagccccc gctccccggg ctctcgcggt cgcacgagga    60
tgcttggcac gtacccctg tacatacttc ccgggcgccc agcatggaaa taaagcaccc   120
agcgctgccc tgggcccctg cgagactgtg atggttcttt ccacgggtca ggccgagtct   180
gaggcctgag tggcatgagg gaggcagagc gggtcccact gtccccacac tggcccaggc   240
tgtgcaggtg tgcctgggcc ccctagggtg gggctcagcc aggggctgcc ctcggcaggg   300
tgggggattt gccagcgtgg ccctccctcc agcggccgct aaactat                 347
```

US 7,470,521 B2

RAGE PROTEIN DERIVATIVES

RELATED APPLICATION

This application claims the benefit of U.S. Provisional Application No. 60/589,678, filed on Jul. 20, 2004, the entire teachings of which are incorporated herein by reference.

BACKGROUND OF THE INVENTION

The pattern recognition receptor, RAGE (Receptor for Advanced Glycation Endproducts) is a multiligand receptor that is a member of the immunoglobulin (Ig) superfamily. RAGE binds AGEs and other ligands, including high mobility group box 1 (HMGB1, also known as HMG-1, HMG1 and amphoterin), amyloid β-peptide, S100/calgranulin family proteins and leukocyte integrins (e.g., Mac-1) (Schmidt, A. et al., *J. Clin. Invest.* 108:949-955 (2001); Chavakis, T. et al., *J. Exp. Med.* 198:1507-1515 (2003)). RAGE is expressed at low levels in normal tissues and vasculature, but becomes upregulated when its ligands accumulate (Schmidt, A. et al., *J. Clin. Invest.* 108:949-955 (2001)). Binding of ligands to RAGE initiates a sustained period of cellular activation that is mediated by receptor-dependent signaling. In addition, the upregulation and enhanced surface expression of RAGE in environments rich in RAGE ligands allows the receptor to propagate cellular dysfunction in a number of pathophysiological conditions, such as diabetes, amyloidoses, immune and inflammatory disorders, and tumors (Schmidt, A. et al., id.).

An important ligand for RAGE is HMGB1, which has been implicated as a cytokine mediator of a number of inflammatory conditions. Inflammation is often induced by proinflammatory cytokines, such as tumor necrosis factor (TNF), interleukin (IL)-1α; IL-1β, IL-6, macrophage migration inhibitory factor (MIF), and other compounds. These proinflammatory cytokines are produced by several different cell types, including immune cells (for example, monocytes, macrophages and neutrophils), as well as non-immune cells, such as fibroblasts, osteoblasts, smooth muscle cells, epithelial cells, and neurons. These proinflammatory cytokines contribute to various disorders during the early stages of an inflammatory cytokine cascade.

The early proinflammatory cytokines (e.g., TNF, IL-1α, IL-1β, IL-6, MIF, etc.) mediate inflammation, and induce the late release of HMGB1, a protein that accumulates in serum and mediates delayed lethality and further induction of early proinflammatory cytokines. The HMGB1 molecule has three domains: two DNA binding motifs termed HMGB A and HMGB B boxes, and an acidic carboxyl terminus. The two HMGB boxes are highly conserved 80 amino acid, L-shaped domains.

Given the importance of RAGE and its ligands (e.g., HMGB1) in a number of significant human disorders (e.g., diabetes, cancer, chronic inflammatory diseases, diabetes, amyloidoses, cardiovascular diseases and other inflammatory diseases), it would be beneficial to identify agents that could be useful for treating disorders mediated by RAGE and its ligands.

SUMMARY OF THE INVENTION

In one embodiment, the present invention is a fusion protein comprising a fragment of the extracellular domain of a Receptor for Advanced Glycation End Product (RAGE) and an immunoglobulin element ("a RAGE-Ig fusion protein"; also referred to herein as "an fRAGE-Ig"). In another embodiment, the invention is a pharmaceutical composition comprising a RAGE-Ig fusion protein. In other embodiments, the invention is a nucleic acid encoding a RAGE-Ig fusion protein, an expression vector comprising a nucleic acid encoding a RAGE-Ig fusion protein, a cell that is transfected with an expression vector comprising a nucleic acid encoding a RAGE-Ig fusion protein and a method of producing a RAGE-Ig fusion protein. In still other embodiments, the invention is a method of treating a condition characterized by activation of an inflammatory cytokine cascade in a subject, comprising administering to the subject a RAGE-Ig fusion protein and/or a pharmaceutical composition comprising a RAGE-Ig fusion protein.

In one embodiment, the invention is a fusion protein comprising at least a first and a second polypeptide, wherein the first polypeptide comprises a fragment of the extracellular domain of a RAGE and the second polypeptide comprises an immunoglobulin element.

In another embodiment, the invention is a pharmaceutical composition comprising a RAGE-Ig fusion protein in a pharmaceutically-acceptable excipient.

In other embodiments, the invention is a nucleic acid encoding a RAGE-Ig fusion protein, an expression vector comprising a nucleic encoding a RAGE-Ig fusion protein, and a cell (e.g., a host cell) that is transfected with an expression vector comprising a nucleic acid encoding a RAGE-Ig fusion protein.

In another embodiment, the invention is a method of producing a RAGE-Ig fusion protein comprising culturing a cell that is transfected with an expression vector, wherein the expression vector comprises a nucleic acid that encodes a RAGE-Ig fusion protein.

In another embodiment, the invention is a method of treating a condition characterized by activation of an inflammatory cytokine cascade in a subject, comprising administering to the subject a RAGE-Ig fusion protein.

In another embodiment, the invention is a method of treating a condition characterized by activation of an inflammatory cytokine cascade in a subject, comprising administering to the subject a pharmaceutical composition that comprises a RAGE-Ig fusion protein and a pharmaceutically-acceptable excipient.

BRIEF DESCRIPTION OF THE DRAWINGS

FIG. 1A is the nucleotide sequence of a human RAGE (GenBank Accession No. M91211; SEQ ID NO:1).

FIG. 1B is an amino acid sequence of a human RAGE (GenBank Accession No. NP_001127; SEQ ID NO:2).

FIG. 2A is the nucleotide sequence of a human IgG1 (GenBank Accession No. J00228; SEQ ID NO:3).

FIG. 2B is the corresponding amino acid sequence (GenBank Accession No. J00228; SEQ ID NO:4) of the human IgG1 encoded by the nucleotide sequence depicted in FIG. 2A.

FIG. 3A is a cDNA sequence of a RAGE-Ig fusion protein (SEQ ID NO:5). The first sequence depicted in lower case contains s restriction enzyme site and a Kozak sequence.

FIG. 3B is the corresponding amino acid sequence (SEQ ID NO:6) of the RAGE-Ig fusion protein encoded by the nucleotide sequence depicted in FIG. 3A. The hyphen indicates the separation between the RAGE portion and Ig portion of the respective polypeptides. The mutated Fc region is underlined and indicates the L117A and G119A mutations).

FIGS. 7A and 7B are graphs depicting ELISA results, which demonstrate that RAGE-Ig fusion proteins bind to both the A box and B box of HMGB1 in a dose-dependent manner. FIG. 7A depicts the binding results for the above-described RAGE-Ig fusion protein (labeled "CTI RAGE-Ig") with the A box of HMGB1 (labeled "A-box CTI RAGE") and the B box of HMGB1 (labeled "B-box CTI RAGE"). FIG. 7B depicts the binding results for the commercially-available recombinant human RAGE/Fc chimera (labeled "R&D RAGE-Ig"; R&D Systems, Inc., Minneapolis, Minn.) with the A box of HMGB1 (labeled "A-box R&D RAGE") and the B box of HMGB1 (labeled "B-box R&D RAGE").

FIG. 8 depicts the TNF-α concentration (Y axis; in pg/ml) from harvested cell supernatants of B10.A cells incubated with various concentrations (X axis; in nM) of HMGB1 alone (labeled "HMGB1 Cntrl (CTI#030-43)"), RAGE-Ig fusion protein alone (labeled "RAGE-Ig (w/out HMGB1)") or a combination of HMGB1 and RAGE-Ig fusion protein (labeled "RAGE-Ig (w/HMGB1)").

FIG. 9 depicts the TNF concentration (Y axis in pg/ml) from harvested cell supernatants of BALB/c bone marrow cells incubated with various concentrations (X axis; in nM) of HMGB1 alone (labeled "HMGB1 only"), RAGE-Ig fusion protein alone (labeled "RAGE-Ig (w/out HMGB1)") or a combination of HMGB1 and RAGE-Ig fusion protein (labeled "RAGE-Ig (w/HMGB1)").

FIGS. 10A-10C show that RAGE-Ig fusion protein binds to the HMG1 A box between amino acids 31-78 and binds to the HMGB1 B box between amino acids 121-158.

FIG. 11 depicts the IL-6 concentration (Y axis; in pg/ml) from harvested cell supernatants of PBMCs incubated with various concentrations (X axis; in ng/ml) of HMGB1 alone (labeled "HMGB1 only"), HMGB1 and RAGE-Ig fusion protein (labeled "HMGB1+RAGE-fusion"), or HMGB1 and 6E6 HMGB1 mAb (labeled "HMGB1+6E6").

FIG. 12 depicts the IL-10 concentration (Y axis; in pg/ml) from harvested cell supernatants of PBMCs incubated with various concentrations (X axis; in ng/ml) of HMGB1 alone (labeled "HMGB1 only"), HMGB1 and RAGE-Ig fusion protein (labeled "HMGB1+RAGE-fusion"), or HMGB1 and 6E6 HMGB1 mAb (labeled "HMGB1+6E6").

FIG. 13A is a cDNA sequence of a 1-domain RAGE-Ig fusion protein (SEQ ID NO:7). The sequences in lower case contain the restriction enzyme sites and Kozak sequences.

FIG. 13B is the corresponding amino acid sequence (SEQ ID NO:8) of the 1-domain RAGE-Ig fusion protein encoded by the nucleotide sequence depicted in FIG. 13A. The hyphen indicates the separation between the RAGE and Ig portions of the protein; the mutated Fc region is underlined.

FIG. 14A is a cDNA sequence of a 2-domain RAGE-Ig fusion protein (SEQ ID NO:9). The sequences in lower case contain the restriction enzyme sites and Kozak sequences.

FIG. 14B is the corresponding amino acid sequence (SEQ ID NO:10) of the 2-domain RAGE-Ig fusion protein encoded by the nucleotide sequence depicted in FIG. 14A. The hyphen indicates the separation between the RAGE and Ig portions of the protein; the mutated Fc region is underlined.

FIG. 15A is the amino acid sequence of a human HMG1 polypeptide (SEQ ID NO:11).

FIG. 15B is the amino acid sequence of a rat and mouse HMG1 polypeptide (SEQ ID NO:12).

FIG. 15C is the amino acid sequence of a human, mouse, and rat HMG1 A box polypeptide (SEQ ID NO:13).

FIG. 15D is the amino acid sequence of a human, mouse, and rat HMG1 B box polypeptide (SEQ ID NO:14).

FIG. 16A is a graph showing that RAGE-Ig bound recombinant HMGB 1. RAGE-bound HMGB1 was detected using mouse anti-HMGB1 mAb 10D4 and binding was measured on a plate reader manufactured by Meso Scale Discovery (Gaithersburg, Md.).

FIG. 16B is a bar graph showing that RAGE-Ig bound HMGB1 produced in monocyte cultures. HMGB1 was detected using mouse anti-HMGB1 mAb 10D4.

DETAILED DESCRIPTION OF THE INVENTION

Figure 4:
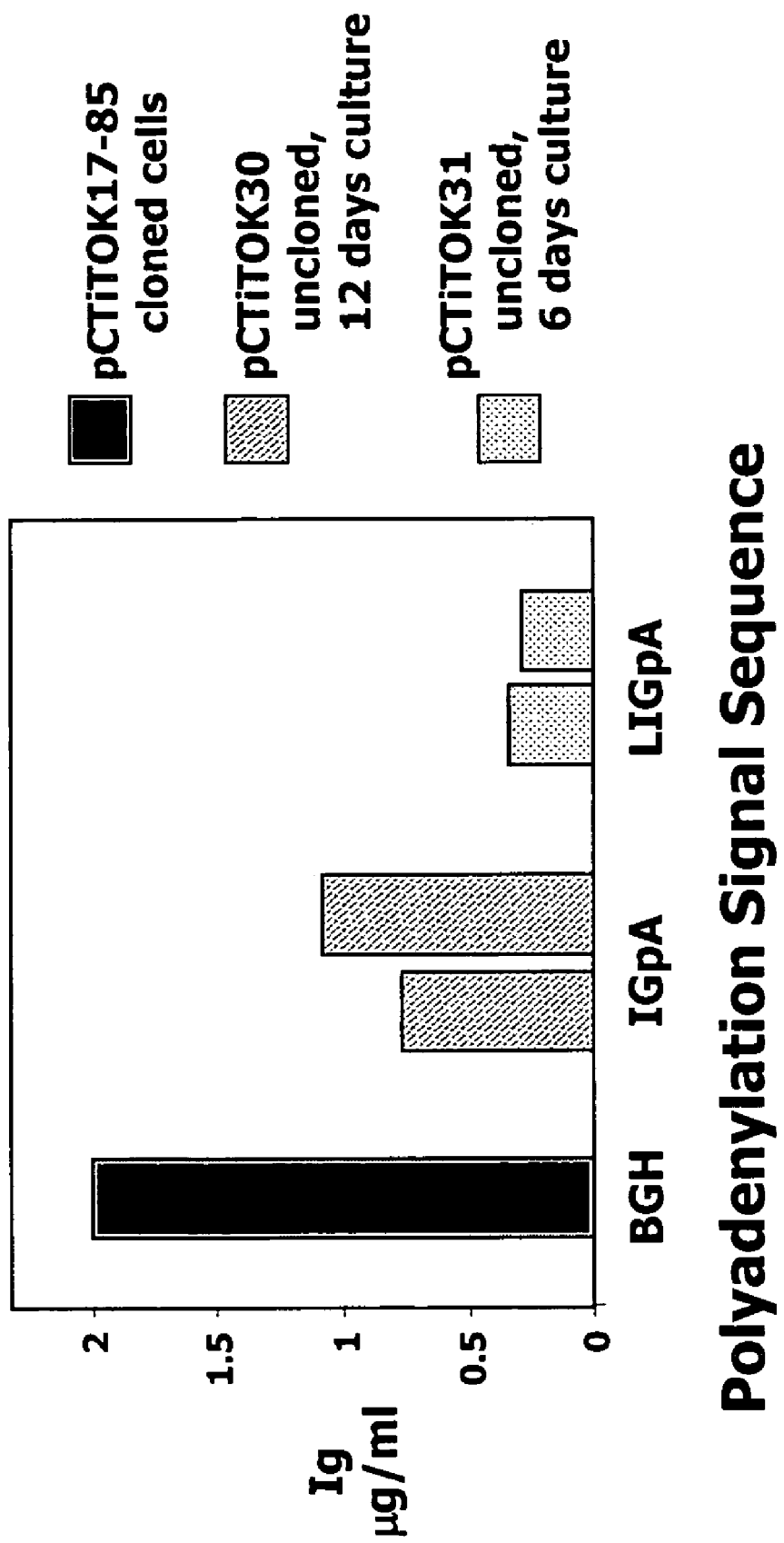
FIG. 4 is a graph comparing quantity of RAGE-immunoglobulin fusion protein (μg/ml) produced by CHO cells transfected with a vector comprising either the BGH, IGPA or LIGPA polyadenylation signal sequence.

A description of preferred embodiments of the invention follows.

The practice of the present invention will employ, unless otherwise indicated, conventional techniques of cell culture, molecular biology, microbiology, cell biology, and immunology, which are well within the skill of the art. Such techniques are fully explained in the literature. See, e.g., Sambrook et al., 1989, "Molecular Cloning: A Laboratory Manual", Cold Spring Harbor Laboratory Press; Ausubel et al. (1995), "Short Protocols in Molecular Biology", "Molecular Cloning: A Laboratory Manual" by T. Maniatis, et al., Cold Spring Harbor Laboratory, Cold Spring Harbor, N.Y., 1982, John Wiley and Sons; Methods in Enzymology (several volumes); Methods in Cell Biology (several volumes), and Methods in Molecular Biology (several volumes).

Fusion Proteins

In one embodiment, the present invention is a fusion protein comprising a fragment of the extracellular domain of a RAGE and an immunoglobulin element ("a RAGE-Ig fusion protein" or a fRAGE-Ig). As used herein, a "fusion protein" refers to a protein or polypeptide comprising two or more non-contiguous amino acid sequences. The RAGE-Ig fusion proteins of the invention comprise non-contiguous amino acid sequences from two or more different proteins. The amino acid sequences from the two or more different proteins may be full amino acid sequences or partial amino acid sequences (i.e., fragments) of the proteins.

The RAGE-Ig fusion proteins of the invention comprise at least a first and a second polypeptide, wherein the first polypeptide comprises a fragment of the extracellular domain of a RAGE and the second polypeptide comprises an immunoglobulin element. The RAGE-Ig fusion proteins of the invention include fusion proteins wherein the fragment of the extracellular domain of a RAGE is N-terminal to the immunoglobulin element, as well as fusion proteins wherein the immunoglobulin element is N-terminal to the fragment of the extracellular domain of a RAGE.

As used herein, "RAGE" or "Receptor for Advanced Glycation Endproducts" is a multiligand receptor that is a member of the immunoglobulin (Ig) superfamily. Known ligands for RAGE include, e.g., Advanced Glycation Endproducts of Proteins (AGEs), High Mobility Group Box 1 (HMGB1, also known as HMG-1, HMG1 and amphoterin), amyloid β-peptide, S100/calgranulin family proteins and leukocyte integrins (e.g., Mac-1) (Schmidt, A. et al., *J. Clin. Invest.* 108:949-955 (2001); Chavakis, T. et al., *J. Exp. Med.* 198:1507-1515 (2003); the entire teachings of both of which are incorporated herein by reference). RAGE proteins contain a single membrane-spanning domain of about 19 amino acids, which separates the protein into an extracellular domain and an intracellular domain (Neeper, M. et al., *J. Biol. Chem.* 267(21):14998-15004 (1992); the entire teachings of which are incorporated herein by reference). In the case of human RAGE, the protein is 404 amino acids in length and comprises a signal sequence of about 19 amino acids, an extracellular domain of about 321 amino acids, a transmembrane domain of about 23 amino acids and an intracellular domain of about 41 amino acids (Neeper, M. et al., id.; GenBank Accession No. NP_001127). The nucleotide sequence (GenBank Accession No. M91211; SEQ ID NO:1) and amino acid sequence (GenBank Accession No. NP_001127; SEQ ID NO:2) of human RAGE are depicted in FIGS. 1A and 1B respectively. RAGE proteins from other species contain similar domains, although not necessarily of the same length. For example, bovine RAGE is 416 amino acids in length and comprises a signal sequence of 22 amino acids, followed by an extracellular domain of 332 amino acids, a transmembrane domain of 19 hydrophobic amino acids and a highly charged intracellular domain of 43 amino acids (Neeper, M. et al., id.; GenBank Accession No. M91212). RAGE also contains three immunoglobulin-like domains (Ig-like domains) (Neeper, M. et al., id.). The N-terminal Ig-like domain is a V-like domain and, in human RAGE, this V-like domain spans from amino acid 24 to 118. The other two Ig-like domains are C-like domains; the C-terminal of which spans from amino acid 249 to 308 (GenBank Accession No. M91212). As used herein, these three Ig-like domains are labeled first, second and third Ig-like domains, with reference to their occurrence within the RAGE protein (i.e., the first Ig-like domain is the V-like domain, which, in human RAGE, spans from amino acid 24 to 118, the second Ig-like domain is the N-terminal C-like domain, and the third Ig-like domain is the C-terminal C-like domain, which, in human RAGE, spans from amino acid 249 to 308).

In one embodiment, the fusion protein of the invention comprises at least a first and a second polypeptide, wherein the first polypeptide comprises a fragment of a RAGE extracellular domain and the second polypeptide comprises an immunoglobulin element.

In another embodiment, the fusion protein comprises at least a first and a second polypeptide, wherein the first polypeptide consists essentially of a fragment of a RAGE extracellular domain and the second polypeptide comprises an immunoglobulin element.

In yet another embodiment, the fusion protein comprises at least a first and a second polypeptide, wherein the first polypeptide consists of a fragment of a RAGE extracellular domain and the second polypeptide comprises an immunoglobulin element.

As described herein, the fusion proteins of the invention comprise a fragment of a RAGE extracellular domain and an immunoglobulin element. As used herein, "a fragment of a RAGE extracellular domain" or "fRAGE-Ig" does not include the amino acid sequence of an entire RAGE extracellular domain. The fragment of a RAGE extracellular domain can comprise one, two or three of the Ig-like domains described herein. In a particular embodiment, the fragment of a RAGE extracellular domain comprises all three Ig-like domains (i.e., the V-like domain and the two C-like domains). In another embodiment, the fragment of a RAGE extracellular domain consists essentially of all three Ig-like domains. In still another embodiment, the fragment of a RAGE extracellular domain consists of all three Ig-like domains. As used herein, a fragment of a RAGE extracellular domain comprises at least 6 contiguous amino acids from a RAGE extracellular domain. Useful fragments of a RAGE extracellular domain include those that retain one or more of the biological activities of the polypeptide (e.g., ligand binding, receptor mediated signaling).

In one embodiment, the fragment of a RAGE extracellular domain comprises the first Ig-like domain of RAGE (i.e., the V-like domain). In other embodiments, the fragment of a RAGE extracellular domain consists essentially of, or consists of, the first Ig-like domain of RAGE.

In one embodiment, the fragment of a RAGE extracellular domain comprises the first two Ig-like domains of RAGE (i.e., the V-like domain and the N-terminal C-like domain). In other embodiments, the fragment of a RAGE extracellular domain consists essentially of, or consists of, the first two Ig-like domains of RAGE.

In one embodiment, the fragment of a RAGE extracellular domain comprises the contiguous amino acid sequence from about the N-terminal amino acid of RAGE to about the C-terminal amino acid of the third Ig-like domain of RAGE. In this embodiment, the fragment of a RAGE extracellular domain comprises the signal sequence of the RAGE (i.e., the first 22 or so amino acids of a RAGE). In other embodiments, the fragment of a RAGE extracellular domain consists essentially of, or consists of, the contiguous amino acid sequence from about the N-terminal amino acid of RAGE to about the C-terminal amino acid of the third Ig-like domain of RAGE.

In one embodiment, the fragment of a RAGE extracellular domain comprises the contiguous amino acid sequence from about the N-terminal amino acid of the first Ig-like domain of RAGE to about the C-terminal amino acid of the third Ig-like domain of RAGE. As described herein, in human RAGE, the first Ig-like domain starts at about amino acid 24, immediately after the signal sequence, while the third Ig-like domain ends at about amino acid 308. In other embodiments, the fragment of a RAGE extracellular domain consists essentially of, or consists of, the contiguous amino acid sequence from about the N-terminal amino acid of the first Ig-like domain of RAGE to about the C-terminal amino acid of the third Ig-like domain of RAGE. The person of ordinary skill in the art can easily determine at what residues the Ig-like domains of a particular RAGE (e.g., a RAGE from a non-human animal) begin and end.

In certain embodiments, the RAGE-Ig fusion proteins are defined by a particular amino acid sequence from about a particular enumerated amino acid residue to about another enumerated amino acid residue. The term "about" as used in this context allows for the addition of a few (e.g., 1, 2, 3 or 4) flanking amino acid residues or deletion of a few (e.g., 1, 2, 3 or 4) amino acid residues from the delineated amino acid sequence.

As used herein, a RAGE or fragment thereof (e.g., a RAGE extracellular domain, a fragment of a RAGE extracellular domain) is not limited to a particular species. In one embodiment, the RAGE or fragment thereof is a mammalian RAGE or fragment thereof (e.g., a mammalian RAGE extracellular domain, a fragment of a mammalian RAGE extracellular domain). In a particular embodiment, the RAGE or fragment thereof is a human RAGE or fragment thereof (e.g., a human RAGE extracellular domain, a fragment of a human RAGE extracellular domain). In another embodiment, the fusion protein comprises a fragment of a human RAGE extracellular domain. In other embodiments, the RAGE or fragment thereof is a RAGE from a primate, a cow, a sheep, a goat, a horse, a dog, a cat, a rabbit, a guinea pig, a rat, a mouse or other bovine, ovine, equine, canine, feline, rodent, or murine species.

The amino acid sequence of a human RAGE is depicted in FIG. 1B (GenBank Accession No. NP_001127; SEQ ID NO:2). In certain embodiments, the fusion protein comprises a fragment of a human RAGE extracellular domain that comprises, consists essentially of, or consists of, from about amino acid residue 1 to about amino acid residue 305 of SEQ ID NO:2. In other embodiments, the fusion protein comprises a fragment of a human RAGE extracellular domain that comprises, consists essentially of, or consists of, from about amino acid residue 19 to about amino acid residue 305 of SEQ ID NO:2.

The RAGE-Ig fusion proteins of the invention include fusion proteins wherein the RAGE or fragment thereof (e.g., a RAGE extracellular domain, a fragment of a RAGE extracellular domain) is N-terminal to the immunoglobulin element, as well as fusion proteins wherein the immunoglobulin element is N-terminal to the RAGE or fragment thereof. In one embodiment, the fusion protein comprises a RAGE or fragment thereof (e.g., a RAGE extracellular domain, a fragment of a RAGE extracellular domain) and an immunoglobulin element, wherein the RAGE or fragment thereof is N-terminal to the immunoglobulin element. In a particular embodiment, the fusion protein comprises a fragment of a RAGE extracellular domain and an immunoglobulin element, wherein the fragment of a RAGE extracellular domain is N-terminal to the immunoglobulin element. In another embodiment, the fusion protein comprises a RAGE or fragment thereof and an immunoglobulin element, wherein the RAGE or fragment thereof is C-terminal to the immunoglobulin element. In a particular embodiment, the fusion protein comprises a fragment of a RAGE extracellular domain and an immunoglobulin element, wherein the RAGE or fragment thereof is C-terminal to the immunoglobulin element.

As described herein, the fusion proteins of the invention comprise a RAGE or fragment thereof (e.g., a RAGE extracellular domain, a fragment of a RAGE extracellular domain) and an immunoglobulin element. As used herein, an immunoglobulin element may be a portion of an immunoglobulin and is not limited to an immunoglobulin from any particular species. Immunoglobulin elements may be derived from immunoglobulins from a variety of species. In one embodiment, the immunoglobulin element is a mammalian immunoglobulin element (i.e., an immunoglobulin element derived from a mammalian immunoglobulin). In a particular embodiment, the immunoglobulin element is a human immunoglobulin element (i.e., an immunoglobulin element derived from a human immunoglobulin). Immunoglobulin elements that are derived from immunoglobulins from other species, including, but not limited to, primates, cows, sheep, goats, horses, dogs, cats, rabbits, guinea pigs, rats, mice or other bovine, ovine, equine, canine, feline, rodent, or murine species, are also encompassed by the invention.

In a particular embodiment, the immunoglobulin element comprises an immunoglobulin heavy chain. In another embodiment, the immunoglobulin element comprises one or more domains of an immunoglobulin heavy chain. For example, an immunoglobulin element may comprise a heavy chain or a portion thereof from an IgG, IgD, IgE, IgA or IgM molecule. In a particular embodiment, the immunoglobulin element comprises an IgG heavy chain or portion thereof (e.g., an IgG1 heavy chain or portion thereof, an IgG2 heavy chain or portion thereof, an IgG3 heavy chain or portion thereof, an IgG4 heavy chain or portion thereof). Immunoglobulin heavy chain constant region domains include any or all of $C_H1$, $C_H2$, $C_H3$, $C_H4$ and Fc domains, of any class of immunoglobulin heavy chain, including gamma, alpha, epsilon, mu, and delta classes. Immunoglobulin variable regions include $V_H$, $V_{kappa}$ or $V_{gamma}$. In one embodiment, the immunoglobulin element comprises a $C_H1$ domain. In another embodiment, the immunoglobulin element comprises an Fc domain. In still another embodiment, the immunoglobulin element comprises a $C_H1$ domain and an Fc domain.

In a particular embodiment, the immunoglobulin element comprises a mutated Fc receptor domain (e.g., an Fc receptor domain that has reduced affinity for an Fc receptor). The Leu-Leu-Gly-Gly motif, which corresponds to EU numbering 234-237 (Edelman, G. M. et al., *Proc. Natl. Acad. Sci. USA* 63:78-85 (1969)) is an important Fc-FcR binding sequence (see, e.g., Hutchins, J. T. et al., *Proc. Natl. Acad. Sci. USA* 92:11980-11984 (1995)). Mutations of the Fc receptor domain that can inhibit Fc receptor binding include, e.g., mutations of this Leu-Leu-Gly-Gly motif, such as mutations of residues L117 and G119, wherein the numbering corresponds to SEQ ID NO:4 (wherein the mutations correspond to L235 and Gly237 based on EU numbering). In one embodiment, the immunoglobulin element comprises a mutated Fc receptor domain in which L117 (L235 based on EU numbering) and G119 (G237 based on EU numbering) are mutated. In a particular embodiment, the immunoglobulin element comprises a mutated Fc receptor domain comprising the mutations L117A and/or G119A; with numbering according to SEQ ID NO:4. Such mutations are present and are identified in the RAGE-Ig fusion protein exemplified herein (the nucleotide sequence of which is depicted as SEQ ID NO:5 and the amino acid sequence of which is depicted as SEQ ID NO:6; see FIGS. 3A and 3B).

In a particular embodiment, the immunoglobulin element comprises an IgG1 (e.g., a human IgG1) or portion thereof. A nucleotide (SEQ ID NO:3) and amino acid sequence (SEQ ID NO:4) of a human IgG1 are depicted in FIGS. 2A and 2B, respectively. In one embodiment, the immunoglobulin element comprises the amino acid sequence depicted in SEQ ID NO:4 or a portion thereof. In another embodiment, the immunoglobulin element comprises the amino acid sequence from about amino acid residue 101 to about amino acid residue 329 of SEQ ID NO:4.

As described herein, a particular RAGE-Ig fusion protein (SEQ ID NO:6) was produced (see FIGS. 3A and 3B for nucleotide and amino acid sequences of this RAGE-Ig fusion protein). This RAGE-Ig fusion protein comprised a fragment of the extracellular region of human RAGE, specifically amino acids 1-305 of SEQ ID NO:2 (GenBank Accession No. NP_001127; FIG. 1B), and an immunoglobulin element that was a fragment of a human IgG1, specifically amino acids 101-329 of SEQ ID NO:4 (GenBank Accession No. J00228; FIG. 2B). In one embodiment, the fusion protein comprises the amino acid sequence depicted in SEQ ID NO:6.

In a particular embodiment, the fusion protein comprises a fragment of a human RAGE extracellular domain that comprises from about amino acid residue 19 to about amino acid residue 305 of SEQ ID NO:2 and an immunoglobulin element that comprises from about amino acid residue 101 to about amino acid residue 329 of SEQ ID NO:4.

In certain embodiments, the RAGE-Ig fusion proteins of the invention include amino acid variants of the RAGE-Ig fusion proteins. Such variants include RAGE-Ig variant fusion proteins comprising amino acid alterations within the RAGE domain and/or the immunoglobulin domain. RAGE-Ig variant fusion proteins can be designed and produced for a variety of reasons, including, e.g., increased affinity for a ligand (e.g., HMGB1), increased stability, purification and preparation of a binding partner of the RAGE-Ig fusion protein, modification of the plasma half life, improved therapeutic efficacy, and/or lessening the severity or occurrence of side effects that occur during therapeutic use of the RAGE-Ig fusion protein. In particular embodiments, the RAGE-Ig variant fusion proteins of the invention comprise an amino acid sequence that is at least 80% identical, at least 90% identical, at least 95% identical, at least 97% identical, or at least 99% identical, to the amino acid sequence depicted as SEQ ID NO:6 (FIG. 3B) or a ligand-binding fragment thereof. Amino acid sequence variants of the RAGE-Ig fusion proteins of the invention include insertional, substitutional, and/or deletional variants. These RAGE-Ig variant fusion proteins can be prepared by methods that are known in the art, e.g., using site-specific mutagenesis to alter one or more nucleotides of the nucleic acid sequence encoding the RAGE-Ig fusion protein and subsequently expressing the altered nucleic acid sequence. RAGE-Ig variant fusion proteins can also be prepared by in vitro synthesis.

The percent identity of two amino acid sequences (or two nucleic acid sequences) can be determined by aligning the sequences for optimal comparison purposes (e.g., gaps can be introduced in the sequence of a first sequence). The amino acids or nucleotides at corresponding positions are then compared, and the percent identity between the two sequences is a function of the number of identical positions shared by the sequences (i.e., % identity=# of identical positions/total # of positions×100). In certain embodiments, the length of the RAGE-Ig fusion protein aligned for comparison purposes is at least 30%, preferably, at least 40%, more preferably, at least 60%, and even more preferably, at least 70%, 80%, 90%, or 100%, of the length of the reference sequence, for example, the nucleotide sequence depicted as SEQ ID NO:5 or the amino acid sequence depicted as SEQ ID NO:6. The actual comparison of the two sequences can be accomplished by well-known methods, for example, using a mathematical algorithm. A preferred, non-limiting example of such a mathematical algorithm is described in Karlin et al. (*Proc. Natl. Acad. Sci. USA*, 90:5873-5877 (1993)). Such an algorithm is incorporated into the BLASTN and BLASTX programs (version 2.2) as described in Schaffer et al. (*Nucleic Acids Res.*, 29:2994-3005 (2001)). When utilizing BLAST and Gapped BLAST programs, the default parameters of the respective programs (e.g., BLASTN; available at the Internet site for the National Center for Biotechnology Information) can be used. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

Another non-limiting example of a mathematical algorithm utilized for the comparison of sequences is the algorithm of Myers and Miller, CABIOS (1989). Such an algorithm is incorporated into the ALIGN program (version 2.0), which is part of the GCG (Accelrys, San Diego, Calif.) sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (*Comput. Appl. Biosci.*, 10: 3-5 (1994)); and FASTA described in Pearson and Lipman (*Proc. Natl. Acad. Sci USA*, 85: 2444-2448 (1988)).

In another embodiment, the percent identity between two amino acid sequences can be accomplished using the GAP program in the GCG software package (Accelrys, San Diego, Calif.) using either a Blossom 63 matrix or a PAM250 matrix, and a gap weight of 12, 10, 8, 6, or 4 and a length weight of 2, 3, or 4. In yet another embodiment, the percent identity between two nucleic acid sequences can be accomplished using the GAP program in the GCG software package (Accelrys, San Diego, Calif.), using a gap weight of 50 and a length weight of 3.

The binding properties of a RAGE-Ig fusion protein can be expressed in terms of binding specificity, which may be determined as a comparative measure relative to other known substances that bind to the RAGE-Ig fusion protein (e.g., using dissociation constants ($K_d$) or association constants ($K_a$)). Standard assays for quantitating binding and determining binding affinity are known in the art and include, e.g., equilibrium dialysis, equilibrium binding, gel filtration, surface plasmon resonance, BIACORE®, microbalances, the use of a labeled binding partners and indirect binding assays (e.g., competitive inhibition assays) (Paul, W. E., *Fundamental Immunology, Second Ed.*, Raven Press, New York, pp. 315-352 (1989); the entire teachings of which are incorporated herein by reference). For example, as is well known in the art, the dissociation constant of a protein (e.g., a RAGE-Ig fusion protein) can be determined by contacting the protein with a binding partner (e.g., a RAGE ligand (e.g., HMGB1 or RAGE-binding fragment thereof)) and measuring the concentration of bound and free protein as function of its concentration. Formulaically, this can be represented as:

$$[\text{Bound}] = N \times [\text{Free}] / ((K_d) + [\text{Free}])$$

where [Bound]=the concentration of bound protein (e.g., a RAGE-Ig fusion protein); [Free]=the concentration of unbound protein (e.g., a RAGE-Ig fusion protein); N=the concentration of binding sites on the protein; and $K_d$=the dissociation constant (a quantitative measure of the binding affinity). The association constant, $K_a$, is the reciprocal of the dissociation constant, $K_d$. A detailed description of binding affinities and kinetics can be found in Paul, W. E., ed., Fundamental Immunology, 4$^{th}$ Ed., Lippincott-Raven, Philadelphia (1999), p. 75-110, which focuses on antibody-immunogen interactions.

In one embodiment, the RAGE-Ig fusion protein binds to a binding partner (e.g., a ligand (e.g., HMGB1 or a RAGE-binding fragment thereof) with a particular affinity (e.g., a $K_a$ of at least $10^3$ M$^{-1}$, a $K_a$ of at least $10^5$ M$^{-1}$, a $K_a$ of at least $10^7$ M$^{-1}$ or a $K_a$ of at least $10^9$ M$^{-1}$). In other embodiments, the RAGE-Ig fusion proteins of the invention have a $K_a$ for a particular binding partner that is equal to, or greater than, about $1 \times 10^3$ liters/mole, $1 \times 10^4$ liters/mole, $1 \times 10^5$ liters/mole, $1 \times 10^6$ liters/mole, $1 \times 10^7$ liters/mole or $1 \times 10^8$ liters/mole. In other embodiments, the RAGE-Ig fusion proteins of the invention have a $K_d$ that is equal to, or less than, about $1 \times 10^{-3}$ M, $1 \times 10^{-4}$ M $1 \times 10^{-5}$ M, $1 \times 10^{-6}$ M, $1 \times 10^{-7}$ M, $1 \times 10^{-8}$ M, $1 \times 10^{-9}$ M or $1 \times 10^{-10}$ M. In a particular embodiment, the RAGE-Ig fusion proteins of the invention have a $K_d$ between $1 \times 10^{-5}$ and $9.9 \times 10^{-7}$ M.

Figure 10A:
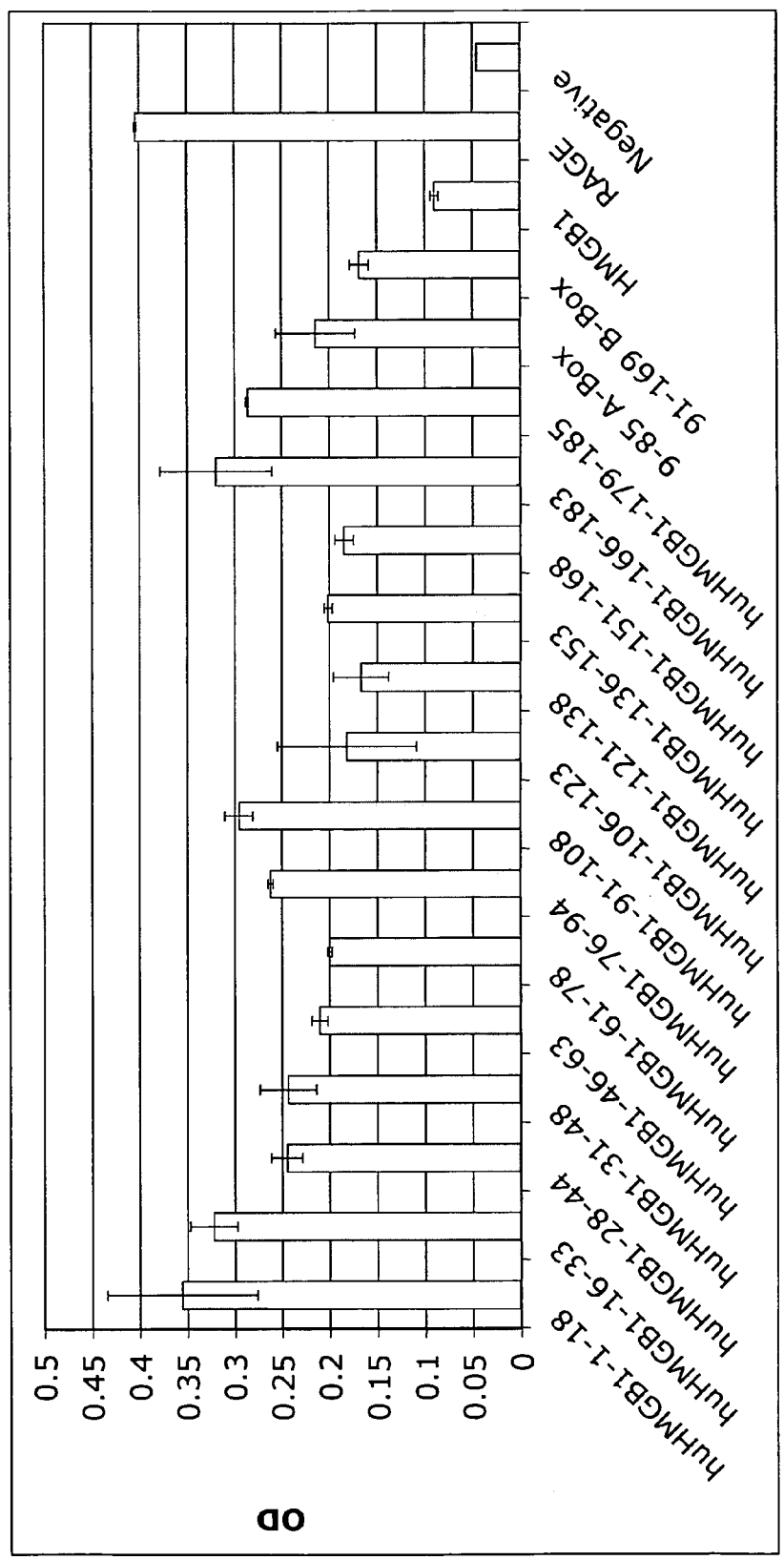
FIGS. 10A-10C are histograms showing the results of competition ELISAs using full-length HMGB1, HMGB1 A Box, HMGB1 B Box, and various 18 to 30 amino acid peptide fragments of HMGB1. For the competition ELISA experiments, RAGE-Ig fusion protein and the respective HMGB1 or HMGB1 peptide fragment were incubated with an ELISA plate that was coated with recombinant HMGB1. Bound RAGE-Ig fusion protein was subsequently detected using anti-human IgG conjugated to HRP, developed using TMB, and read using a plate reader at 650 nm. As depicted in FIGS. 10A-10C, RAGE-Ig fusion protein bound to solid-phase HMGB1, and this binding was inhibited by soluble HMGB1, HMGB1 A box and HMGB1 B box. Further, as shown in FIGS. 10A to 10C, two amino acid regions of HMGB1 (amino acid 31 to 78 and amino acid 121 to 158) contain binding domains for RAGE. Specifically.
Figure 10B:
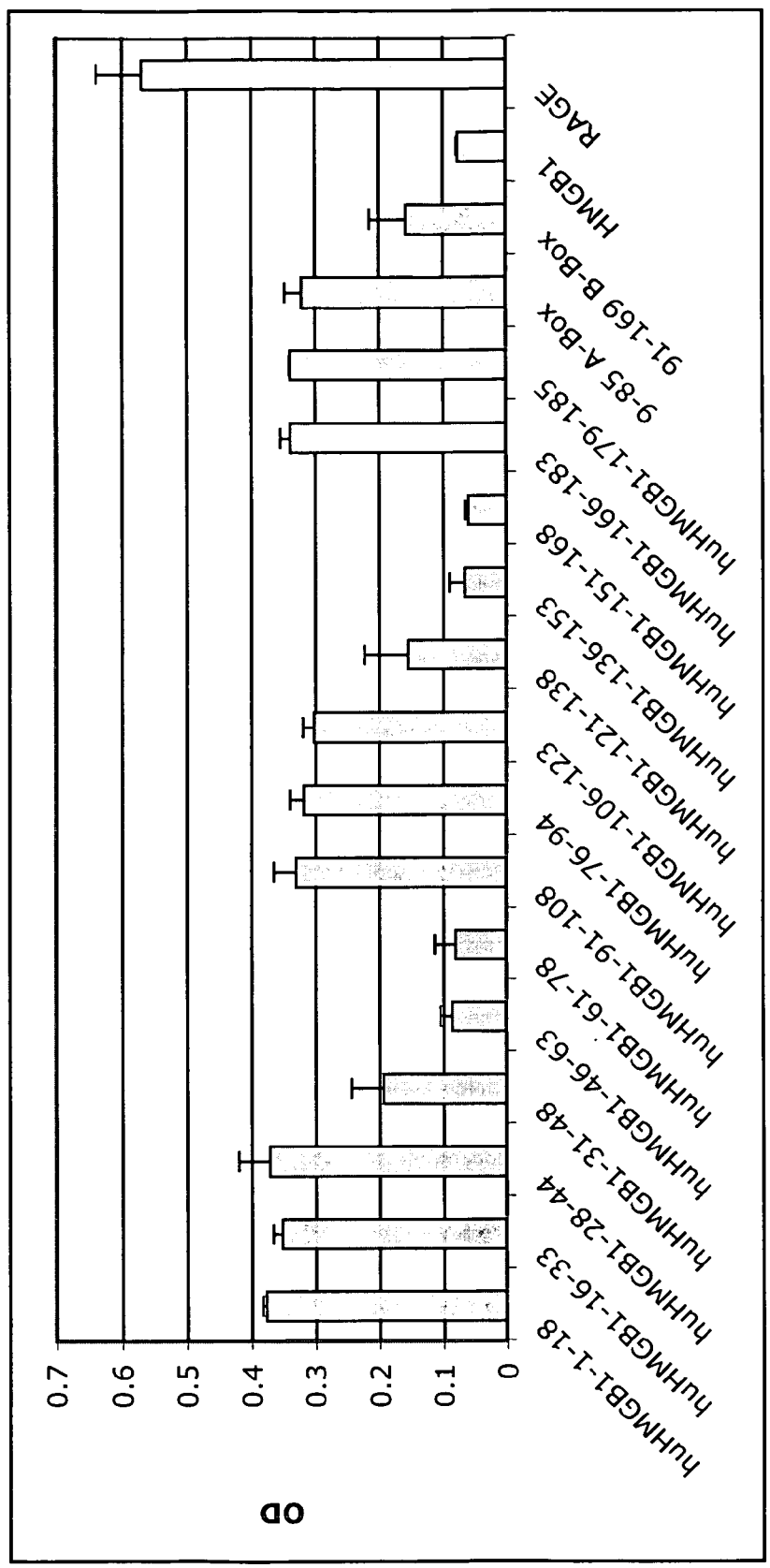
Figure 10C:
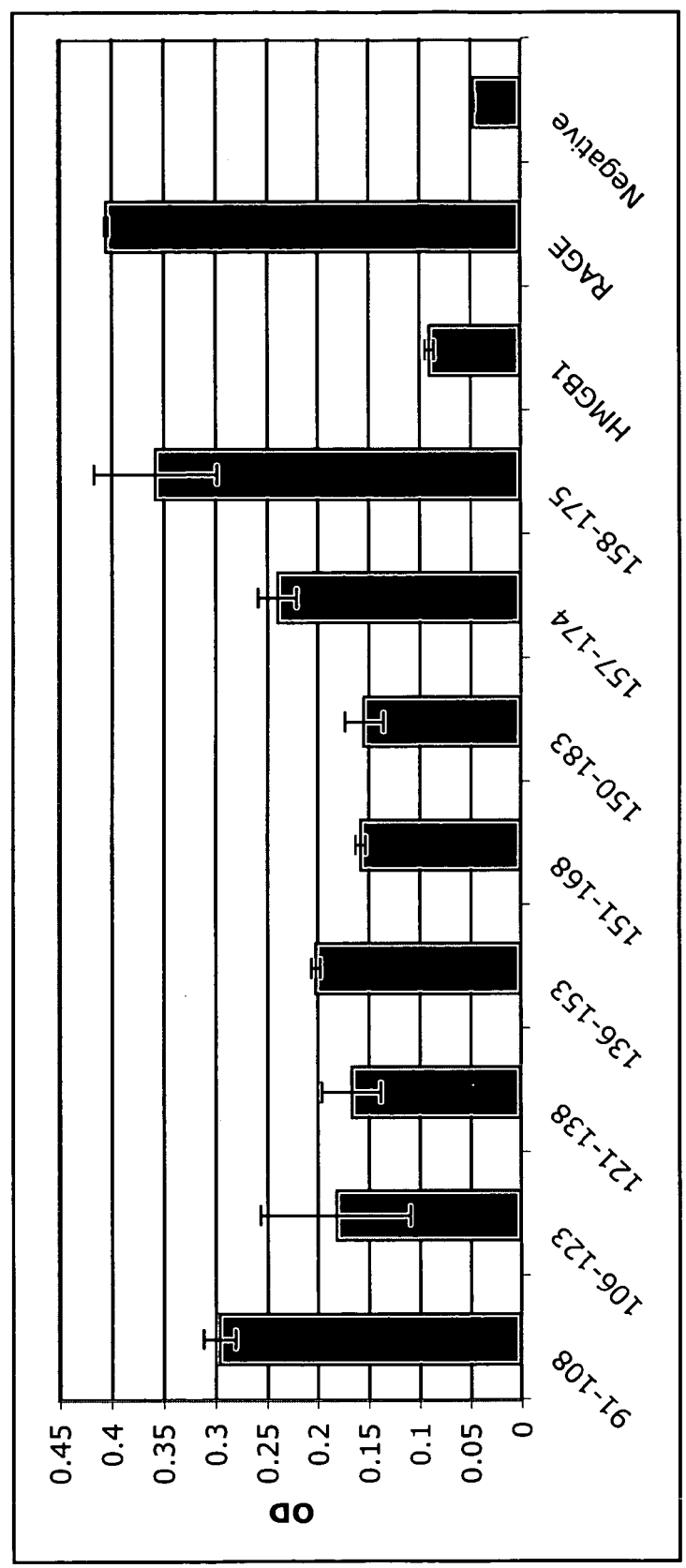

As exemplified herein, a RAGE-Ig fusion protein was produced that exhibited binding to HMGB1 (FIG. 6), the HMGB1 A box (FIG. 7A), the HMGB1 B box (FIG. 7A) and particular peptide fragments of HMGB1 (FIGS. 10A-10C). Further, the RAGE-Ig fusion protein exemplified herein exhibited a higher binding affinity for HMGB1 than did the commercially-available RAGE/Fc chimera (R&D Systems, Inc., Minneapolis, Minn., Catalog No. 1145-RG) (see Example 7 and FIG. 6). In addition, the RAGE-Ig fusion protein exemplified herein also exhibited a higher binding affinity for the HMGB1 A box and the HMGB1 B box than did the commercially-available RAGE/Fc chimera (see Example 8 and FIGS. 7A and 7B).

As described above, the association constant ($K_a$) and dissociation constant ($K_d$) of a protein (e.g., a RAGE-Ig fusion protein) can be determined, e.g., using the formula described above. The more stable the interaction between the protein (e.g., a RAGE-Ig fusion protein) and its binding partner (e.g., a RAGE ligand), the smaller the $K_d$ of the protein. Thus, in one embodiment, the RAGE-Ig fusion proteins of the invention have a $K_d$ for a RAGE binding partner (e.g., a RAGE ligand (e.g., HMGB1 or a RAGE-binding fragment thereof)) that is equal to or less than the $K_d$ of the commercially-available RAGE/Fc chimera and the same binding partner (i.e., the RAGE-Ig fusion proteins of the invention have a higher affinity for a RAGE binding partner than does the commercially-available RAGE/Fc chimera). In certain embodiments, the RAGE-Ig fusion proteins of the invention have a $K_d$ for a particular binding partner (e.g., a RAGE ligand (e.g., HMGB1 or a RAGE-binding fragment thereof)) that is about 100% of or less than, about 97% of or less than, about 95% of or less than, about 90% of or less than, about 85% of or less than, about 80% of or less than, about 75% of or less than, about 70% of or less than, about 60% of or less than, or about 50% of or less than, the $K_d$ of the commercially-available RAGE/Fc chimera and the same binding partner. For example, if the $K_d$ of the commercially-available RAGE/Fc chimera and a particular binding partner (e.g., HMGB1) is $1.55 \times 10^{-4}$ M, the RAGE-Ig fusion protein of the invention having a $K_d$ of $1.24 \times 10^{-4}$ M (i.e., $1.55 \times 10^{-4} \times 0.8$ (i.e., 80%)= $1.24 \times 10^{-4}$ M) would have a $K_d$ that is 80% of that of the commercially-available RAGE/Fc chimera and binding partner. As described above, suitable assays for determining and comparing dissociation constants are well known in the art.

In another embodiment, the RAGE-Ig fusion proteins of the invention have a $K_d$ for a particular binding partner (e.g., HMGB1 or a RAGE-binding fragment thereof) that is one half of (i.e., ½) or less than the $K_d$ of the commercially-available RAGE/Fc chimera and binding partner. For example, if the $K_d$ of the commercially-available RAGE/Fc chimera and a particular binding partner (e.g., HMGB1) is $1.55 \times 10^{-4}$ M, the RAGE-Ig fusion protein of the invention having a $K_d$ of $7.75 \times 10^{-5}$ M (i.e., $1.55 \times 10^{-4} \times 0.5$ (i.e., ½ or 50%)=$7.75 \times 10^{-5}$ M) would have a $K_d$ that is one half of that of the commercially-available RAGE/Fc chimera and the same binding partner. In other embodiments, the RAGE-Ig fusion proteins of the invention have a $K_d$ for a particular binding partner that is about ¼ of or less than, ⅛ of or less than, ¹⁄₁₀ of or less than, or ¹⁄₂₀ of or less than, the $K_d$ of the commercially-available RAGE/Fc chimera and the same binding partner.

In a particular embodiment, the RAGE-Ig fusion proteins of the invention have a higher binding affinity (e.g., a lower $K_d$) for HMGB1, than does the commercially-available RAGE/Fc chimera (R&D Systems, Inc., Minneapolis, Minn., Catalog No. 1145-RG). In other embodiments, the RAGE-Ig fusion proteins of the invention have a higher binding affinity (e.g., a lower $K_d$) for a RAGE-binding fragment of HMGB 1 (e.g., an HMGB1 A box, an HMGB1 B box, a RAGE-binding peptide fragment of HMGB1), than does the commercially-available RAGE/Fc chimera.

Compositions Comprising RAGE-Ig Fusion Protein

In another embodiment, the present invention is directed to a composition (e.g., a pharmaceutical composition) comprising a RAGE-Ig fusion protein, as described herein, in a pharmaceutically-acceptable excipient. The excipient that is included with the RAGE-Ig fusion proteins in these compositions can be selected based on the expected route of administration of the composition in therapeutic applications. The route of administration of the composition depends on the condition to be treated. For example, intravenous injection may be preferred for treatment of a systemic disorder, such as endotoxic shock, and oral administration may be preferred to treat a gastrointestinal disorder, such as a gastric ulcer. The dosage of the compositions to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. Typically, an effective amount can range from 0.01 mg per day to about 100 mg per day for an adult. Preferably, the dosage ranges from about 1 mg per day to about 100 mg per day or from about 1 mg per day to about 10 mg per day. Depending on the condition, the composition can be administered orally, parenterally, intranasally, vaginally, rectally, lingually, sublingually, buccally, intrabuccally and/or transdermally to the patient.

Accordingly, compositions designed for oral, lingual, sublingual, buccal and intrabuccal administration can be made without undue experimentation by means well known in the art, for example, with an inert diluent or with an edible carrier. The composition may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums, and the like.

Tablets, pills, capsules, troches and the like may also contain binders, recipients, disintegrating agent, lubricants, sweetening agents, and/or flavoring agents. Some examples of binders include microcrystalline cellulose, gum tragacanth and gelatin. Examples of excipients include starch and lactose. Some examples of disintegrating agents include alginic acid, corn starch, and the like. Examples of lubricants include magnesium stearate and potassium stearate. An example of a glidant is colloidal silicon dioxide. Some examples of sweetening agents include sucrose, saccharin, and the like. Examples of flavoring agents include peppermint, methyl salicylate, orange flavoring, and the like. Materials used in preparing these various compositions should be pharmaceutically pure and non-toxic in the amounts used.

The pharmaceutical compositions of the present invention can be administered parenterally, such as, for example, by intravenous, intramuscular, intrathecal and/or subcutaneous injection. Parenteral administration can be accomplished by incorporating the compositions of the present invention into a solution or suspension. Such solutions or suspensions may also include sterile diluents, such as water for injection, saline solution, fixed oils, polyethylene glycols, glycerine, propylene glycol and/or other synthetic solvents. Parenteral formulations may also include antibacterial agents, such as, for example, benzyl alcohol and/or methyl parabens, antioxidants, such as, for example, ascorbic acid and/or sodium bisulfite, and chelating agents, such as EDTA. Buffers, such as acetates, citrates and phosphates, and agents for the adjustment of tonicity, such as sodium chloride and dextrose, may also be added. The parenteral preparation can be enclosed in ampules, disposable syringes and/or multiple dose vials made of glass or plastic.

Rectal administration includes administering the composition into the rectum and/or large intestine. This can be accomplished using suppositories and/or enemas. Suppository formulations can be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves, and the like.

The compositions of the present invention can be administered nasally to a patient. As used herein, nasally administering or nasal administration includes administering the compositions to the mucous membranes of the nasal passage and/or nasal cavity of the patient. Pharmaceutical compositions for nasal administration of a composition include therapeutically effective amounts of the RAGE-Ig fusion protein, prepared by well-known methods for administration, for example, as a nasal spray, nasal drop, suspension, gel, ointment, cream and/or powder. Administration of the composition may also take place using a nasal tampon and/or nasal sponge.

Compositions Comprising RAGE-Ig Fusion Protein and an Additional Agent

In certain embodiments, the compositions (e.g., pharmaceutical compositions) of the invention further comprise one or more additional agents (e.g., an agent used to treat an inflammatory condition). Such additional agents are described below and/or are known to one of skill in the art.

Compositions Comprising RAGE-Ig Fusion Protein and an Antagonist of an Early Sepsis Mediator For example, the additional agent included in the compositions of the invention may be an antagonist of an early sepsis mediator. As used herein, an early sepsis mediator is a proinflammatory cytokine that is released from cells soon (i.e., within 30-60 min.) after induction of an inflammatory cytokine cascade (e.g., exposure to LPS). Nonlimiting examples of these cytokines are IL-1α, IL-1β, IL-6, PAF, and MIF. Also included as early sepsis mediators are receptors for these cytokines (for example, tumor necrosis factor receptor type 1) and enzymes required for production of these cytokines (for example, interleukin-1β converting enzyme). Antagonists of any early sepsis mediator, now known or later discovered, can be useful for these embodiments by further inhibiting an inflammatory cytokine cascade.

Nonlimiting examples of antagonists of early sepsis mediators are antisense compounds that bind to the mRNA of the early sepsis mediator, preventing its expression (see, e.g., Ojwang et al., *Biochemistry* 36:6033-6045, 1997; Pampfer et al., *Biol. Reprod.* 52:1316-1326, 1995; U.S. Pat. No. 6,228,642; Yahata et al., *Antisense Nucleic Acid Drug Dev.* 6:55-61, 1996; and Taylor et al., *Antisense Nucleic Acid Drug Dev.* 8:199-205, 1998), ribozymes that specifically cleave the mRNA of the early sepsis mediator (see, e.g., Leavitt et al., *Antisense Nucleic Acid Drug Dev.* 10: 409-414, 2000; Kisich et al., 1999; and Hendrix et al., *Biochem. J.* 314 (Pt. 2): 655-661, 1996), and antibodies that bind to the early sepsis mediator and inhibit their action (see, e.g., Kam and Targan, *Expert Opin. Pharmacother.* 1: 615-622, 2000; Nagahira et al., *J. Immunol Methods* 222, 83-92, 1999; Lavine et al., *J. Cereb. Blood Flow Metab.* 18: 52-58, 1998; and Holmes et al., *Hybridoma* 19: 363-367, 2000). An antagonist of an early sepsis mediator, now known or later discovered, is envisioned as within the scope of the invention. The skilled artisan can determine the amount of early sepsis mediator to use in these compositions for inhibiting any particular inflammatory cytokine cascade without undue experimentation, e.g., using routine dose-response studies.

In one embodiment, the compositions (e.g., pharmaceutical compositions) of the invention are administered with an agent that inhibits TNF biological activity. Such inhibitors of TNF activity include, e.g., peptides, proteins, synthesized molecules, for example, synthetic organic molecules, naturally-occurring molecule, for example, naturally occurring organic molecules, nucleic acid molecules, and components thereof. Preferred examples of agents that inhibit TNF biological activity include infliximab (REMICADE®; Centocor, Inc., Malvern, Pa.), etanercept (ENBREL®; Immunex; Seattle, Wash.), adalimumab (HUMIRA®; D2E7; Abbot Laboratories, Abbot Park Ill.), CDP870 (Pharmacia Corporation; Bridgewater, N.J.), CDP571 (Celltech Group plc, United Kingdom), Lenercept (Roche, Switzerland) and Thalidomide.

Compositions Comprising RAGE-Ig Fusion Protein and an Agent that Inhibits Complement Biological Activity In certain embodiments, the compositions (e.g., pharmaceutical compositions) of the invention include an agent that inhibits complement biological activity. As used herein, "an agent that inhibits complement biological activity" is an agent that decreases one or more of the biological activities of the complement system. Examples of complement biological activity include, but are not limited to, cell lysis, development of an inflammatory response, opsonization of antigen, viral neutralization, and clearance of immune complexes. Components of the complement system participate in the development of an inflammatory response by degranulating mast cells, basophils, and eosinophils, aggregation of platelets, and release of neutrophils from bone marrow. Agents that inhibit complement biological activity include, e.g., agents that inhibit (decrease) the interaction between a complement component and its receptor(s), agents that inhibit (decrease) formation of the MAC, agents that inhibit a key protein in the complement cascade, agents that inhibit conversion of complement C5 to C5a and C5b, and agents that inhibit the action of complement-derived anaphalytoxins C3a and C5a. Such agents include, but are not limited to peptides, proteins, synthesized molecules (for example, synthetic organic molecules), naturally-occurring molecule (for example, naturally occurring organic molecules), nucleic acid molecules, and components thereof. Preferred examples of agents that inhibit complement biological activity include agents that inhibit expression or activity or one or more of the following components of the complement system: C1q, C1r, C1s, Factor D, Factor B, Properdin, C2, C3, C4, C5, C6, C7, C8, C9, C3 convertase, C5 convertase, as well as fragments of components that are produced upon activation of complement, for example, fragment 2a, 2b, 3a, 3b, 4a, 4b, 5a, and/or 5b.

Examples of agents that inhibit complement biological activity include, but are not limited to: C5 inhibitors, for example, 5G1.1 (also known as Eculizumab; Alexion Pharmaceuticals, Inc., Cheshire, Conn.) and h5G1.1-SC (also known as Pexelizumab, Alexion Pharmaceuticals Inc., Cheshire, Conn.); C5a receptor antagonists, for example, NGD 2000-1 (Neurogen, Corp., Branford, Conn.) and AcPhe [Orn-Pro-D-Cyclohexylalanine-Trp-Arg] (AcF-[OPd-ChaWR]; see, e.g., Strachan, A. J. et al., *Br. J. Pharmacol.* 134(8):1778-1786 (2001)); C1 esterase inhibitor (C1-INH); Factor H (inactive C3b); Factor I (inactive C4b); soluble complement receptor type 1 (sCR1; see, e.g., U.S. Pat. No. 5,856,297) and sCR1-sLe(X) (see, e.g., U.S. Pat. No. 5,856, 300); membrane cofactor protein (MCP), decay accelerating factor (DAF) and CD59 and soluble recombinant forms thereof (Ashgar, S. S. et al., Front Biosci. 5:E63-E81 (2000) and Sohn, J. H. et al., *Invest. Opthamol. Vis. Sci.* 41(13):4195-4202 (2000)); Compstatin (Morikis et al., *Protein Sci.* 7:619-627 (1998); Sahu, A. et al., *J. Immunol.* 165:2491-2499 (2000)); chimeric complement inhibitor proteins having at least two complementary inhibitory domains (see, e.g., U.S. Pat. Nos. 5,679,546, 5,851,528 and 5,627,264); and small molecule antagonists (see, e.g., PCT Publication No. WO 02/49993, U.S. Pat. Nos. 5,656,659, 5,652,237, 4,510,158, 4,599,203 and 4,231,958). Other complement inhibitors are known in the art and are encompassed by the invention. In addition, methods for measuring complement activity (e.g., to identify agents that inhibit complement activity) are known in the art. Such methods include, e.g., using a 50% hemolytic complement ($CH_{50}$) assay (see, e.g., Kabat et al., Experimental Immunochemistry, 2nd Ed. (Charles C. Thomas, Publisher, Springfield, Ill.), p. 133-239 (1961)), using an enzyme immunoassay (EIA), using a liposome immunoassay (LIA) (see, e.g., Jaskowski et al. *Clin. Diagn. Lab. Immunol.* 6(1): 137-139 (1999)). See U.S. Provisional Application No. 60/589,608, entitled "HMGB Combination Therapies", by Walter Newman, filed on Jul. 20, 2004; the entire teachings of which are incorporated herein by reference.

Compositions Comprising RAGE-Ig Fusion Protein and an HMGB A Box or Biologically Active Fragment Thereof In other embodiments, the compositions (e.g., pharmaceutical compositions) of the invention include an HMGB A box or biologically active fragment thereof. As used herein, an "HMGB A box" also referred to herein as an "A box" (and also known as HMG A box) is a protein or polypeptide that has at least 50%, 60%, 70%, 75%, 80%, 85%, 90%, or 95% sequence identity to an HMGB A box, and has one or more of the following biological activities: inhibiting inflammation mediated by HMGB and/or inhibiting release of a proinflammatory cytokine from a cell. In one embodiment, the HMGB A box polypeptide has one of the above biological activities. HMGB A boxes are known in the art. Examples of polypeptides having A box sequences within them include, but are not limited to GenBank Accession Numbers AAA64970, AAB08987, P07155, AAA20508, S29857, P09429, NP_002119, CAA31110, S02826, U00431, X67668, NP_005333, NM_016957, and J04197, mammalian HMG1 ((HMGB1) as described, for example, in GenBank Accession Number U51677), mouse HMG1 as described, for example, in GenBank Accession Number CAA55631.1, rat HMG1 as described, for example, in GenBank Accession Number NP_037095.1, cow HMG1 as described, for example, in GenBank Accession Number CAA31284.1, HMG2 ((HMGB2) as described, for example, in GenBank Accession Number M83665), HMG-2A ((HMGB3, HMG-4) as described, for example, in GenBank Accession Numbers NM_005342 and NP_005333), HMG14 (as described, for example, in GenBank Accession Number P05114), HMG17 (as described, for example, in GenBank Accession Number X13546), HMGI (as described, for example, in GenBank Accession Number L17131), and HMGY (as described, for example, in GenBank Accession Number M23618); non-mammalian HMG T1 (as described, for example, in GenBank Accession Number X02666) and HMG T2 (as described, for example, in GenBank Accession Number L32859) (rainbow trout); HMG-X (as described, for example, in GenBank Accession Number D30765) (*Xenopus*), HMG D (as described, for example, in GenBank Accession Number X71138) and HMG Z (as described, for example, in GenBank Accession Number X71139) (*Drosophila*); NHP10 protein (HMG protein homolog NHP 1) (as described, for example, in GenBank Accession Number Z48008) (yeast); non-histone chromosomal protein (as described, for example, in GenBank Accession Number O00479) (yeast); HMG ½ like protein (as described, for example, in GenBank Accession Number Z11540) (wheat, maize, soybean); upstream binding factor (UBF-1) (as described, for example, in GenBank Accession Number X53390); PMS1 protein homolog 1 (as described, for example, in GenBank Accession Number U13695); single-strand recognition protein (SSRP, structure-specific recognition protein) (as described, for example, in GenBank Accession Number M86737); the HMG homolog TDP-1 (as described, for example, in GenBank Accession Number M74017); mammalian sex-determining region Y protein (SRY, testis-determining factor) (as described, for example, in GenBank Accession Number X53772); fungal proteins: mat-1 (as described, for example, in GenBank Accession Number AB009451), ste 11 (as described, for example, in GenBank Accession Number x53431) and Mc 1; SOX 14 (as described, for example, in GenBank Accession Number AF107043) (as well as SOX 1 (as described, for example, in GenBank Accession Number Y13436), SOX 2 (as described, for example, in GenBank Accession Number Z31560), SOX 3 (as described, for example, in GenBank Accession Number X71135), SOX 6 (as described, for example, in GenBank Accession Number AF309034), SOX 8 (as described, for example, in GenBank Accession Number AF226675), SOX 10 (as described, for example, in GenBank Accession Number AJ001183), SOX 12 (as described, for example, in Gen- Bank Accession Number X73039) and SOX 21 (as described, for example, in GenBank Accession Number AF107044); lymphoid specific factor (LEF-1) (as described, for example, in GenBank Accession Number X58636); T-cell specific transcription factor (TCF-1) (as described, for example, in GenBank Accession Number X59869); MTT1 (as described, for example, in GenBank Accession Number M62810) and SP100-HMG nuclear autoantigen (as described, for example, in GenBank Accession Number U36501). Other examples of HMGB polypeptides include those encoded by nucleic acid sequences having Genbank Accession Numbers AAH81839 (rat high mobility group box 1), NP_990233 (chicken high mobility group box 1), AAN11319 (dog high mobility group B1), AAC27653 (mole high mobility group protein), P07746 (trout high mobility group-T protein), AAA58771 (trout HMG-1), AAQ97791 (zebra fish high-mobility group box 1), AAH01063 (human high-mobility group box 2), and P10103 (cow high mobility group protein 1). Still other HMGB A boxes, which are encompassed by the invention, are described in PCT Publication WO 02/092004; the entire teachings of which are incorporated herein by reference.

Functional equivalents (e.g., biologically active fragments) of HMGB A boxes can also be used in compositions and methods of the present invention. In one embodiment, a functional equivalent of an HMGB A box inhibits release of a proinflammatory cytokine from a cell treated with an HMGB polypeptide. Examples of HMGB A box functional equivalents include, for example, biologically active fragments, post-translational modifications, variants, or fusion proteins comprising A boxes, as defined herein. A box functional equivalents can be generated using standard molecular biology techniques and assaying the function using known methods, for example, by determining if the fragment, when administered to a cell (e.g., a macrophage), decreases or inhibits release of a proinflammatory cytokine from the cell.

In one embodiment, the HMGB A box included in the composition, is a vertebrate HMGB A box. In another embodiment, the HMGB A box included in the composition, is a mammalian HMGB A box. In another embodiment, the HMGB A box included in the composition, is a human HMGB1 A box. In yet another embodiment, the HMGB A box included in the composition, comprises, consists essentially of, or consists of, SEQ ID NO:13 (FIG. 15C; A box from human, rat and mouse HMGB1).

Compositions Comprising RAGE-Ig Fusion Protein and an Antibody or Antigen-Binding Fragment that Binds to an HMGB1 Polypeptide In certain embodiments, the compositions (e.g., pharmaceutical compositions) of the invention include an antibody or antigen-binding fragment that binds to an HMGB polypeptide or an antigenic fragment of an HMGB polypeptide (anti-HMGB antibodies). These antibodies and antigen-binding fragments can be combined with the RAGE-Ig fusion proteins of the invention. The anti-HMGB antibodies and anti-gen-binding fragments can be neutralizing antibodies or antigen-binding fragments (i.e., can inhibit a biological activity of an HMG polypeptide or a fragment thereof, for example, the release of a proinflammatory cytokine from a vertebrate cell induced by HMGB). In certain embodiments, the antibodies and antigen-binding fragments that are included in the compositions of the invention selectively bind to an HMGB B box or a fragment thereof, but do not selectively bind to non-B box epitopes of HMGB (anti-HMGB B box antibodies and antigen-binding fragments thereof). In other embodiments, the antibodies and antigen-binding fragments that are included in the compositions of the invention selectively bind to an HMGB A box or a functional equivalent thereof, but do non selectively bind to non-A box epitopes of HMGB (anti-HMGB A box antibodies and antigen-binding fragments thereof). In these embodiments, the antibodies and antigen-binding fragments can also be neutralizing antibodies and antigen-binding fragments. Antibodies to HMGB have been shown to inhibit release of a proinflammatory cytokine from a cell treated with an HMGB polypeptide (see, for example, PCT publication WO 02/092004). Such antibodies can be combined with the RAGE-Ig fusion proteins of the invention, and/or one or more of the other agents described herein.

Antibodies to HMGB, and methods for making antibodies to HMGB, are known in the art (see, for example, PCT publication WO 02/092004). As used herein, the term "antibody" or "purified antibody" refers to an immunoglobulin molecule. The term "antigen-binding fragment" or "purified antigen-binding fragment", as used herein, refers to immunologically active portions of immunoglobulin molecules, i.e., molecules that contain an antigen binding site that selectively bind to an antigen. A molecule that selectively binds to a polypeptide of the invention is a molecule that binds to that polypeptide or a fragment thereof, but does not substantially bind other molecules in a sample, e.g., a biological sample that naturally contains the polypeptide. Examples of immunologically active portions of immunoglobulin molecules include, but are not limited to Fv, Fab, Fab' and F(ab')$_2$ fragments. Such fragments can be produced by enzymatic cleavage or by recombinant techniques. For example, papain or pepsin cleavage can generate Fab or F(ab')$_2$ fragments, respectively. Other proteases with the requisite substrate specificity can also be used to generate Fab or F(ab')$_2$ fragments.

The antibodies that are included in the compositions of the invention include single chain antibodies, and recombinant antibodies, such as chimeric, humanized, primatized (CDR-grafted) or veneered antibodies, as well as chimeric, CDR-grafted or veneered single chain antibodies, comprising portions derived from different species. In addition, as described herein, the antibodies of the invention also include human antibodies, which can be generated, e.g., as described herein. Methods for the preparation of such various types of antibodies and antigen-binding fragments are described herein and/or are known in the art.

The invention provides for polyclonal and monoclonal antibodies that selectively bind to HMGB1, selectively bind to an HMGB1 B box polypeptide, and/or selectively bind to an HMGB A box polypeptide. Polyclonal antibodies raised against HMGB are known (see, for example, U.S. Pat. No. 6,468,555 B1, the entire teachings of which are incorporated herein by reference). These polyclonal antibodies have been shown to inhibit release of a proinflammatory cytokine from a cell, and to treat inflammation.

The term "monoclonal antibody" or "monoclonal antibody composition," as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

In one embodiment, the pharmaceutical composition comprises a monoclonal antibody or antigen-binding fragment thereof that binds to an HMGB1 polypeptide. Monoclonal antibodies to HMGB1 are known in the art, and are taught, for example, in WO 2005/026209 and U.S. Provisional Application No. 60/502,568, entitled "Monoclonal Antibodies Against HMGB1", by Walter Newman, Shixin Qin, Theresa O'Keefe and Robert Obar, filed on Sep. 11, 2003, the entire teachings of both of which are incorporated herein by reference. Particular monoclonal antibodies to HMGB 1 include, e.g., 6E6 HMGB1 mAb, 2E11 HMGB1 mAb, 6H9 HMGB1 mAb, 10D4 HMGB1 mAb and 2G7 HMGB1 mAb.

6E6 HMGB1 mAb, also referred to as 6E6-7-1-1 or 6E6, can be produced by murine hybridoma 6E6 HMGB1 mAb, which was deposited on Sep. 3, 2003, on behalf of Critical Therapeutics, Inc., 675 Massachusetts Avenue, 14$^{th}$ Floor, Cambridge, Mass. 02139, U.S.A., at the American Type Culture Collection, 10801 University Boulevard, Manassas, Va. 20110, U.S.A., under Accession No. PTA-5433.

2E11 HMGB1 mAb, also referred to as 2E11-1-1-2 or 2E11, can be produced by murine hybridoma 2E11 HMGB1 mAb, which was deposited on Sep. 3, 2003, on behalf of Critical Therapeutics, Inc., 675 Massachusetts Avenue, 14$^{th}$ Floor, Cambridge, Mass. 02139, U.S.A., at the American Type Culture Collection, 10801 University Boulevard, Manassas, Va. 20110, U.S.A., under Accession No. PTA-5431.

6H9 HMGB1 mAb, also referred to as 6H9-1-1-2 or 6H9, can be produced by murine hybridoma 6H9 HMGB1 mAb, which was deposited on Sep. 3, 2003, on behalf of Critical Therapeutics, Inc., 675 Massachusetts Avenue, 14$^{th}$ Floor, Cambridge, Mass. 02139, U.S.A., at the American Type Culture Collection, 10801 University Boulevard, Manassas, Va. 20110, U.S.A., under Accession No. PTA-5434.

10D4 HMGB1 mAb, also referred to as 10D4-1-1-1-2 or 10D4, can be produced by murine hybridoma 10D4 HMGB1 mAb, which was deposited on Sep. 3, 2003, on behalf of Critical Therapeutics, Inc., 675 Massachusetts Avenue, 14$^{th}$ Floor, Cambridge, Mass. 02139, U.S.A., at the American Type Culture Collection, 10801 University Boulevard, Manassas, Va. 20110, U.S.A., under Accession No. PTA-5435.

2G7 HMGB1 mAb, also referred to as 3-2G7-1-1-1 or 2G7, can be produced by murine hybridoma 2G7 HMGB1 mAb, which was deposited on Sep. 3, 2003, on behalf of Critical Therapeutics, Inc., 675 Massachusetts Avenue, 14$^{th}$ Floor, Cambridge, Mass. 02139, U.S.A., at the American Type Culture Collection, 10801 University Boulevard, Manassas, Va. 20110, U.S.A., under Accession No. PTA-5432.

Compositions Comprising RAGE-Ig Fusion Protein and Other Agents

Other agents that can be included in the compositions described herein include, e.g., Vitaxin™ and other antibodies targeting αvβ3 integrin (see, e.g., U.S. Pat. No. 5,753,230, PCT Publication Nos. WO 00/78815 and WO 02/070007; the entire teachings of all of which are incorporated herein by reference) and anti-IL-9 antibodies (see, e.g., PCT Publication No. WO 97/08321; the entire teachings of which are incorporated herein by reference).

Nucleic Acids

In one embodiment, the invention is drawn to nucleic acids encoding the RAGE-Ig fusion proteins described herein. The nucleic acids of the invention also encompass nucleic acids that encode ligand-binding variants of the RAGE-Ig fusion proteins of the invention. In particular embodiments, the ligand-binding variants of the RAGE-Ig fusion protein bind HMGB1 or a RAGE-binding fragment thereof (e.g., an HMGB1 A box, an HMGB1 B Box, a RAGE-binding peptide fragment of HMGB1). Ligand-binding variant nucleotide sequences include sequences that differ by one or more nucleotide substitutions, additions and/or deletions, such as allelic variants. Such variant nucleotide sequences include variants encoding altered RAGE and/or immunoglobulin element domains. In certain embodiments, the ligand-binding variant nucleotide sequence is at least 80% identical, 90% identical, 95% identical, 97% identical, or 99% identical, to the reference RAGE-Ig nucleotide sequence (e.g., SEQ ID NO:5; see FIG. 3A). Methods of determining % identity are known in the art and are described herein.

In other embodiments, the ligand-binding variant nucleotide sequences include nucleotide sequences that hybridize to the reference RAGE-Ig nucleotide sequence (e.g., SEQ ID NO:5) under selective hybridization conditions (e.g., highly stringent hybridization conditions). As used herein, the terms "hybridizes under low stringency", "hybridizes under medium stringency", "hybridizes under high stringency", or "hybridizes under very high stringency conditions", describes conditions for hybridization and washing of the nucleic acid sequences. Guidance for performing hybridization reactions can be found in Current Protocols in Molecular Biology (1989) John Wiley & Sons, N.Y., 6.3.1-6.3.6, which is incorporated herein by reference. Aqueous and nonaqueous methods are described in that reference and either can be used. For applications that require high selectivity, one will typically desire to employ relatively high stringency conditions to form hybrids. In solutions used for some membrane based hybridizations, addition of an organic solvent, such as formamide, allows the reaction to occur at a lower temperature. High stringency conditions are, for example, relatively low salt and/or high temperature conditions, such as are provided by about 0.02 M to about 0.10 M NaCl at temperatures of about 50° C. to about 70° C. High stringency conditions allow for limited numbers of mismatches between the two sequences. In order to achieve less stringent conditions, the salt concentration may be increased and/or the temperature may be decreased. For example, medium stringency conditions could be achieved at a salt concentration of about 0.1 to 0.25 M NaCl and a temperature of about 37° C. to about 55° C., while low stringency conditions could be achieved at a salt concentration of about 0.15 M to about 0.9 M NaCl, and a temperature ranging from about 20° C. to about 55° C. Selection of components and conditions for hybridization are well known to those skilled in the art and are reviewed in Ausubel et al. (1997, Short Protocols in Molecular Biology, John Wiley & Sons, New York N.Y., Units 2.8-2.11, 3.18-3.19 and 4.6-4.9).

In other embodiments, the present invention is an expression vector that comprises a nucleic acid of the invention (e.g., a nucleic acid encoding a RAGE-Ig fusion protein). In the expression vectors, the nucleic acid encoding the RAGE-Ig fusion protein is operably linked to at least one regulatory sequence. As used herein, "operably linked" means that the nucleotide sequence is linked to a regulatory sequence in a manner that allows for expression of the nucleotide sequence. Regulatory sequences are art-recognized and are selected to direct expression of the fusion polypeptide. Accordingly, the term "regulatory sequence" includes promoters, enhancers and other expression control elements. Exemplary regulatory sequences are described in Goeddel; Gene Expression Technology: Methods in Enzymology, Academic Press, San Diego, Calif. (1990).

Such useful expression control sequences, include, for example, the early and late promoters of SV40, tet promoter, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the copy number of the expression vector, the ability to control that copy number and the expression of any other protein encoded by the vector, such as an antibiotic marker, should also be considered. As exemplified herein, the use of an expression vector comprising a nucleic acid encoding a RAGE-Ig fusion protein can be can be used to express the RAGE-Ig fusion protein.

This invention also pertains to a cell (e.g., a host cell) that is transfected with a recombinant gene comprising a nucleotide sequence encoding a RAGE-Ig fusion protein of the invention. The host cell may be any prokaryotic or eukaryotic cell. For example, a polypeptide of the present invention may be expressed in bacterial cells, such as E. coli, insect cells (e.g., using a baculovirus expression system), yeast, or mammalian cells. As exemplified herein, a particular mammalian cell that can be transfected is a Chinese hamster ovary cell (CHO cell). Other suitable host cells are known to those skilled in the art.

In another embodiment, the invention is a method of producing a RAGE-Ig fusion protein. For example, a host cell transfected with an expression vector encoding a RAGE-Ig fusion protein can be cultured under appropriate conditions to allow expression of the RAGE-Ig fusion protein to occur. The RAGE-Ig fusion protein may be secreted and isolated from a mixture of cells and medium containing the RAGE-Ig fusion protein.

The RAGE-Ig fusion protein may be retained cytoplasmically, in which case, the cells can be harvested, lysed and the protein isolated. Suitable media for cell culture are well known in the art. The RAGE-Ig fusion protein can be isolated from cell culture medium, host cells, or both, using techniques known in the art for purifying proteins, e.g., ion-exchange chromatography, gel filtration chromatography, ultrafiltration, electrophoresis, and immunoaffinity purification using antibodies that are specific for particular epitopes of the RAGE-Ig fusion protein (e.g., a RAGE antibody, an Ig antibody). In a particular embodiment, the RAGE-Ig fusion protein contains an epitope that facilitates its purification (e.g., a GST moiety, a hexahistidine moiety).

In one embodiment, the invention is a method of producing a fusion protein comprising culturing a cell (e.g., a host cell) that comprises a nucleic acid encoding a RAGE-Ig fusion protein, in a cell culture medium suitable for expression of the fusion protein. In another embodiment, the method further comprises a purification procedure in order to increase the purity of the isolated RAGE-Ig fusion protein.

As exemplified herein, a RAGE-Ig fusion protein can be produced by ligating the relevant cloned genes, or portions thereof, into a vector suitable for expression in either prokaryotic cells, eukaryotic cells, or both. Expression vehicles for production of a recombinant fusion protein include plasmids and other vectors that are known to those of skill in the art. Suitable expression systems for both prokaryotic and eukaryotic cells, as well as general procedures for generating recombinant proteins, are described in Molecular Cloning: A Laboratory Manual, 2nd Ed., ed. by Sambrook, Fritsch and Maniatis (Cold Spring Harbor Laboratory Press, 1989), Chapters 16 and 17.

As exemplified herein, techniques for making fusion genes are well known. The joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In one embodiment, the nucleic acid encoding the RAGE-Ig fusion protein can be synthesized by conventional techniques, including automated DNA synthesizers. Alternatively, PCR amplification of gene fragments can be carried out as exemplified herein.

In one embodiment, the nucleic acid encoding a RAGE-Ig fusion protein comprises the nucleotide sequence depicted as SEQ ID NO:5. In another embodiment, the nucleic acid encodes a RAGE-Ig fusion protein comprising the amino acid sequence depicted in SEQ ID NO:6.

Methods of Treatment

In one embodiment, the invention is a method of treating a condition characterized by activation of the inflammatory cytokine cascade in a subject, comprising administering an effective amount of a RAGE-Ig fusion protein and/or a composition (e.g., pharmaceutical composition) comprising a RAGE-Ig fusion protein. An inflammatory condition that is suitable for the methods of treatment described herein can be one in which the inflammatory cytokine cascade is activated. In one embodiment, the inflammatory cytokine cascade causes a systemic reaction, such as with endotoxic shock. In another embodiment, the inflammatory condition is mediated by a localized inflammatory cytokine cascade, as in rheumatoid arthritis. Nonlimiting examples of inflammatory conditions that can be usefully treated using the RAGE-Ig fusion proteins and/or compositions of the present invention include, e.g., diseases involving the gastrointestinal tract and associated tissues (such as ileus, appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, coeliac disease, hepatitis, Crohn's disease, enteritis, and Whipple's disease); systemic or local inflammatory diseases and conditions (such as asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, and sarcoidosis); diseases involving the urogenital system and associated tissues (such as septic abortion, epididymitis, vaginitis, prostatitis, and urethritis); diseases involving the respiratory system and associated tissues (such as bronchitis, emphysema, rhinitis, cystic fibrosis, pneumonitis, adult respiratory distress syndrome, pneumoultramicroscopicsilicovolcanoconiosis, alvealitis, bronchiolitis, pharyngitis, pleurisy, and sinusitis); diseases arising from infection by various viruses (such as influenza, respiratory syncytial virus, HIV, hepatitis B virus, hepatitis C virus and herpes), bacteria (such as disseminated bacteremia, Dengue fever), fingi (such as candidiasis) and protozoal and multicellular parasites (such as malaria, filariasis, amebiasis, and hydatid cysts); dermatological diseases and conditions of the skin (such as burns, dermatitis, dermatomyositis, sunburn, urticaria warts, and wheals); diseases involving the cardiovascular system and associated tissues (such as stenosis, restenosis, vasulitis, angiitis, endocarditis, arteritis, atherosclerosis, thrombophlebitis, pericarditis, congestive heart failure, myocarditis, myocardial ischemia, periarteritis nodosa, and rheumatic fever); diseases involving the central or peripheral nervous system and associated tissues (such as Alzheimer's disease, meningitis, encephalitis, multiple sclerosis, cerebral infarction, cerebral embolism, Guillame-Barre syndrome, neuritis, neuralgia, spinal cord injury, paralysis, and uveitis); diseases of the bones, joints, muscles and connective tissues (such as the various arthritides and arthralgias, osteomyelitis, fasciitis, Paget's disease, gout, periodontal disease, rheumatoid arthritis, and synovitis); other autoimmune and inflammatory disorders (such as myasthenia gravis, thryoiditis, systemic lupus erythematosus, Goodpasture's syndrome, Behcets's syndrome, allograft rejection, graft-versus-host disease, Type I diabetes, ankylosing spondylitis, Berger's disease, and Retier's syndrome); as well as various cancers, tumors and proliferative disorders (such as Hodgkins disease); and, in any case the inflammatory or immune host response to any primary disease.

In one embodiment, the condition is selected from the group consisting of sepsis, allograft rejection, arthritis (e.g., rheumatoid arthritis), asthma, atherosclerosis, restenosis, lupus, adult respiratory distress syndrome, chronic obstructive pulmonary disease, psoriasis, pancreatitis, peritonitis, burns, myocardial ischemia, organic ischemia, reperfusion ischemia, Behcet's disease, graft versus host disease, Crohn's disease, ulcerative colitis, ileus, multiple sclerosis, and cachexia. In another embodiment, the condition is selected from the group consisting of sepsis, arthritis (e.g., rheumatoid arthritis), asthma, lupus, psoriasis, inflammatory bowel disease and Crohn's disease.

Preferably the RAGE-Ig fusion proteins and compositions of the invention are administered to a patient in need thereof in an amount sufficient to inhibit release of proinflammatory cytokine from a cell and/or to treat an inflammatory condition. In one embodiment, release of the proinflammatory cytokine is inhibited by at least 10%, 20%, 25%, 50%, 75%, 80%, 90%, or 95%, as assessed using methods described herein or other methods known in the art.

The terms "therapy", "therapeutic" and "treatment" as used herein, refer to ameliorating symptoms associated with a disease or condition, for example, an inflammatory disease or an inflammatory condition, including preventing or delaying the onset of the disease symptoms, and/or lessening the severity or frequency of symptoms of the disease or condition. The terms "patient", "subject" and "individual" are defined herein to include humans and animals, such as mammals, including, but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human.

In addition to being involved in various inflammatory conditions (e.g., inflammatory conditions described herein), RAGE and its ligands play a role in the pathophysiology of other RAGE-related conditions or disorders (Schmidt, A. et al., *J. Clin. Invest.* 108:949-955 (2001)). RAGE-related conditions or disorders may be characterized generally as including any disorder in which an affected cell exhibits elevated expression of RAGE and/or one or more RAGE ligands. RAGE-related conditions or disorders may also be characterized as any disorder that is treatable (i.e., one or more symptoms may be eliminated or ameliorated) by a decrease in RAGE function. RAGE function can be decreased by administering an agent that disrupts the interaction between RAGE and one or more of its ligands. Increased expression of RAGE is associated with several pathological states, including diabetic vasculopathy, nephropathy, retinopathy, neuropathy, and other disorders, including Alzheimer's disease and immune/inflammatory reactions of blood vessel walls. RAGE ligands are produced in tissue affected with many inflammatory disorders, including arthritis (e.g., rheumatoid arthritis). In diabetic tissues, the production of RAGE is thought to be caused by the overproduction of advanced glycation endproducts (AGEs). This overproduction results in oxidative stress and endothelial cell dysfunction that leads to vascular disease in diabetics (WO 2004/016229; the entire teachings of which are incorporated herein by reference).

Deposition of amyloid in tissues causes a variety of toxic effects on cells and is characteristic of a number of diseases that may be termed amyloidoses. RAGE binds to beta-sheet fibrillar material, such as that found in amyloid-beta peptide, Abeta, amylin, serum amyloid A and prion-derived peptides. Increased expression of RAGE is also observed in tissues having amyloid structures. Accordingly, RAGE is involved in amyloid disorders. The RAGE-amyloid interaction is thought to result in oxidative stress leading to neuronal degeneration (WO 2004/016229).

A variety of RAGE ligands, and particularly those of the S 100/calgranulin family, are produced in inflamed tissues. This observation is true both for acute inflammation, such as that seen in response to a lipopolysaccharide challenge (as in sepsis), and for chronic inflammation. Cardiovascular diseases, particularly those arising from atherosclerotic plaques, are thought to have a substantial inflammatory component and therefore can be treated using the RAGE-Ig fusion proteins or compositions of the invention. Such cardiovascular diseases include, e.g., occlusive, thrombotic and embolic diseases, such as angina, fragile plaque disorder and embolic stroke, respectively, as well as the other cardiovascular diseases described herein.

Tumor cells also exhibit an increased expression of RAGE ligand, particularly HMGB1. In addition, the oxidative effects and other aspects of chronic inflammation may have a contributory effect to the genesis of certain tumors. Therefore, in one embodiment, the invention is a method of treating a cancer comprising administering the RAGE-Ig fusion proteins or compositions of the invention.

As described, in certain embodiments, the present invention provides for the administration of the subject RAGE-Ig fusion proteins. The RAGE-Ig fusion proteins can be administered, in vitro or in vivo, and expression of the subject fusion proteins can be achieved by administering the RAGE-Ig fusion proteins directly and/or by administering nucleic acids encoding the RAGE-Ig fusion proteins. As described herein, in certain embodiments, the RAGE-Ig fusion proteins or nucleic acids are administered as compositions (e.g., pharmaceutical compositions).

Methods for delivering nucleic acids such that they express their encoded proteins (e.g., a nucleic acid encoding a RAGE-Ig fusion protein) are known in the art, and include, e.g., expression from viral vectors (e.g., recombinant retroviruses, adenovirus, adeno-associated virus, herpes simplex virus-1, lentivirus) and use of recombinant bacterial or eukaryotic plasmids. As described herein, suitable routes of administration and dosages of the RAGE-Ig fusion proteins, nucleic acids and/or compositions of the invention, depend on a variety of factors and can be determined by the skilled artisan without undue experimentation.

Antibodies to RAGE-Ig Fusion Proteins and Antibodies to RAGE Fragments

In one embodiment, the invention is an antibody or antigen-binding fragment thereof that specifically binds to a RAGE-Ig fusion protein. In one embodiment, the antibody or antigen-binding fragment can specifically bind one or more epitopes that are present in a RAGE-Ig fusion protein but are not present in either of the parent RAGE or Ig proteins.

In another embodiment, the invention is an antibody or antigen-binding fragment thereof that specifically binds to a RAGE fragment but does not bind to the entire RAGE protein. Such antibodies recognize one or more epitopes that are present in the RAGE fragment, but are not present or accessible in the full-length RAGE protein. In a particular embodiment, the antibody or antigen-binding fragment thereof specifically binds to a RAGE fragment consisting of amino acid residue 19 to about amino acid residue 305 of SEQ ID NO:2.

Methods for making antibodies (e.g., polyclonal antibodies, monoclonal antibodies) to RAGE-Ig fusion proteins are known in the art. A variety of methods have been described (see e.g., Kohler et al., *Nature*, 256: 495-497 (1975) and *Eur. J. Immunol.* 6: 511-519 (1976); Milstein et al., *Nature* 266: 550-552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line such as SP2/0, P3X63Ag8.653 or a heteromyloma) with antibody-producing cells. Antibody-producing cells can be obtained from the peripheral blood or, preferably the spleen or lymph nodes, of humans or other suitable animals immunized with the antigen of interest. The fused cells (hybridomas) can be isolated using selective culture conditions, and cloned by limiting dilution. Cells that produce antibodies with the desired specificity can be selected by a suitable assay (e.g., ELISA).

Other suitable methods of producing or isolating antibodies of the requisite specificity (e.g., specificity for a RAGE-Ig fusion protein) can be used, including, for example, methods which select recombinant antibody from a library (e.g., a phage display library). Transgenic animals capable of producing a repertoire of human antibodies (e.g., Xenomouse® (Abgenix, Fremont, Calif.)) can be produced using suitable methods (see e.g., Jakobovits et al., *Proc. Natl. Acad. Sci. USA*, 90: 2551-2555 (1993); Jakobovits et al., *Nature*, 362: 255-258 (1993)). Additional methods that are suitable for production of transgenic animals capable of producing a repertoire of human antibodies have been described (e.g., Lonberg et al., U.S. Pat. No. 5,545,806; Surani et al., U.S. Pat. No. 5,545,807; Lonberg et al., WO97/13852).

Antibodies that specifically bind a RAGE-Ig fusion protein include, e.g., single chain antibodies, and recombinant antibodies, such as chimeric, humanized, primatized (CDR-grafted) or veneered antibodies, as well as chimeric, CDR-grafted or veneered single chain antibodies, comprising portions derived from different species. As described herein, antigen-binding fragments include, but are not limited to Fv, Fab, Fab' and F(ab')$_2$ fragments.

Antibodies to HMGB1 Fragments

In one embodiment, the invention is an antibody or antigen-binding fragment thereof that specifically binds to a fragment of HMGB1, wherein the fragment of HMGB1 comprises one or more binding sites for RAGE. As exemplified herein, RAGE binds to two regions of HMGB1 (Example 11). The first region of HMGB1, which comprises a binding site for RAGE, is a portion of the A box within amino acids 31 to 78. The second region that comprises a binding site for RAGE is a portion of the B box within amino acids 121 to 168 (or a portion of the B box within amino acids 121 to 158). Given the importance of RAGE and HMGB1 in a number of significant human disorders (e.g., as described herein), the present invention encompasses antibodies that bind to one or both of these regions of HMGB1.

Thus, in one embodiment, the invention is an antibody or antigen-binding fragment thereof that inhibits binding of HMGB1 to RAGE, and binds to a fragment of an HMGB1 protein consisting of amino acids 31 to 78. In another embodiment, the invention is an antibody or antigen-binding fragment thereof that inhibits binding of HMGB1 to RAGE, and binds to a fragment of an HMGB1 protein consisting of amino acids 31 to 78 of SEQ ID NO:11. In another embodiment, the invention is an antibody or antigen-binding fragment thereof that inhibits binding of HMGB1 to RAGE, and binds to a fragment of an HMGB1 protein consisting of amino acids 31 to 78 of SEQ ID NO:12.

Monoclonal antibodies that bind to this region of HMGB1 are taught in WO 2005/026209 and U.S. Provisional Application No. 60/502,568, filed on Sep. 11, 2003. For example, 6E6 HMGB1 mAb and 6H9 HMGB1 mAb bind to a peptide corresponding to amino acid residues 61-78 of human HMGB1 (i.e., amino acid residues 61-78 of SEQ ID NO:11). 2G7 HMGB1 mAb binds to a peptide corresponding to amino acid residues 46-63 of human HMGB1 (i.e., amino acid residues 46-63 of SEQ ID NO:11).

In particular embodiments, the invention is an antibody or antigen-binding fragment thereof that inhibits binding of HMGB1 to RAGE, and binds to a fragment of an HMGB1 protein consisting of amino acids 121 to 158 or amino acids 121 to 168. In other embodiments, the invention is an antibody or antigen-binding fragment thereof that inhibits binding of HMGB1 to RAGE, and binds to a fragment of an HMGB1 protein consisting of amino acids 121 to 158 of SEQ ID NO:11 or amino acids 121 to 168 of SEQ ID NO:11. In still other embodiments, the invention is an antibody or antigen-binding fragment thereof that inhibits binding of HMGB1 to RAGE, and binds to a fragment of an HMGB1 protein consisting of amino acids 121 to 158 of SEQ ID NO:12 or amino acids 121 to 168 of SEQ ID NO:12.

Monoclonal antibodies that bind to this region of HMGB1 are taught in WO 2005/026209 and U.S. Provisional Application No. 60/502,568, filed on Sep. 11, 2003. For example, 2E11 HMGB1 mAb binds to a peptide corresponding to amino acid residues 151-168 of human HMGB1 (i.e., amino acid residues 151-168 SEQ ID NO:11).

In another embodiment, the invention is an antibody or antigen-binding fragment thereof that inhibits binding of HMGB1 to RAGE, and binds to both a fragment of an HMGB1 protein consisting of amino acids 31 to 78 and a fragment of an HMGB protein consisting of amino acids 121 to 158 or amino acids 121 to 168.

Suitable methods of producing and/or isolating antibodies of the requisite specificity (e.g., specificity for a peptide consisting of amino acid residues 31 to 78, 121 to 158 and/or 121 to 168 of human HMGB1 (SEQ ID NO:11)) are described herein and/or are known in the art. Similarly, various types of antibodies and antigen-binding fragments are also described herein and/or are known in the art.

The discovery of particular binding sites in HMGB1 (e.g., amino acids 31 to 78, 121 to 158, and 121 to 168 of human HMGB1) for RAGE allows for screening of antibodies that can block HMGB1 function (e.g., HMGB 1-mediated activation of the cytokine cascade). Thus, in one embodiment, the invention is a method of screening for an agent that modifies (e.g., inhibits, enhances) the interaction of HMGB1 and RAGE or a ligand binding fragment thereof (e.g., as described herein). In the methods, a peptide corresponding to one or both of the regions of HMGB1 that bind RAGE (e.g., amino acids 31 to 78 and 121 to 158 (or 121 to 168) of human HMGB1), RAGE or a ligand-binding fragment thereof, and an agent are combined under conditions suitable for interaction of the HMGB1 peptide and RAGE. The binding that occurs between the HMGB1 fragment and RAGE is determined and compared to that which occurs in the absence of the agent. In this type of assay, a decrease in the amount of RAGE-HMGB1 peptide complex that is formed in the presence of the agent indicates that the agent inhibits the interaction. An increase in the amount of RAGE-HMGB1 peptide complex that is formed in the presence of the agent indicates that the agent enhances the interaction of HMGB1 and RAGE. In one embodiment, the HMGB1 peptide and/or RAGE protein can be labeled. Suitable labels for labeling HMGB1 peptides and/or RAGE proteins or ligand-binding fragments thereof include, for example, a radioisotope, an epitope label (tag), an affinity label (e.g., biotin, avidin), a spin label, an enzyme, a fluorescent group or a chemiluminescent group.

A variety of agents, such as proteins (e.g., antibodies), peptides, peptidomimetics, small organic molecules, nucleic acids and the like, can be tested for binding to an HMGB peptide (e.g., a peptide consisting of amino acids 31 to 78, 121 to 158, or 121 to 168 of human HMGB1) and/or RAGE. According to the methods of the present invention, agents can be individually screened or one or more agents can be tested simultaneously. Where a mixture of compounds is tested, the compounds selected by the processes described can be separated (as appropriate) and identified using suitable methods (e.g., sequencing, chromatography). The presence of one or more compounds (e.g., an inhibitor, a promoter) in a test sample can also be determined according to these methods.

Agents that bind to an HMGB peptide (e.g., a peptide consisting of amino acids 31 to 78, 121 to 158, or 121 to 168 of human HMGB1) and/or RAGE, and which are useful in the compositions and/or methods described herein can be identified, for example, by screening libraries or collections of molecules, such as, the Chemical Repository of the National Cancer Institute, in assays described herein or using other suitable methods. Libraries, such as combinatorial libraries, of compounds (e.g., organic compounds, recombinant or synthetic peptides, "peptoids", nucleic acids) produced by combinatorial chemical synthesis or other methods can be tested (see e.g., Zuckerman, R. N. et al., *J. Med. Chem.*, 37: 2678-2685 (1994) and references cited therein; see also, Ohlmeyer, M. H. J. et al., *Proc. Natl. Acad. Sci. USA* 90:10922-10926 (1993) and DeWitt, S. H. et al., *Proc. Natl. Acad. Sci. USA* 90:6909-6913 (1993), relating to tagged compounds; Rutter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a library carry unique tags, identification of individual compounds by chromatographic methods is possible.

EXEMPLIFICATION

EXAMPLE 1

Construction of Human IgG1 Heavy-Chain Gene Polyadenylation Signal Sequence 1 ("IGPA")

A human IgG1 heavy-chain gene polyadenylation signal sequence was assembled by PCR using the overlapping primers designated pIGPA5 (SEQ ID NO:15) and pIGPA3 (SEQ ID NO:16) in Table 1 below.

Briefly, primers were combined in various molar ratios in a cycler reaction of 1 step at 94° C. for 2 minutes, followed by 8 cycles at 94° C. for 2 minutes and 5 minutes at 72° C. with a 30 second ramp time between each step, followed by a step at 72° C. for 10 minutes. The product ("cIGPA") obtained was then used as a template for the final amplification reaction.

The IGPA sequence was amplified using cIGPA as a template. cIGPA was combined with the overlapping primers designated pIGPA5a (SEQ ID NO:17) and pIGPA3a (SEQ ID NO:18) in Table 1. A standard amplification cycle of 1 step at 94° C. for 2 minutes, followed by 30 cycles at 94° C. for 1 minute, 55° C. for 30 seconds and 72° C. for 5 minutes, followed by a step at 72° C. for 10 minutes was used. The complete IGPA nucleotide sequence (SEQ ID NO:19; shown below) is 187 base pairs in length and was used in the final expression vector and as a template for the 5' region for IgG1 heavy-chain gene polyadenylation signal sequence 2 (LIGPA).

IGPA (Lower Case Indicates Cloning Sites)

```
                                              (SEQ ID NO:19)
5' gctctagaGTGCGACGGCCGGCAAGCCCCCGCTCCCCGGGCTCTCGC

GGTCGCACGAGGATGCTTGGCACGTACCCCCTGTACATACTTCCCGGGCG

CCCAGCATGGAAATAAAGCACCCAGCGCTGCCCTGGGCCCCTGCGAGACT

GTGATGGTTCTTTCCACGGGTCAGgcggccgctaaactat 3'
```

TABLE 1

Oligonucleotide Primers used to Create Polyadenylation Signal IGPA

| Primer | Sequence | SEQ ID |
|---|---|---|
| pIGPA5 | 5'CGGCCGGCAAGCCCCCGCTCCCCGGGCTCTC GCGGTCGCACGAGGATGCTTGGCACGTACCCC CTGTACATACTTCCCGGGCGCCCAGC 3' | SEQ ID NO:15 |
| pIGPA3 | 5'AAGAACCATCACAGTCTCGCAGGGGCCCAGG GCACGGCTGGGTGCTTTATTTCCATGCTGGGCG CCCGGGAAGTATGTAC 3' | SEQ ID NO:16 |
| pIGPA5a | 5'GCTCTAGAGTGCGACGGCCGGCAAGCCCCCG CTCCCCGGGCTC 3' | SEQ ID NO:17 |
| pIGPA3a | 5'ATAGTTTAGCGGCCGCCTGACCCGTGGAAAG AACCATCACAGTCTCGCAG 3' | SEQ ID NO:18 |

EXAMPLE 2

Construction of Human IgG1 Heavy-Chain Gene Polyadenylation Signal Sequence 2 ("LIGPA")

A second human IgG1 heavy-chain gene polyadenylation signal sequence was assembled by PCR using the overlapping primers designated as pLIGPA5 (SEQ ID NO:20 and pLIGPA3 (SEQ ID NO:21 in Table 2 below).

Briefly, these primers were combined in various molar ratios in a cycler reaction of 1 step at 94° C. for 2 minutes, followed by 8 cycles at 94° C. for 2 minutes and 72° C. for 5 minutes with a 30 second ramp time between each step, followed by a step at 72° C. for 10 minutes. The product ("cLIGPA3") obtained was then used as a template for the amplification reaction for the 3' region of LIGPA.

The 5' region of the LIGPA sequence ("LIGPA5i") was amplified using IGPA as a template combined with the overlapping primers designated pIGPA5a (SEQ ID NO:17) in Table 1 and pLIGPA5b (SEQ ID NO:23) in Table 2 below. The 3' region of LIGPA ("LIGPA3i") was obtained using cLIGPA3 as a template combined with the overlapping primers designated pLIGPA5a (SEQ ID NO:22) and pLIGPA3a (SEQ ID NO:24) in Table 2 below. Standard amplification cycles of 94° C. for 2 minutes, followed by 30 cycles at 94° C. for 1 minute, 55° C. for 30 seconds and 72° C. for 5 minutes, followed by a step at 72° C. for 10 minutes, were used.

The products of the above two reactions (LIGPA5i and LIGPA3i) were combined in various molar ratios in a cycler reaction at 94° C. for 2 minutes, followed by 8 cycles at 94° C. for 2 minutes and 72° C. for 5 minutes with a 30 second ramping time before each step, followed by a step at 72° C. for 10 minutes. The product of this reaction ("cLIGPA") served as a template for the final amplification reaction of LIGPA.

The complete LIGPA was amplified using cLIGPA as a template with the primers designated pLIGPA5a (SEQ ID NO:22) and pLIGPA3a (SEQ ID NO:24) in Table 2 below. A standard amplification cycle of one step at 94° C. for 2 minutes, followed by 30 cycles at 94° C. for 1 minute, 55° C. for 30 seconds and 72° C. for 5 minutes, followed by a step at 72° C. for 10 minutes, was used. The product LIGPA (SEQ ID NO:34) (shown directly below) is 347 base pairs in length and is used in the final expression vector.

LIGPA (Lower Case Indicates Cloning Sites)

(SEQ ID NO:34)
```
5' gctctagaGTGCGACGGCCGGCAAGCCCCCGCTCCCCGGGCTCTCGC
GGTCGCACGAGGATGCTTGGCACGTACCCCCTGTACATACTTCCCGGGCG
CCCAGCATGGAAATAAAGCACCCAGCGCTGCCCTGGGCCCCTGCGAGACT
GTGATGGTTCTTTCCACGGGTCAGGCCGAGTCTGAGGCCTGAGTGGCATG
AGGGAGGCAGAGCGGGTCCCACTGTCCCCACACTGGCCCAGGCTGTGCAG
GTGTGCCTGGGCCCCCTAGGGTGGGGCTCAGCCAGGGGCTGCCCTCGGCA
GGGTGGGGGATTTGCCAGCGTGGCCCTCCCTCCAgcggccgctaaactat
3'
```

TABLE 2

Oligonucleotide Primers Used to Create Polyadenylation Signal LIGPA

| Primer | Sequence | SEQ ID NO: |
|---|---|---|
| pLIGPA5b | 5'GCCACTCAGGCCTCAGACTCGGCCTGACC CGTGGAAAGAACCATCACAGTCTCGC 3' | SEQ ID NO:23 |
| pLIGPA5 | 5'GTGGCATGAGGGAGGCAGAGCGGGTCCC ACTGTCCCCACACTGGCCCAGGCTGTGCAG GTGTGCCTGGGCCCCCTAG 3' | SEQ ID NO:20 |
| pLIGPA3 | 5'GGGAGGGCCACGCTGGCAAATCCCCCAC CCTGCCGAGGGCAGCCCCTGGCTGAGCCCC ACCCTAGGGGGCCCAGGCACACCTGCACAG C 3' | SEQ ID NO:21 |
| pLIGPA5a | 5'GGCCGAGTCTGAGGCCTGAGTGGCATGA GGGAGGCAGAGC 3' | SEQ ID NO:22 |
| pLIGPA3a | 5'ATAGTTTAGCGGCCGCTGGAGGGAGGGC CACGCTGGCAAATCC 3' | SEQ ID NO:24 |

EXAMPLE 3

Construction of Expression Vectors Comprising Either the IgG1 Heavy-Chain Gene Polyadenylation Signal Sequence 1 (pCTiTOK28) or the IgG1 Heavy-Chain Gene Polyadenylation Signal Sequence 2 (pCTiTOK29)

The mammalian expression vector pcDNA3 (Invitrogen, San Diego, Calif.) was first altered to replace the CMV promoter with the EF-1a promoter for higher protein expression. The pcDNA3 expression vector was also altered to add a NotI site downstream of the BGH polyadenylation signal sequence in order to allow for the addition of a second expression cassette. This altered vector is designated pCTiTOK18.

The BGH polyadenylation signal sequence of pCTi-TOK18, flanked by XbaI and NotI enzyme restriction sites, was removed and replaced with either the IGPA or the LIGPA polyadenylation signal sequences, which were created with flanking XbaI and NotI enzyme restriction sites. These mammalian expression vectors, which contain either the IGPA polyadenylation signal sequence or LIGPA polyadenylation signal sequences, are designated pCTiTOK28 and pCTi-TOK29, respectively.

The vectors pCTiTOK18, pCTiTOK28 and pCTiTOK29 all contain the gene for ampicillin selection in bacteria and geneticin (G418) selection in mammalian cells. The promoter, EF-1a, is separated from the polyadenylation signal sequences by a region of multiple cloning sites into which a desired cDNA may be functionally cloned.

EXAMPLE 4

RAGE-Ig Fusion Protein Production

The RAGE-Ig fusion protein (SEQ ID NO:6) was created by PCR assembly in which two overlapping cDNA fragments were created, annealed by PCR and used as a template for the final PCR product. The extracellular region of RAGE (e.g., amino acids 1-305 of GenBank Accession No. NP_001127; SEQ ID NO:2) along with its signal sequence was amplified using human splenic cDNA as a template and the primers designated pTOK16a5 (SEQ ID NO:25) and pTOK17aA (SEQ ID NO:26), described in Table 3 below. The primer pTOK16a5 (SEQ ID NO:25) contains the sequence for an EcoRI restriction site and a Kozak sequence. The primer pTOK17aA (SEQ ID NO:26) contains 35 bases that overlap with the 5' region of the human IgG1 Fc.

The human IgG1 Fc region was amplified from a previous human IgG1 fusion protein in which the Fc receptor region was removed by mutation (L235A and G237A; corresponding to EU numbering (Edelman, G. M. et al., *Proc. Natl. Acad. Sci. USA* 63:78-85 (1969)). The sequence used covered the hinge CH2 and CH3 regions (amino acids 101-329 of GenBank Accession No. J00228; SEQ ID NO:4) and was amplified using the primers pTOK17aB (SEQ ID NO:27) and pTOK10a3 (SEQ ID NO:28), described in Table 3 below. The primer pTOK17aB (SEQ ID NO:27) contains 35 nucleotides that overlapped with the 3' region of the extracellular region of RAGE and the primer pTOK10a3 (SEQ ID NO:28) contains a stop codon and the sequence for the XbaI restriction site. The PCR cycle involved 1 step at 94° C. for 2 minutes, followed by 30 cycles at 94° C. for 1 minute, 55° C. for 30 seconds and 72° C. for 5 minutes, followed by a step at 72° C. for 10 minutes. The two fragments were then gel purified and combined in equal molar ratios in a PCR reaction without primers that used a PCR cycle involving 1 step at 94° C. for 2 minutes, followed by 8 cycles at 94° C. for 2 minutes and 72° C. for 5 minutes with a 30-second ramping time at each step, followed by a step at 72° C. for 10 minutes. The product of this reaction then served as a template in another amplification reaction using the primers pTOK16a5 (SEQ ID NO:25) and pTOK10a3 (SEQ ID NO:28) with the same cycler steps used in the first amplification reaction. This product was TA-cloned and sequenced to find the correct cDNA construct. The product, a nucleotide construct encoding a RAGE-Ig fusion polypeptide, is described as SEQ ID NO:5, while the encoded RAGE-Ig fusion protein has the amino acid sequence depicted in SEQ ID NO:6.

The three expression vectors, pCTiTOK17 (BGHpA), pCTiTOK30 (IGPA) and pCTiTOK31 (LIGPA), containing the RAGE-Ig fusion cDNA were all created by functionally cloning the EcoRI-XbaI fragment containing the RAGE-Ig fusion cDNA into the vectors pCTiTOK18, pCTiTOK28 and pCTiTOK29, respectively. After the sequence of each was confirmed, DNA was maxiprepped and transfected into CHO cells as described below.

TABLE 3

Oligonucleotide Primers Used to Create a RAGE-Ig Fusion Construct

| Primer | Sequence | SEQ ID NO: |
|---|---|---|
| pTOK16a5 | 5'CCGGAATTCCTCACCATGGCAGCCGGAACA GCAGTTGGAG 3' | SEQ ID NO:25 |
| pTOK17aA | 5'GTTTTGTCGCTGGAATGGGTGGCCACACAG CTGTAGGTTCCCTGGTCCTGAG 3' | SEQ ID NO:26 |
| pTOK17aB | 5'GCTGTGTGGCCACCCATTCCAGCGACAAAA CTCACACATGCCCACCGTGCCCAGCACCTG 3' | SEQ ID NO:27 |
| pTOK10a3 | 5'TGCTCTAGATTATTTACCCGGAGACAGGGA GAGGCCTTCTGCGTGTAGTGGTTGTGCAGAG CCTCATGCATCACGG 3' | SEQ ID NO:28 |

EXAMPLE 5

Preparation of CHO Cell Transfectants

This example describes the transfection of CHO cells with the constructs pCTiTOK18, pCTiTOK28 and pCTiTOK29. CHO-S cells (Gibco/Invitrogen, Carlsbad, Calif.) were transfected according to the manufacturer's instructions using recommended reagents. Briefly, different concentrations of the expression vectors pCTiTOK18, pCTiTOK28 or pCTiTOK29, and the DMRIE-C reagent, a mixture of charged and neutral lipids, were mixed to form complexes for 30-45 minutes. These complexes were then mixed with the CHO cells in serum-free DMEM in the absence of antibiotics. The cells take up the complexes and incorporate the DNA into their chromosomes over the next 5 hours. The transfection was stopped by the addition of media containing 10% fetal bovine serum. The CHO cells were then allowed to recover and incubated at 37° C. overnight in 8% CO₂.

The successfully transfected cells were selected for growth in media containing 10% fetal bovine serum and 50 mg/ml geneticin for 5 days. Single cell clones were then plated into 96-well plates, isolated for the production of human IgG Fc containing protein, and selected for an additional 14 days. Single cell clones were then identified and their supernatants were tested for the presence of recombinant protein. Clones determined to be producing the recombinant protein were expanded and adapted to protein-free media (the clones may also be kept in 10% fetal bovine serum, however, the presence of serum increases the difficulty of purification). The CHO-S cells easily adapt to growth in Gibco/Invitrogen's protein-free CD-CHO media and shaker flask culture, which allows for rapid expansion of the cells. Cell culture media was then collected and the presence of RAGE-Ig fusion protein was determined as described below.

EXAMPLE 6

RAGE-Ig Fusion Protein Production by Cells Transfected with pCTiTOK17 (BGHpA), pCTiTOK30 (IGPA) and pCTiTOK31 (LIGPA)

The presence and quantity of RAGE-Ig fusion protein in the cell culture media of CHO cells transfected with either the expression vector pCTiTOK17, pCTiTOK30 or pCTiTOK31, was determined using a standardized ELISA. Briefly, ELISA plates were coated with 0.4 µg/ml of goat anti-human IgG (Jackson ImmunoResearch Laboratories, West Grove, Pa.) and incubated overnight at 4° C. The plates were then blocked with PBS containing 1% BSA for one hour at room temperature. After washing, the plates were incubated with the CHO cells supernatants obtained as described above. After 2 hours at room temperature, the plates were washed and incubated with mouse anti-human IgG-HRP (Jackson ImmunoResearch Laboratories, West Grove, Pa.) diluted at 1:2000 in PBS. After washing, the plates were developed with TMB (Invitrogen, San Diego, Calif.) and absorbance at 655 nm was measured using a plate reader. The amount of RAGE-Ig fusion protein was quantified by comparison to a standard dilution curve of human IgG (Jackson ImmunoResearch Laboratories, West Grove, Pa.). The results of this quantification is presented in FIG. 4. The protein may also be quantified using Western analysis and functional assays.

FIG. 4 shows the results of a preliminary experiment measuring the quantity of RAGE-Ig fusion protein (µg/ml) found in the supernatants of CHO cells transfected with pCTiTOK17, pCTiTOK30 or pCTiTOK31 (comprising the BGH, IGPA or LIGPA polyadenylation signal sequence, respectively). CHO cells transfected with pCTiTOK17 were cloned cells; consequently it was estimated that 100% of the cells were able to produce the RAGE-Ig fusion protein. The cells transfected with pCTiTOK30 and pCTiTOK31 were uncloned cells (i.e., primary pool of transfectants) cultured for 12 and 6 days, respectively. Because the latter cells are uncloned, it is estimated that less than 10% of the cells are able to produce the RAGE-Ig fusion protein. The two bars for the IGPA and LIGPA containing cells represent the results of two separate transfections. A greater quantity of recombinant protein in the supernatants indicates that the protein is properly folded and secreted from the cells, which is suggestive of proper polyadenylation. As shown in FIG. 4, the data suggest that cells transfected with an expression vector comprising either the IGPA or LIGPA polyadenylation signal sequence are able to produce the RAGE-Ig fusion protein.

Figure 5:
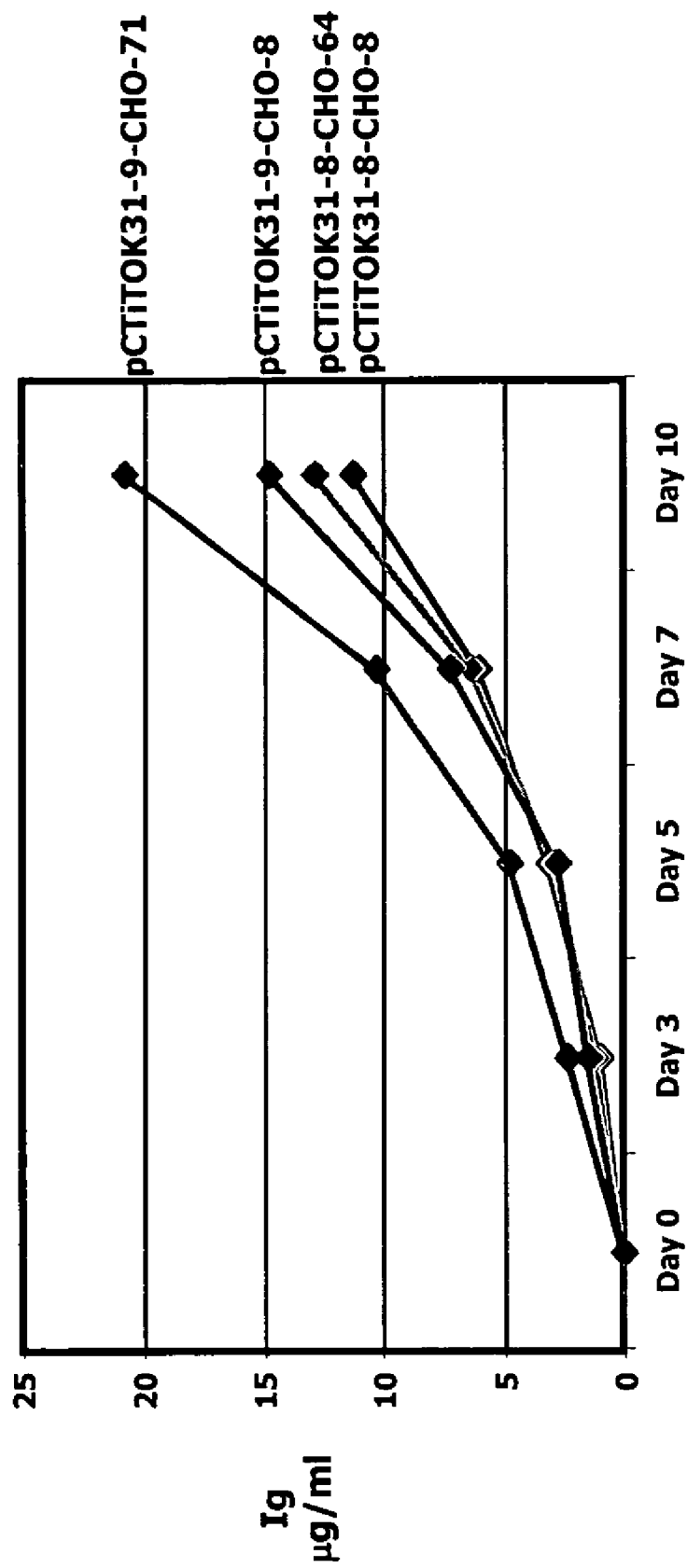
FIG. 5 is a graph comparing the quantity of RAGE-immunoglobulin fusion protein (μg/ml) in the supernatants of different CHO cell clones transfected with the mammalian expression vector pCTiTOK31, which contains the LIGPA polyadenylation signal sequence.

FIG. 5 shows the results of an experiment measuring the quantity of RAGE-Ig fusion protein (µg/ml) in the supernatants from four CHO cell clones transfected with the vector pCTiTOK31 (comprising LIGPA) over a 10 day period. On Day 0, the starting number of cells for each of the five clones was $1.3 \times 10^8$ cells in 750 ml of CD-CHO/G418. As shown in FIG. 5, the quantity of RAGE-Ig fusion protein produced by the cells increases over time and by the tenth day, the cells produce a quantity of RAGE-Ig fusion protein ranging from about 11 to 21 µg/ml.

EXAMPLE 7

RAGE-Ig Fusion Protein Binds Recombinant HMGB1

An ELISA was performed in order to determine whether the RAGE-Ig fusion protein described above was capable of binding to HMGB1. ELISA plates were coated with 3 µg/ml of recombinant rat HMGB1 (SEQ ID NO:12; FIG. 15B) and incubated overnight at 4° C. The plate was then blocked with PBS and 1% BSA for one hour at 37° C. After washing, RAGE-Ig fusion protein was added at the indicated concentrations and incubated at room temperature for 1 hour. The plates were then washed and bound RAGE-Ig was detected using anti-human IgG conjugated with horse radish peroxidase (Jackson ImmunoResearch Laboratories, West Grove, Pa.) diluted to 0.1 µg/ml in PBS. After washing, the plates were developed with TMB (Invitrogen, San Diego, Calif.) and absorbance at 655 nm was measured using a plate reader.

Figure 6:
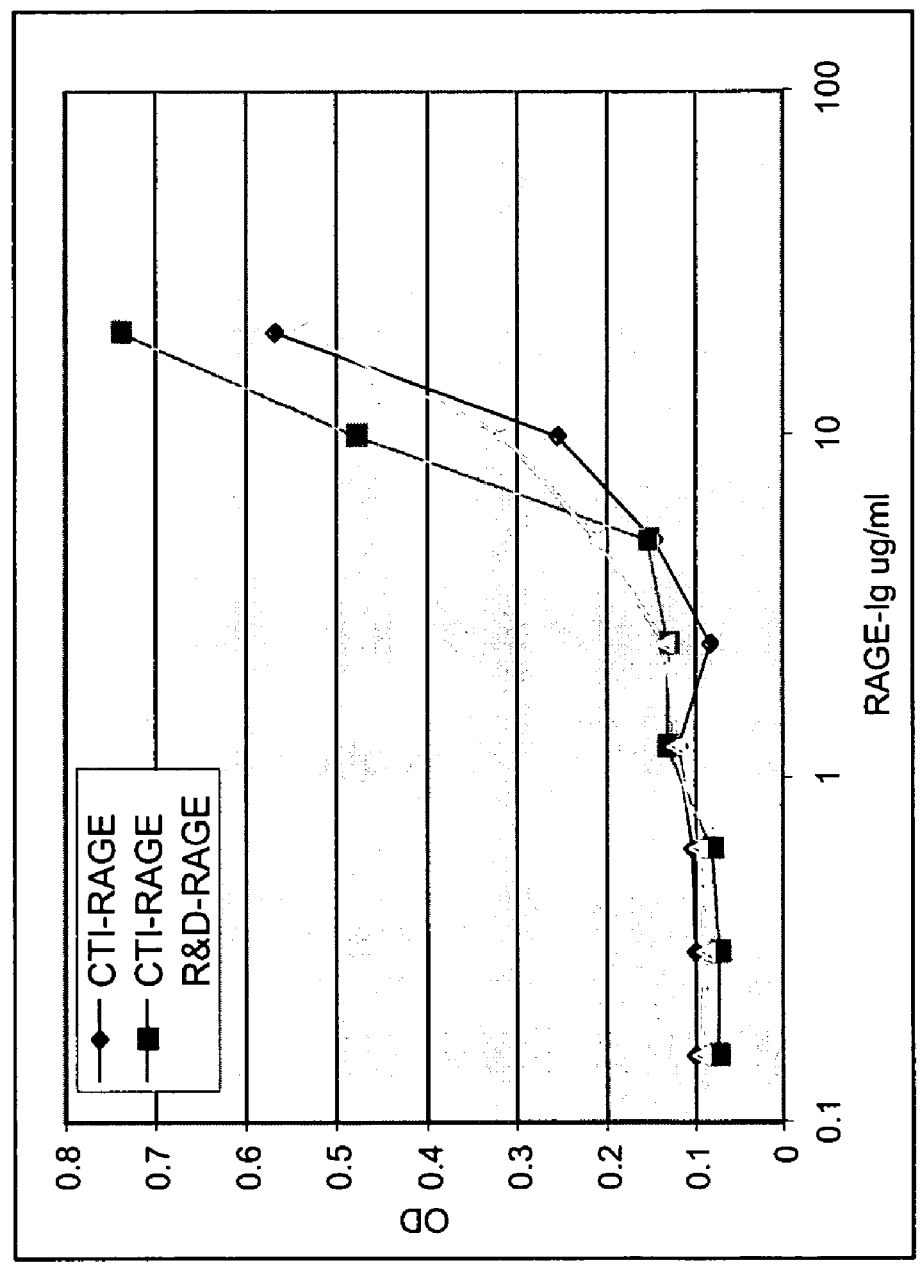
FIG. 6 is a graph depicting ELISA results, which demonstrate that the RAGE-Ig fusion proteins bind to HMGB1 in a dose-dependent manner. "R&D RAGE" corresponds to the commercially-available recombinant human RAGE/Fc chimera (R&D Systems, Inc., Minneapolis, Minn., Catalog No. 1145-RG); "CTI-RAGE" corresponds to the RAGE-Ig fusion protein (SEQ ID NO:6); –◆–CTI-RAGE and –■–CTI-RAGE correspond to batches of RAGE-Ig fusion proteins purified from CHO cells on different days.

FIG. 6 shows the results of this experiment. "R&D RAGE" corresponds to the commercially-available recombinant human RAGE/Fc chimera (R&D Systems, Inc., Minneapolis, Minn., Catalog No. 1145-RG). "CTI-RAGE" refers to the RAGE-Ig fusion protein described above; —◆—CTI-RAGE and —■—CTI-RAGE correspond to batches of RAGE-Ig fusion proteins purified from CHO cells on different days. As shown in FIG. 6, each of the RAGE-Ig fusion proteins bound recombinant HMGB1 in a dose-dependent manner. Further, as shown in FIG. 6, at 10 µg/ml of RAGE-Ig fusion protein, one purification batch of RAGE-Ig fusion protein bound to HMGB1 with a higher affinity than the commercially-available RAGE/Fc chimera.

EXAMPLE 8

RAGE-Ig Fusion Protein Binds HMGB1 A and B Boxes with Higher Affinity than the Commercially-Available RAGE/Fc Chimera The ability of the RAGE-Ig fusion proteins to bind to the HMGB1 A and B boxes was determined by ELISA. ELISA plates were coated with 5 µg/ml of human HMGB1 A and B box peptides. The HMGB1 A box corresponds to amino acids 9-85 of the HMGB1 sequence (amino acids 9-85 of SEQ ID NO:12; FIG. 15B). The HMGB1 B box corresponds to amino acids 91-169 of the HMGB1 sequence (amino acids 91-169 of SEQ ID NO:12; FIG. 15B). The ELISA was performed substantially as described above in Example 7.

The results of this experiment are presented in FIGS. 7A and 7B. As depicted in FIGS. 7A and 7B, the above-described RAGE-Ig fusion protein (FIG. 7A; labeled "CTI RAGE-Ig") and the commercially-available RAGE-Ig fusion protein (FIG. 7B; labeled "R&D RAGE-Ig") bound to the HMGB 1 A and B boxes, however, both of these RAGE-Ig fusion proteins bound more strongly to the HMGB1 B box. In addition, as shown in FIGS. 7A and 7B, the inventive RAGE-Ig fusion protein bound to both the HMGB1 A and B boxes with higher affinity than the commercially-available RAGE/Fc chimera (compare FIG. 7A showing binding of "CTI RAGE-Ig" to the HMGB1 A and B box with FIG. 7B showing binding of the commercially-available RAGE/Fc chimera to the HMGB1 A and B box).

EXAMPLE 9

RAGE-Ig Fusion Protein Inhibits HMGB1-Mediated TNF Release in B10.A Cells

B10.A cells, a mouse macrophage cell line (provided by Dr. Danuta Radzioch, McGill University, Canada), were incubated overnight with either 0.25 µg/ml (8 nM) of recombinant rat HMGB1 alone (labeled "HMGB1 Cntrl (CTI#030-43)"), RAGE-Ig fusion protein alone (the above-described RAGE-Ig fusion protein; labeled "RAGE-Ig (w/out HMGB1)") or a combination of 0.25 µg/ml of HMGB1 and RAGE-Ig fusion protein (labeled "RAGE-Ig (w/HMGB1)"). The RAGE-Ig fusion protein was added at the concentration indicated on the X-axis of FIG. 8. In all cases, the RAGE-Ig fusion protein and/or HMGB1 were made up in Opti-MEM supplemented with 2% FCS (both are from Invitrogen, Carlsbad, Calif.) and incubated at 37° C. The supernatants were harvested and the TNF-α concentration was measured using an ELISA kit (R&D Systems, Minneapolis, Minn.).

Figure 8:
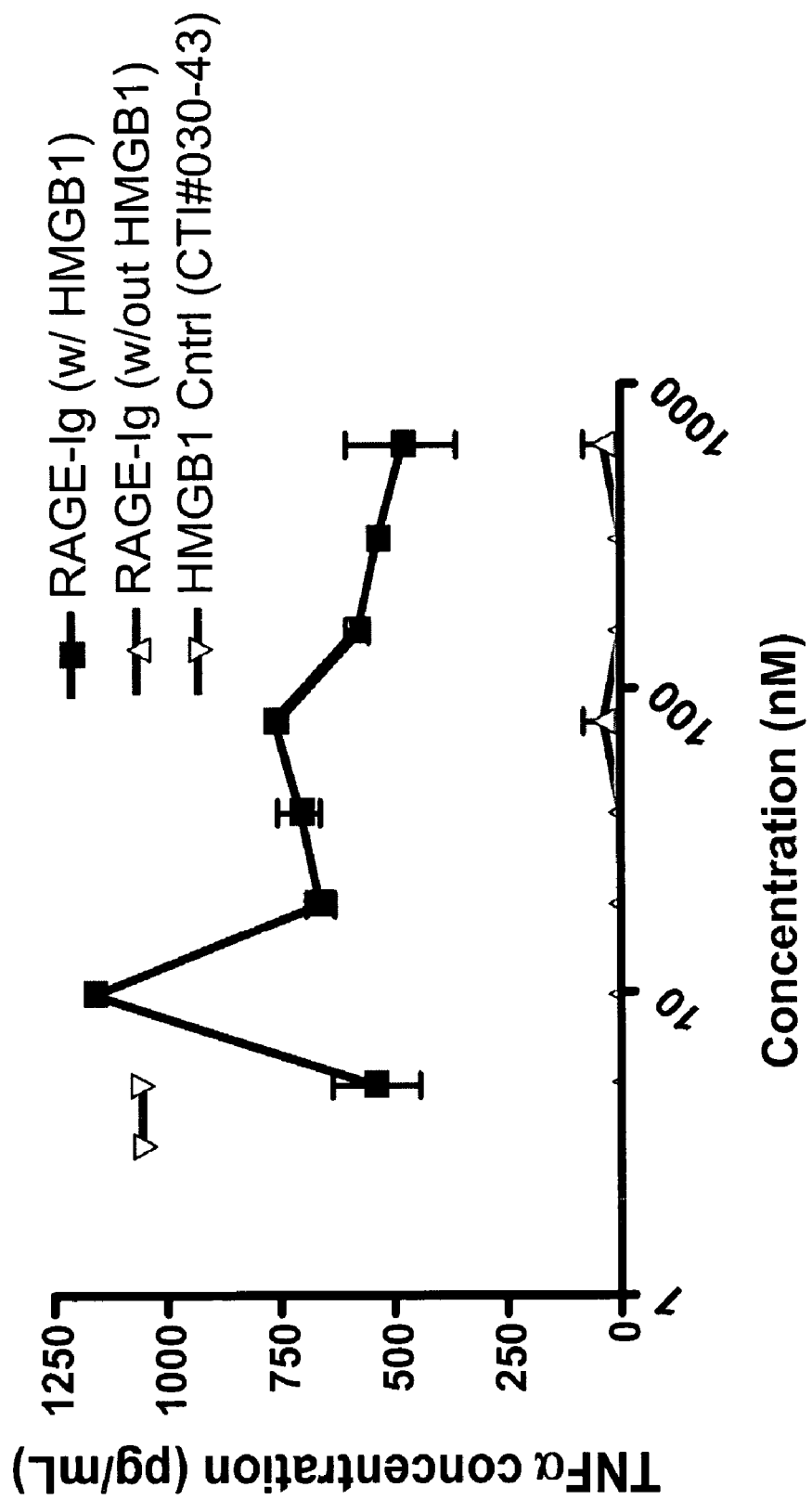
FIG. 8 is a graph showing that RAGE-Ig fusion protein inhibited HMGB1-mediated TNF release in B10.A cells.

The results of this experiment are depicted in FIG. 8. As shown in FIG. 8, TNF-α concentration was decreased in cells incubated with HMGB1 and the inventive RAGE-Ig fusion protein, as compared to cells incubated with HMGB1 alone. These results indicate that the inventive RAGE-Ig fusion protein inhibits HMGB1-mediated TNF release in B10.A cells.

EXAMPLE 10

RAGE-Ig Fusion Protein Inhibits HMGB1-Mediated TNF Release in BALB/c Bone Marrow Cells BALB/c bone marrow cells (Taconic, Germantown, N.Y.) were incubated overnight with either 1 µg/ml (30 nM) of HMGB1 alone (recombinant rat HMGB1; SEQ ID NO:12; labeled "HMGB1 only"), RAGE-Ig fusion protein alone (labeled "RAGE-Ig (w/out HMGB1)") or a combination of 0.25 µg/ml HMGB1 and RAGE-Ig fusion protein (labeled "RAGE-Ig (w/HMGB1)"). The RAGE-Ig fusion protein was added at the concentration indicated on the X-axis of FIG. 9. In all cases, the RAGE-Ig fusion protein and/or HMGB1 were made up in RPMI 1640/10% FCS (Invitrogen, Carlsbad, Calif.) and incubated at 37° C. The supernatants were harvested and the TNF concentration was measured using an ELISA kit (R&D Systems, Minneapolis, Minn.).

Figure 9:
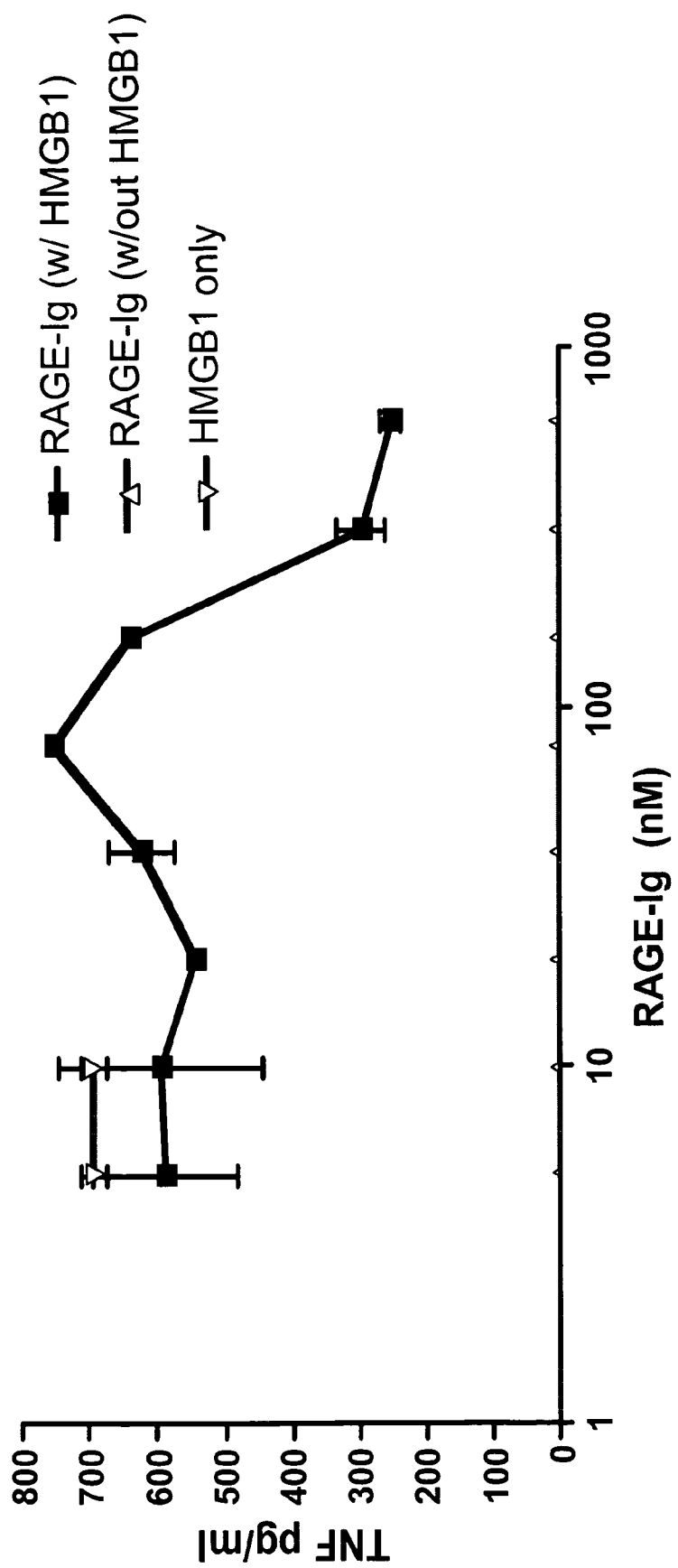
FIG. 9 is a graph showing that RAGE-Ig fusion protein inhibited HMGB1-mediated TNF release in BALB/c bone marrow cells.

The results of this experiment are depicted in FIG. 9. As shown in FIG. 9, TNF concentration was decreased in cells incubated with HMGB1 and the RAGE-Ig fusion protein, as compared to cells incubated with HMGB1 alone. These results indicate that the inventive RAGE-Ig fusion protein inhibits HMGB1-mediated TNF release in BALB/c bone marrow cells.

EXAMPLE 11

RAGE Binds to the HMGB1 A Box in the Area between Amino Acids 31-78 and Binds to the HMGB1 B Box in the Area between Amino Acids 121-158

In order to determine the RAGE-binding domains in HMGB1, competition ELISAs were performed using full-length rat HMGB1 (labeled "HMGB1"; SEQ ID NO:12), the human HMGB1 A Box (labeled "9-85 A-Box"), the human HMGB1 B Box (labeled "91-169 B-Box"), and various 18 to 30 amino acid peptide fragments of human HMGB1 (labeled with the prefix "huHMGB1-" and the respective amino acid sequence of the peptide). For the competition ELISAs, RAGE-Ig fusion protein was diluted in PBS and supplemented with 1% bovine serum albumin at 50 nM. Recombinant rat HMGB1, synthetic peptides corresponding to the human HMGB1 A-box or B-box subunits, and short peptide HMGB1 amino acid sequences (18 to 30 amino acid residues) spanning the entire HMGB1 protein sequence were diluted in the same buffer to 20 µM. The RAGE-Ig fusion protein solution and the solution containing HMGB1 or HMGB1 peptide fragment were mixed in a 1:1 ratio, resulting in a solution having a final RAGE-Ig concentration of 25 nM and an HMGB1 or HMGB1 peptide fragment concentration of 10 µM, respectively. The mixtures were incubated at room temperature for 30 minutes and 100 µl of each solution was transferred to an ELISA plate that was coated with recombinant rat HMGB1 at 60 nM. After a 30-minute incubation period, the ELISA plate was washed and the bound RAGE-Ig fusion protein was detected using anti-human IgG conjugated to HRP (Jackson ImmunoResearch Laboratories, West Grove, Pa.) and developed using TMB as the substrate. The plate was then read in a plate reader at 650 nm.

As shown in FIGS. 10A to 10C, RAGE-Ig fusion protein bound to solid-phase HMGB1, and this binding was inhibited by soluble HMGB1, HMGB1 A box and HMGB1 B box. Further, as depicted in FIGS. 10A to 10C, there are two amino acid regions within the HMGB1 protein that inhibit binding of RAGE to HMGB1. The first region consists of amino acids 31 to 78, which is a region within the A box domain of HMGB1. The second region consists of amino acids 121 to 168, which is a region within the B-box domain of HMGB1. As depicted in FIG. 10C, although HMGB1 peptide 150-183 could efficiently compete and inhibit RAGE binding, HMGB1 peptide 157-174 was less effective in competing for RAGE binding and HMGB1 peptide 158-175 failed to compete and inhibit RAGE binding. These results indicate that this RAGE binding domain of HMGB1 is confined to the region of HMGB1 consisting of amino acids 121-158. FIGS. 10A and 10B show similar results using different purification batches of the RAGE-Ig fusion protein.

EXAMPLE 12

RAGE-Ig Fusion Protein Inhibits HMGB1-Mediated IL-6 Release in Human PBMCs

Peripheral blood mononuclear cells (PBMCs) were isolated from whole blood using Ficoll. $2 \times 10^5$ PBMCs were placed in a microtiter well and were incubated overnight with recombinant rat HMGB1 only (labeled "HMGB1 only"; SEQ ID NO:12), HMGB1 plus 50 µg/ml of RAGE-Ig fusion protein (labeled "HMGB1+RAGE-fusion") or HMGB1 plus 50 µg/ml of the monoclonal HMGB1 antibody, 6E6 HMGB1 mAb (labeled "HMGB1+6E6"). HMGB1 was added at the concentrations indicated on the X-axis of FIG. 11, and the HMGB1 and/or RAGE-Ig fusion protein and/or 6E6 HMGB1 mAb solutions were made up in OPTI-MEM/2% FBS (Invitrogen, Carlsbad, Calif.) with 15 units/ml of Polymyxin B (Sigma Chemical Co., St. Louis, Mo.) and incubated at 37° C. The cell supernatants were harvested, IL-6 concentrations were measured using a human CBA assay (BD Biosciences, San Jose, Calif.) and results were read using a FACS.

Figure 11:
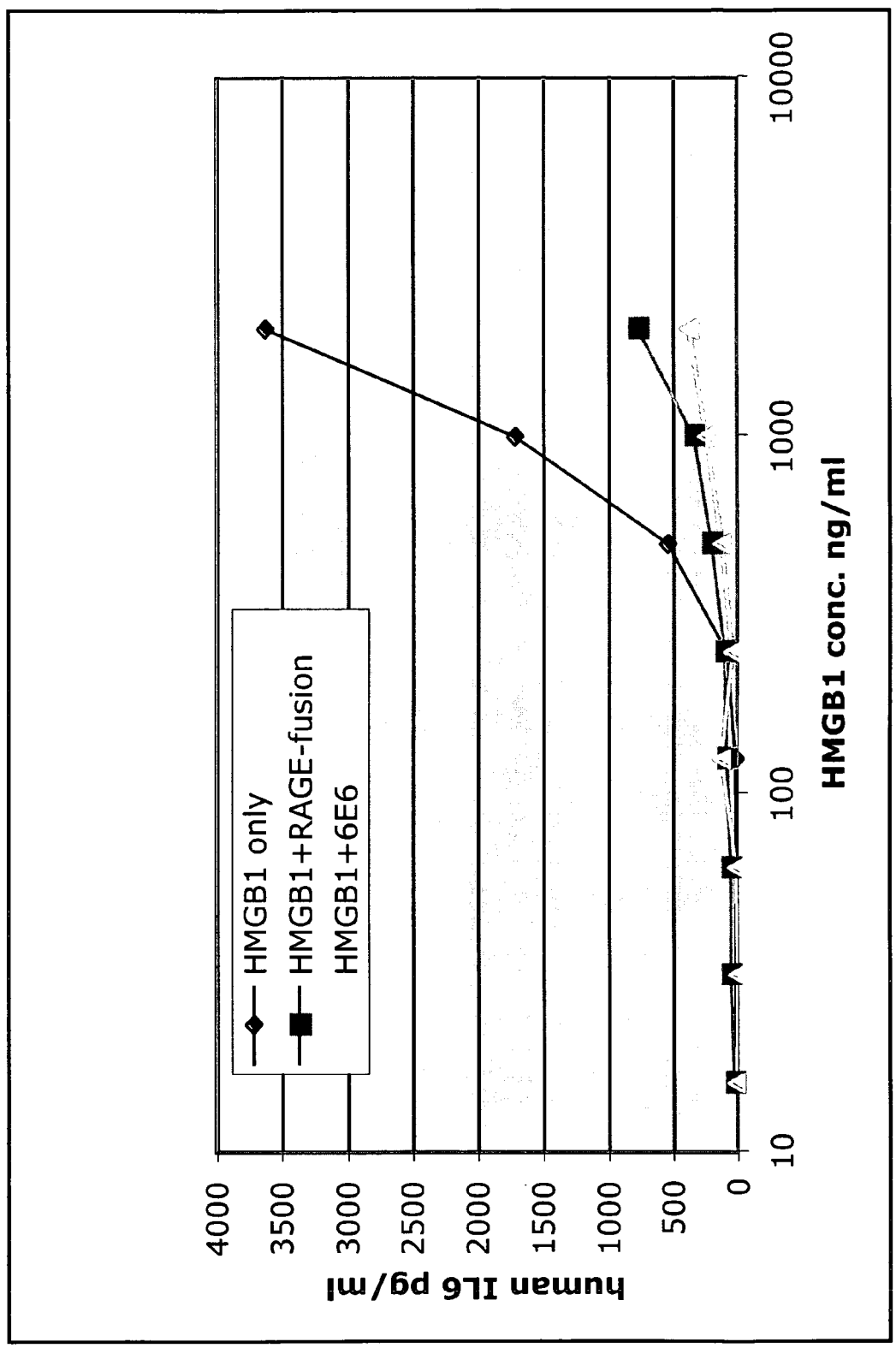
FIG. 11 is a graph showing that RAGE-Ig fusion protein and the monoclonal HMGB1 antibody, 6E6 HMGB1 mAb, inhibited HMGB1-mediated IL-6 release in peripheral blood mononuclear cells (PBMCs) to a similar extent.

The results of these experiments are depicted in FIG. 11. As shown in FIG. 11, IL-6 concentrations were decreased in cells incubated with HMGB1 and the RAGE-Ig fusion protein, as compared to IL-6 concentrations in cells incubated with HMGB1 alone. Further, as shown in FIG. 11, the concentration of IL-6 was also decreased in cells incubated with HMGB1 and the HMGB1 monoclonal antibody, 6E6 HMGB1 mAb. These results indicate that the inventive RAGE-Ig fusion protein inhibits HMGB 1-mediated IL-6 release in human PBMCs at a level comparable to that of 6E6 HMGB1 mAb.

6E6 HMGB1 mAb, also referred to as 6E6-7-1-1 or 6E6, can be produced by murine hybridoma 6E6 HMGB1 mAb, which was deposited on Sep. 3, 2003, on behalf of Critical Therapeutics, Inc., 675 Massachusetts Avenue, 14th Floor, Cambridge, Mass. 02139, U.S.A., at the American Type Culture Collection, 10801 University Boulevard, Manassas, Va. 20110, U.S.A., under Accession No. PTA-5433.

EXAMPLE 13

RAGE-Ig Fusion Protein Inhibits HMGB1-Mediated IL-10 Release in Human PBMCs

Peripheral blood mononuclear cells (PBMCs) were isolated from whole blood using Ficoll. $2 \times 10^5$ PBMCs were placed in a microtiter well and were incubated overnight with recombinant rat HMGB1 only (labeled "HMGB1 only"; SEQ ID NO:12, HMGB1 plus 50 µg/ml of RAGE-Ig fusion protein (labeled "HMGB1+RAGE-fusion") or HMGB1 plus 50 µg/ml of the monoclonal HMGB1 antibody, 6E6 HMGB1 mAb (labeled "HMGB1+6E6"). HMGB1 was added at the concentrations indicated on the X-axis of FIG. 11, and the HMGB1 and/or RAGE-Ig fusion protein and/or 6E6 HMGB1 mAb solutions were made up in OPTI-MEM/2% FBS (Invitrogen, Carlsbad, Calif.) with 15 units/ml of Polymyxin B (Sigma Chemical Co., St. Louis, Mo.) and incubated at 37° C. The cell supernatants were harvested, IL-10 concentrations were measured using a human CBA assay (BD Biosciences, San Jose, Calif.) and results were read using a FACS.

Figure 12:
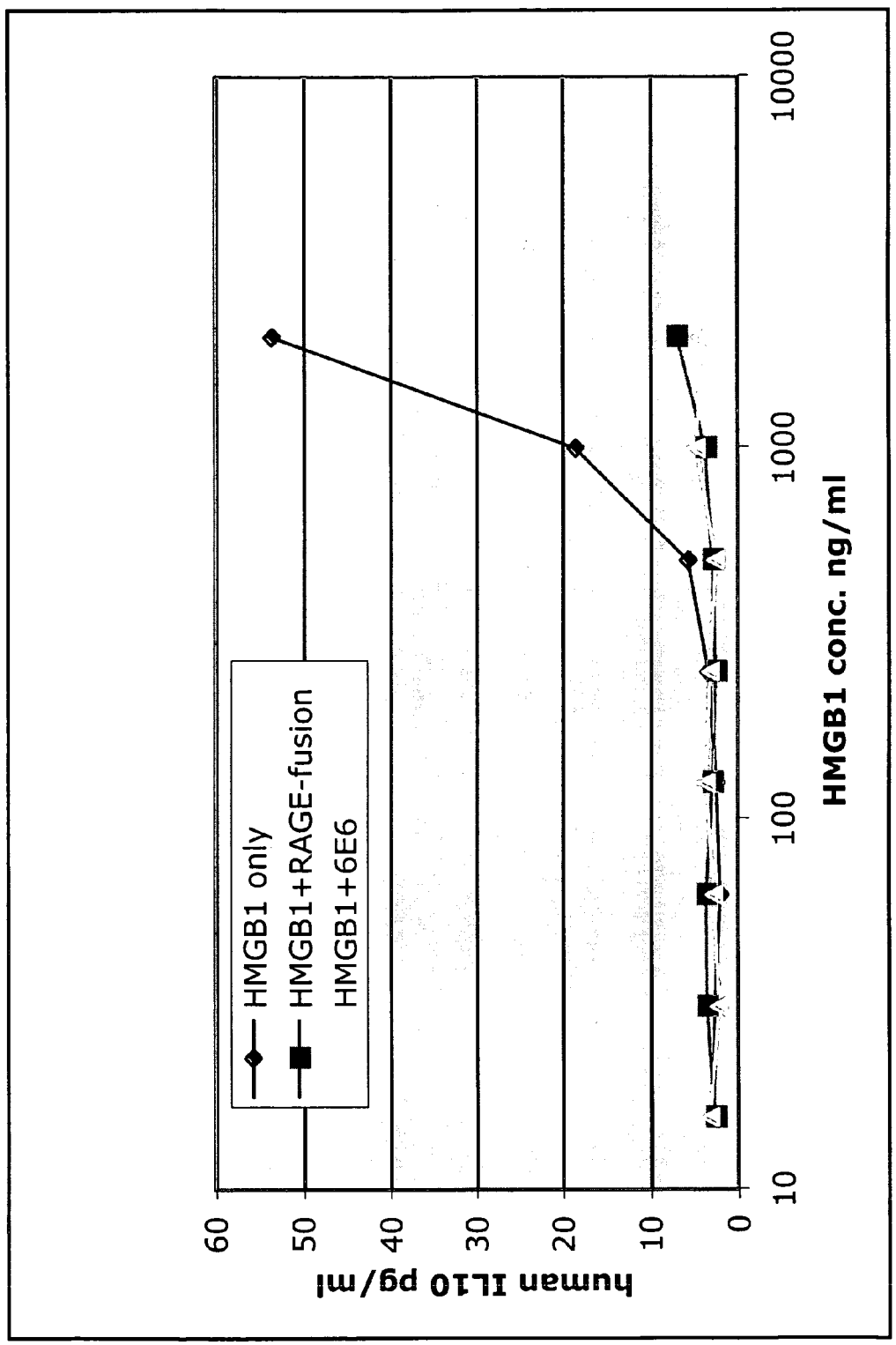
FIG. 12 is a graph showing that RAGE-Ig fusion protein and the monoclonal HMGB1 antibody, 6E6 HMGB1 mAb, inhibited HMGB1-mediated IL-10 release in peripheral blood mononuclear cells (PBMCs) to a similar extent.

The results of these experiments are depicted in FIG. 12. As shown in FIG. 12, IL-10 concentrations were decreased in cells incubated with HMGB1 and the RAGE-Ig fusion protein, as compared to IL-10 concentrations in cells incubated with HMGB1 alone. Further, as shown in FIG. 12, the concentration of IL-10 was also decreased in cells incubated with HMGB1 and the HMGB1 monoclonal antibody, 6E6 HMGB1 mAb. These results indicate that the inventive RAGE-Ig fusion protein inhibits HMGB1-mediated IL-10 release in human PBMCs at a level comparable to that of 6E6 HMGB1 mAb.

EXAMPLE 14

Construction of 1-Domain and 2-Domain RAGE-Ig Fusion Vectors 1-domain and 2-domain RAGE-Ig fusion protein can be created by PCR assembly in which two overlapping cDNA fragments are created, annealed by PCR and used as a template for the final PCR product. The 1-domain RAGE-Ig fusion protein will contain the RAGE signal sequence and first extracellular Ig-like domain of RAGE and a few additional amino acids to allow for stable folding (e.g., amino acids 1-111 of human RAGE 1-domain RAGE-Ig fusion protein; SEQ ID NOS:8 and 9 (FIGS. 13A and 13B), wherein the start methionine is designated as position 1). The 2-domain RAGE-Ig fusion protein will contain the RAGE signal sequence and the first and second extracellular Ig-like domains of RAGE and a few additional amino acids to allow for stable folding (e.g., amino acids 1-211 of human RAGE) (2-domain RAGE-Ig fusion protein; SEQ ID NOS:9 and 10 (FIGS. 14A and 14B)).

The DNA sequence for the 5' sections of the 1-domain and 2-domain RAGE-Ig fusion proteins can be amplified using the RAGE-Ig cDNA (SEQ ID NO:5) contained in pCTi-TOK31 as the template. For the 1-domain RAGE-Ig fusion protein, the oligonucleotide primers pTOK16a5 (SEQ ID NO:25) and pTOK39aA (SEQ ID NO:29), can be used to amplify the 5' section and the oligonucleotide primers pTOK39aB (SEQ ID NO:30) and pTOK10a3 (SEQ ID NO:33), can be used to amplify the 3' section. For the 2-domain RAGE-Ig fusion protein, the oligonucleotide primers pTOK16a5 (SEQ ID NO:25) and pTOK40aA (SEQ ID NO:31), can be used to amplify the 5' section and the oligonucleotide primers pTOK10a3 (SEQ ID NO:33) and pTOK40aB (SEQ ID NO:32), can be used to amplify the 3' section. The oligonucleotide primer pTOK16a5 contains the sequence for an EcoRI restriction site and a Kozak sequence. The oligonucleotide primer pTOK10a3 contains the sequence for a stop codon and XbaI restriction site. The oligonucleotide primers pTOK39aA and pTOK40aA anneal to the last 30-35 nucleotides of the desired RAGE DNA segment and overlap with the 5' 20 nucleotides of oligonucleotide primer pTOK39aB and pTOK40aB, respectively. The oligonucleotide primers pTOK39aB and pTOK40aB anneal to the first 35-40 nucleotides of the desired human IgG1 Fc region. This human IgG1 Fc region also contains the cDNA sequence with the Fc receptor region removed by mutation (L235A and G237A; corresponding to EU numbering (Edelman, G. M. et al., *Proc. Natl. Acad. Sci. USA* 63:78-85 (1969)), as well as the hinge, CH2 and CH3 regions (amino acids 219-447).

The PCR cycle can involve 1 step at 94° C. for 2 minutes, followed by 30 cycles at 94° C. for 1 minute, 55° C. for 30 seconds and 72° C. for 5 minutes, followed by a step at 72° C. for 10 minutes. The two fragments in each reaction can be gel purified and combined in equal molar ratios in a PCR reaction without primers, and cycled in a PCR reaction comprising a step at 94° C. for 2 minutes, followed by 8 cycles at 94° C. for 2 minute and 72° C. for 5 minutes with a 30-second ramping interval, followed by a step at 72° C. for 10 minutes. The products of these reactions can serve as templates in another amplification reaction using the primers pTOK16a5 (SEQ ID NO:25) and pTOK10a3 (SEQ ID NO:33) for both constructs with the same cycler steps used in the first amplification reaction. The products can be TA-cloned and sequenced to find the correct cDNA construct.

The EcoRI-XbaI fragments of the correct cDNAs can be cloned into the vector pCTiTOK29 to create the expression vectors pCTiTOK39 and pCTiTOK40. After confirmation of the correct sequence, the respective DNA can be max-iprepped and transfected into CHO cells. CHO cells can be transfected with 1-domain and 2-domain RAGE-Ig fusion protein as described above in Example 5. Protein production can be tested as described above in Example 6. The nucleotide (SEQ ID NO:7) and amino acid sequence (SEQ ID NO:8) of the 1-domain RAGE-Ig fusion protein is depicted in FIGS. 13A and 13B, respectively. The nucleotide (SEQ ID NO:9) and amino acid sequence (SEQ ID NO:10) of the 2-domain RAGE-Ig fusion protein is depicted in FIGS. 14A and 14B, respectively. The above-described oligonucleotide primers that could be used to create the 1-domain and 2-domain RAGE-Ig fusion constructs are depicted in Table 4 below.

TABLE 4

Oligonucleotide Primers to Create the 1-domain and
2-domain RAGE-Ig Fusion Proteins

| Primer | Sequence | SEQ ID NO: |
|---|---|---|
| pTOK16a5 | CCGGAATTCCTCACCATGGCAGCCGGAACAGCAGTTGGAG | SEQ ID NO:25 |
| pTOK39aA | GTTTTGTCGCTGGACTTGGTCTCCTTTCCATTCCTGTTCATTGCCTGGCACCG | SEQ ID NO:29 |
| pTOK39aB | GTTTTGTCGCTGGACTTGGTCTCCTTTCCATTCCTGTTCATTGCCTGGCACCG | SEQ ID NO:29 |
| pTOK40aA | CGGTGGGCATGTGTGAGTTTTGTCGCTGGAGTGTCGGGGAAGGCCTGGGCTGAAGCTACAG | SEQ ID NO:31 |
| pTOK40aB | CTCCAGCGACAAAACTCACACATGCCCACCGTGCCCAGCACCTG | SEQ ID NO:32 |
| pTOK10a3 | TGCTCTAGATTATTTACCCGGAGACAGGGAGAGGCTCTTCTGCGTGTAGTGGTTGTGCAGAGCCTCATGCATCACGG | SEQ ID NO:33 |

EXAMPLE 15

Methods for Using RAGE-Ig as a Capture Reagent to Detect Native HMGB1

Recombinant RAGE-Ig fusion protein was coated in a flat bottom 96-well plate at 5 μg/ml. After overnight incubation, the plate was blocked with 5% fat-free milk. After washing, the plate was incubated with samples containing native HMGB1. Native HMGB1 was obtained either from cultured monocyte supernatants or by freeze-thawing mouse fibroblast cells, as described by Scaffidi, P., et al., Nature 418 (6894):191-195 (2002). Samples were incubated in RAGE-coated wells overnight under gentle shaking.

A mouse anti-HMGB1 mAb, 10D4 HMGB1 mAb (also known as clone 10D4) was used to detect RAGE-bound HMGB1. Lysates from HMGB1 knockout cells were used as a control to show that binding was specific for HMGB1.

A feature of this protocol is that it uses a natural receptor of HMGB1 to capture HMGB1. Thus, RAGE not only binds recombinant HMGB1, but also binds to native HMGB1, while monoclonal antibodies raised against recombinant HMGB1 may not recognize native HMGB1.

Figure 17:
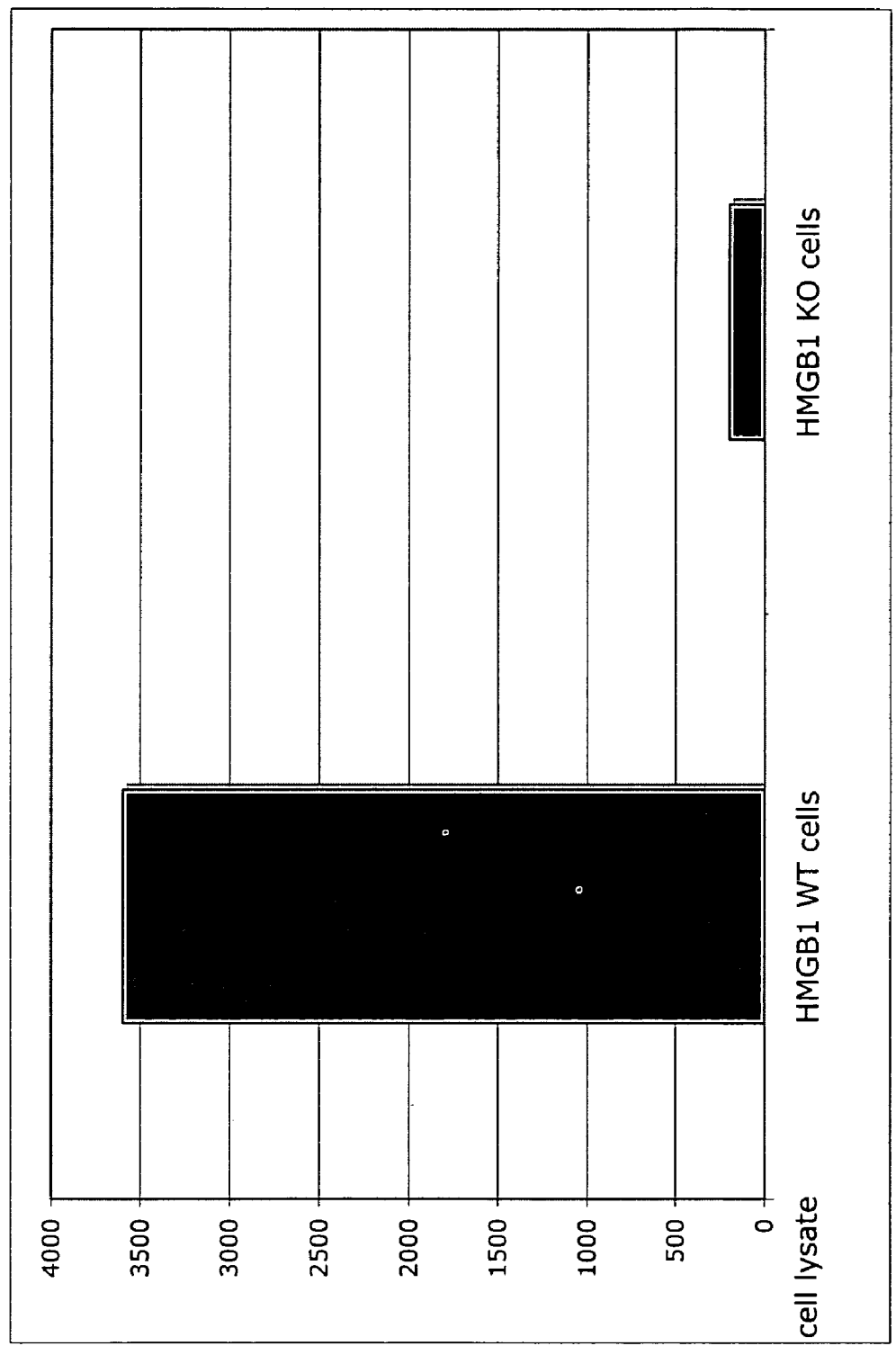
FIG. 17 is a bar graph showing that RAGE-Ig-bound HMGB1 was detected with mouse anti-HMGB1 mAb 10D4 and that binding was specific for HMGB 1, as only the lysates from wildtype cells, and not HMGB1 knock-out (KO) cells, gave a detectable signal. Cell lysates that were made from freeze-thawed fibroblasts from wildtype (WT) or HMGB1 KO mice were incubated in RAGE-Ig coated plates.

As can be seen in FIGS. 16A and 16B, RAGE-Ig bound both recombinant HMGB1 (FIG. 16A) and HMGB1 produced in monocytes cultures (FIG. 16B). RAGE-bound HMGB1 was detected with mouse anti-HMGB1 mAb 10D4. Moreover, as shown in FIG. 17, binding of RAGE in a cell lysate was specific for HMGB1, as only the lysates from wildtype cells, and not HMGB1 knock-out (KO) cells, gave a detectable signal.

Thus, in view of the results described herein, the RAGE-Ig fusion proteins of the invention can be used to screen antibodies that recognize native HMGB1. Such antibodies could represent effective therapeutic agents. Accordingly, in one embodiment, the invention is a method of screening antibodies to identify an antibody that recognizes native HMGB1. In another embodiment, the invention is a method of screening antibodies to identify an antibody that inhibits native HMGB1 binding to a receptor (e.g., RAGE). In another embodiment, the invention is a method of selecting an antibody that is specific for native HMGB1. Such antibodies could serve as effective diagnostic reagents.

In one embodiment, the invention is a method of selecting an antibody that recognizes different forms of HMGB1, e.g., free HMGB1 or protein-bound HMGB1. As described herein and is known in the art, HMGB1 can act as a pro-inflammatory cytokine (Yang H., et al., Shock 15:247-53 (2001)), and can be actively secreted by macrophages/monocytes in response to inflammatory stimuli (Wang H., et al., Science 285:248-51 (1999)). During secretion, HMGB1 exits the nucleus and is transported through the cytoplasm, where it is actively released to the extracellular space. HMGB1 can also be passively released from the nuclei of necrotic or damaged cells (Scaffidi P., et al., Nature 418:191-95 (2002)). Both TNF-α and IL-1β have been shown to stimulate the release of HMGB1 (Wang H., et al., Surgery 126:389-92 (1999)), and HMGB1 may in turn stimulate the synthesis of pro-inflammatory cytokines (Andersson, U., et al., J. Exp. Med. 192: 565-570 (2000)). Thus, given the important role that HMGB1 has in mediating inflammation, it would be beneficial to be able to detect particular forms of HMGB1 (e.g., free HMGB1, protein-bound HMGB1). The RAGE-Ig fusion proteins of the invention allow for this.

The relevant teachings of all publications cited herein not previously incorporated by reference, are incorporated herein by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A fusion protein comprising at least a first and a second polypeptide, wherein:
said first polypeptide consists of a fragment of a Receptor for Advanced Glycation End Product (RAGE) extracellular domain wherein said fragment consists of amino acid residue 1 to amino acid residue 305 of SEQ ID NO:2; and
said second polypeptide comprises an immunoglobulin element, wherein said immunoglobulin element comprises from about amino acid residue 101 to about amino acid residue 329 of SEQ ID NO:4.

2. A fusion protein comprising at least a first and a second polypeptide, wherein:
said first polypeptide consists of a fragment of a Receptor for Advanced Glycation End Product (RAGE) extracellular domain, said fragment of a RAGE extracellular domain is a human RAGE extracellular domain and comprises from about amino acid residue 19 to about amino acid residue 305 of SEQ ID NO:2; and
said second polypeptide comprises an immunoglobulin element, wherein said immunoglobulin element comprises from about amino acid residue 101 to about amino acid residue 329 of SEQ ID NO:4.

3. A fusion protein comprising the amino acid sequence depicted in SEQ ID NO:6.

4. The fusion protein of claim 1, wherein said immunoglobulin element comprises an Fc domain.

5. The fusion protein of claim 1, wherein said immunoglobulin element comprises an immunoglobulin heavy chain.

6. The fusion protein of claim 1, wherein said immunoglobulin element comprises a $C_H1$ domain and a Fc domain.

7. A pharmaceutical composition comprising the fusion protein of claim 1 in a pharmaceutically-acceptable excipient.

8. The pharmaceutical composition of claim 7 further comprising an antibody or antigen-binding fragment thereof that binds to an HMGB1 polypeptide or an antigenic fragment of said HMGB1 polypeptide.

9. A nucleic acid encoding a fusion protein, wherein said fusion protein comprises at least a first and a second polypeptide, wherein:
said first polypeptide consists of a fragment of a Receptor for Advanced Glycation End Product (RAGE) extracellular domain, wherein said fragment consists of amino acid residue 1 to amino acid residue 305 of SEQ ID NO:2; and
said second polypeptide comprises an immunoglobulin element, wherein said immunoglobulin element comprises from about amino acid residue 101 to about amino acid residue 329 of SEQ ID NO:4.

10. An expression vector comprising the nucleic acid of claim 9.

11. A cell transfected with the expression vector of claim 10.

12. A method of producing a fusion protein comprising culturing the cell of claim 11 in a cell culture medium suitable for expression of the fusion protein and expressing said fusion protein.

13. A nucleic acid encoding a fusion protein, wherein said fusion protein comprises at least a first and a second polypeptide, wherein:
   said first polypeptide consists of a fragment of a Receptor for Advanced Glycation End Product (RAGE) extracellular domain, said fragment of a RAGE extracellular domain is a human RAGE extracellular domain and comprises from about amino acid residue 19 to about amino acid residue 305 of SEQ ID NO:2; and
   said second polypeptide comprises an immunogloublin element, wherein said immunoglobulin element comprises from about amino acid residue 101 to about amino acid residue 329 of SEQ ID NO:4.

14. An expression vector comprising the nucleic acid of claim 13.

15. A cell transfected with the expression vector of claim 14.

16. A method of producing a fusion protein, comprising culturing the cell of claim 15 in a cell culture medium suitable for expression of the fusion protein and expressing said fusion protein.

17. A nucleic acid encoding a fusion protein, wherein said fusion protein comprises the amino acid sequence depicted in SEQ ID NO:6.

18. An expression vector comprising the nucleic acid of claim 17.

19. A cell transfected with the expression vector of claim 18.

20. A method of producing a fusion protein, comprising culturing the cell of claim 19 in a cell culture medium suitable for expression of the fusion protein and expressing said fusion protein.

21. The fusion protein of claim 2 wherein said immunoglobulin element comprises an Fc domain.

22. The fusion protein of claim 2, wherein said immunoglobulin element comprises an immunoglobulin heavy chain.

23. The fusion protein of claim 2 wherein said immunoglobulin element comprises a $C_H1$ domain and a Fc domain.

24. A pharmaceutical composition comprising the fusion protein of claim 2 in a pharmaceutically-acceptable excipient.

* * * * *